United States Patent [19]
Nakaya et al.

[11] Patent Number: 5,792,557
[45] Date of Patent: Aug. 11, 1998

[54] ORGANIC EL ELEMENT

[75] Inventors: Kenji Nakaya; Tetsushi Inoue, both of Chiba, Japan

[73] Assignee: TDK Corporation, Tokyo, Japan

[21] Appl. No.: 385,479

[22] Filed: Feb. 8, 1995

[30] Foreign Application Priority Data

Feb. 8, 1994 [JP] Japan ................... 6-014379
Jun. 3, 1994 [JP] Japan ................... 6-145293

[51] Int. Cl.$^6$ ........................... H05B 33/12
[52] U.S. Cl. ............... 428/411.1; 313/504; 313/506; 428/457; 428/690; 428/704; 428/917
[58] Field of Search ................ 428/690, 704, 428/9, 7, 457, 411.1; 313/504, 506

[56] References Cited

U.S. PATENT DOCUMENTS

| | | | |
|---|---|---|---|
| 4,720,432 | 1/1988 | VanSlyke et al. | 428/457 |
| 5,061,569 | 10/1991 | VanSlyke et al. | 428/457 |
| 5,085,946 | 2/1992 | Saito et al. | 428/690 |
| 5,338,634 | 8/1994 | Ueda | 430/59 |
| 5,405,709 | 4/1995 | Littman et al. | 428/690 |

FOREIGN PATENT DOCUMENTS

| | | |
|---|---|---|
| 0 508 562 | 10/1992 | European Pat. Off. . |
| 0 510 541 | 10/1992 | European Pat. Off. . |
| 0 650 955 | 5/1995 | European Pat. Off. . |

(List continued on next page.)

OTHER PUBLICATIONS

Helv. Chim. Acta, vol. 7, 1924, pp. 789–799.
Extended Abstracts of the 39th Spring Meeting, 1992 of The Japan Society of Applied Physics and Related Societies, No. 3, 28p-Q-8, "Characteristics of the Organic EL Device Doped with Rubrene", H. Kanai, et al., p. 1036.
Preprint of Workshop 92 of the Japanese Research Association for Organic Electronics Materials (JOEM), 1992, Sato, et al., pp. 31–39.
Extended Abstracts of 54th Autumn Meeting, 1993 of The Japan Society of Applied Physics, No. 3, 29p–ZC–7, "Characteristics of Organic EL Cells Based on Doped Hole Transport Layer", T. Fujii, et al., p. 1124.
Caoutchoucs & Plastiques Sommaire, No. 561, Jun. 1976, pp. 57–59, G. Friedmann, et al., "Polymerisation De L'Isoprene Par Catalyse Ziegler–Matta En Presence De Diamines Aromatiques".
Chemical Abstract Society, 1993, RN: 122909-77-7 and 66989-45-5.

*Primary Examiner*—Marie Yamnitzky
*Attorney, Agent, or Firm*—Oblon, Spivak, McClelland, Maier & Neustadt, P.C.

[57] ABSTRACT

Tetraaryldiamie derivatives of formula (1) are used in organic EL elements.

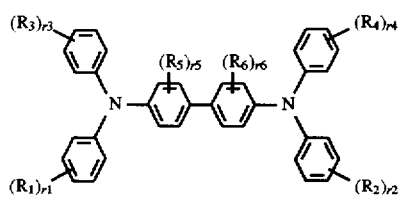

$R_1$, $R_2$, $R_3$, and $R_4$ represent aryl, alkyl, alkoxy, aryloxy, amino or halogen, at least one of $R_1$ to $R_4$ is an, aryl group, r1, r2, r3, and r4 are 0 or an integer of 1 to 5, the sum of r1 to r4 is at least 1, $R_5$ and $R_6$ represent alkyl, alkoxy, amino or halogen, r5 and r6 are 0 or an integer of 1 to 4. The inventive compounds have high m.p. and high Tg and can be evaporated to deposit tranparent smooth thin films of quality which maintain a stable amorphous state are room temperature over a long term. Organic EL elements using the invertive compound in an organic compound layer, typically a hole injecting and transporting layer thereof provide uniform plane light emission and maintain a high intensity of luminescence in a stable manner over a long term. Thus the elements are fully durable and reliable.

38 Claims, 11 Drawing Sheets

FOREIGN PATENT DOCUMENTS

| | | |
|---|---|---|
| 0 721 935 | 7/1996 | European Pat. Off. . |
| 63-295695 | 12/1988 | Japan . |
| 2-207488 | 8/1990 | Japan . |
| 2-250292 | 10/1990 | Japan . |
| 2-277071 | 11/1990 | Japan . |
| 2-291696 | 12/1990 | Japan . |
| 3-114197 | 5/1991 | Japan . |
| 3-190088 | 8/1991 | Japan . |
| 3-289090 | 12/1991 | Japan . |
| 4-178487 | 6/1992 | Japan . |
| 4-334894 | 11/1992 | Japan . |
| 4-357694 | 12/1992 | Japan . |
| 5-78655 | 3/1993 | Japan . |
| 5-182762 | 7/1993 | Japan . |
| 5-234681 | 9/1993 | Japan . |
| 5239455 | 9/1993 | Japan . |
| 5299174 | 11/1993 | Japan . |

ORGANIC EL ELEMENT

This invention relates to an organic electroluminescent (EL) element using an organic compound in the form of a tetraaryldiamine derivative.

BACKGROUND OF THE INVENTION

Low molecular weight organic compound which turn to be conductive or produce electric charges upon exposure to light, that is, have a photo-electronic function are well known in the art. Since most of such compounds do not possess an ability to form a thin film by themselves, they must be dispersed in or diluted with binder resins and coated onto substrates to form thin films. Some compounds have an ability to form a thin film by themselves when applied by vacuum deposition. These film-forming compounds, however, are insufficient in thin film stability and liable to physical changes, typically phase transition.

Specific tetraaryldiamines are disclosed in Japanese Patent Application Kokai (JP-A) No. 277071/1990 as a material for forming a photosensitive layer on an electrophotographic photoconductor. Their potential use as an organic EL element-forming compound is suggested nowhere.

Organic electroluminescent (EL) elements include a thin film containing a luminescent organic compound interleaved between a cathode and an Code. Electrons and holes are injected into the thin film where they are recombined to create excitons. Light is emitted by utilizing luminescence (phosphorescence or fluorescence) upon deactivation of Excitons. The organic EL elements are characterized by plane light emission at a high luminance of about 100 to 100.000 cd/m$^2$ with a low voltage of about 10 volts and light emission in a spectrum from blue to red color by a simple choice of the type of fluorescent material.

The organic EL elements, however, are undesirably short an effective life, less durable and less reliable because of the following factors.

(1) Physical changes of organic compounds: Development and growth of grain boundaries render the interface non-uniform, which causes deterioration of electric charge injecting ability, short-circuiting and dielectric breakdown of the element. Particularly when a low molecular weight compound having a molecular weight of less than 500 is used, grain boundaries develop and grow, substantially detracting from film quality. Even when the interface with indium tin oxide (ITO) is rough, significant development and growth of grain boundaries occur to lower luminous efficiency and allow current leakage, ceasing to emit light. Local dark spots are also formed.

(2) Oxidation and stripping of the cathode: Although metals having a low work function such as Mg, Li, Na, and Al are used as the cathode in order to facilitate electron injection, these metals are reactive with oxygen and moisture in air. As a result, the cathode can be stripped from the organic compound layer, prohibiting electric charge injection. Particularly when a polymeric compound is applied by a wet process such as spin coating, the residual solvent and decomposed products resulting from film formation promote oxidative reaction of the electrodes which can be stripped to create local dark spots.

(3) Low luminous efficiency and increased heat build-up: Since electric current is conducted across an organic compound, the organic compound is placed under an electric field of high strength and cannot help heating. The heat causes melting, crystallization or decomposition of the organic compound, leading to deterioration or failure of the element.

(4) Photo-chemical and electrochemical changes of organic compound layers.

One solution to these problems is an organic EL device comprising a hole injecting and transporting zone including a hole injecting porphyrinic compound and a hole transporting aromatic tertiary amine as disclosed in VanSlyke at al. U.S. Pat. No. 4,120,432 or JP-A 295695/1988. More particularly, the EL devices prepared in Examples 1, 10 and 11 include a transparent anode of indium tin oxide coated glass, a hole injecting copper phthalocyanine PC-10 layer (35 nm or 37.5 nm), a hole transporting 1,11'-bis(4-di-p-tolylaminophenyl)cyclohexane ATA-1 layer (35 nm or 37.5 nm), a light emitting and electron injecting and transporting aluminum trisoxine CO-1 layer (60 nm), and a Mg-Ag cathode (200 nm). When these devices were driven for 500 hours at a constant current density of 5 mA/cm$^2$, the light output declined from 0.08 mW/cm$^2$ at the initial to 0.05 mW/cm$^2$ at the final (percentage decline 37.5%). At a current density of 20 mA/cm$^2$, the light output declined from 0.45 mW/cm$^2$ at the initial to 0.06 mW/cm$^2$ at the final (percentage decline 86.7%). At a current density of 40 mA/cm$^2$, the light output declined from 1.15 mW/cm$^2$ at the initial to <0.1 mW/cm$^2$ at the final (percentage decline >91.3%). The other hole transporting aromatic tertiary amines used in Examples 12 and 13 are N,N,N',N'-tetra-p-tolyl-4,4'-diaminobiphenyl (ATA-7) and N,N,N',N'-tetraphenyl-4,4'-diaminobiphenyl (ATA-8) which are both deposited to a thickness of 37.5 nm. As compared with ATA-1, ATA-7 showed lower initial outputs at the same current density and ATA-7 and ATA-8 showed an output decline of 62.5% and 60%, respectively.

A combination of a triarylamine (ATA-1) and a tetraarylamine (ATA-7) is described in Example 14 and 15. This provides a low initial output at the same current density and a considerable output decline. As seen from these results, the life of these light-emitting elements is yet below the practically acceptable level. Particularly when the elements are driven with a high current density for the purpose of producing light of a high output or luminance clearing the practically acceptable level, a drastic output drop occurs during nearly initial operation.

For the purpose of improving such a drastic output drop, specific hole transporting aromatic tertiary amines are useful as disclosed in VanSlyke et al. U.S. Pat. No. 5,061,569 or JP-A 234681/1993. More particularly, the aromatic tertiary amine is comprised of at least two tertiary amine moieties and includes attached to a tertiary amine nitrogen atom an aromatic moiety having at least two fused aromatic rings. Use of these specific hole transporting aromatic tertiary amines, however, leaves it still difficult to achieve stable light emission over a long time. The light-emitting elements have a lifetime yet below the practically acceptable level.

This is because the hole transporting aromatic tertiary amines are less resistant against heat. By heat generation due to the Joule heat of an element, an amorphous thin film can become unstable. An organic EL element using such a thin film has low luminous efficiency and a short light-emitting life and remains less durable and less reliable.

The transparent electrodes used heretofore are of ITO-on-glass or the like because they must have a low surface resistivity of less than 10 to 30 Ω/cm$^2$. However, observation under a scanning tunnel microscope (STM) or atomic force microscope (AFM) indicates irregularities of the order of 20 nm on sputtered film-bearing substrates and of the order of 40 nm on EB evaporated film-bearing substrates. There is also surface roughening due to damage during ITO patterning. Therefore, the prevailing situation is likely to promote crystallization of an organic thin film.

Solutions in this respect include provision of a metal-containing or metal-free phthalocyanine film on the ITO surface (see the above-referred U.S. Pat. No. 4,720,432 or JP-A 295695/1988) and spin coating of polyarylene vinylene. However, the phthalocyanine whether or not it contains a metal is microcrystalline and is not always effective. The polyarylene vinylene can damage ITO with an acid generated upon conversion and promote oxidation of the electrodes by residual solvent or the like. A film of polyarylene vinylene is non-uniform because of spin coating. All these fail to improve element reliability.

For the purpose of improving element performance, EL elements having a mix layer consisting of a mixture of two or more compounds having distinct functions were also proposed. For example, JP-A 250292/1990 discloses that a thin film of layered structure or a mix thin film prepared from an organic compound having hole transporting and light emitting functions and another organic compound having an electron transporting function is used as a light emitting layer for the purpose of improving luminance and durability. JP-A 291696/1990 discloses to use a thin film of a mixture of an organic compound having a hole transporting function and a fluorescent organic compound having an electron transporting function as a light emitting layer. JP-A 114197/1991 discloses to interpose a mix layer of a mixture of an electric charge injecting material and an organic fluorescent material between an electric charge injecting layer and a light emitting layer for the purpose of improving luminous efficiency and luminance. JP-A 190089/1991 discloses to interpose between a hole transporting layer and/or an electron transporting layer and an organic light emitting layer a mix layer containing the components of the opposed layers for the purpose of facilitating injection of holes and electrons into the light emitting layer. JP-A 334894/1992 discloses that when a plurality of organic compound layers are formed, a layer in which compounds of distinct functions are co-present is formed, for example, a layer containing a hole transporting luminescent material and an electron transporting material is formed, thereby increasing luminance, providing a variety of emission color hues and improving durability. JP-A 182762/1993 discloses to form a mix layer of a mixture of a luminescent material a an electric charge injecting material between a light emitting layer and an electric charge injecting layer, thereby lowering the drive voltage. JP-A 289090/1991 discloses to form a thin film of a mixture of a hole conducting organic compound and an organic complex of a rare earth metal as a light emitting layer, achieving a narrow luminous spectrum, monochromaticity, and high conversion efficiency. JP-A 178487/1992 and 78655/1993 discloses high luminance full-color elements which are obtained by forming a thin film layer of a mixture of an organic charge material and an organic luminescent material as an organic luminescent thin film layer, thereby preventing concentration extinction and increasing the available range of luminescent material. Moreover, JP-A 357694/1992 discloses to for layers of graded structure in which a concentration gradient is provided between adjacent layers by components of respective layers, thereby lowering the drive voltage and improving durability.

Also organic compound layers doped with rubrene were proposed. Typical examples of known organic compound layers doped with rubrene are found in organic EL elements comprising a hole transporting layer in the form of a film of a mixture of hydrazine derivatives and a light emitting layer of tris(8-quinolinolato)aluminum as organic compound layers wherein the hole transporting layer is doped with rubrene or a half portion of the hole transporting layer disposed on the organic interface and the entire light emitting layer are doped with rubrene. It was reported that in the element having the hole transporting layer doped with rubrene, light emission takes place from both tris(8-quinolinolato) aluminum and rubrene and that in the element having a half portion of the hole transporting layer and the light emitting layer doped with rubrene, luminous efficiency is improved and the increase of dark spots during shelf storage is suppressed. See Kanai, Yajima & Sato, Extended Abstracts of the 39th Spring Meeting, 1992 of The Japan Society of Applied Physics and Related Societies, 28p-Q-8 (1992) and Sato & Kanai, Preprint of Workshop 92 of the Japanese Research Association for Organic Electronics Materials (JOEM), 31 (1992). A hole transporting layer of triphenyl-diamnie derivative (TPD) doped with rubrene was also proposed as having an improved luminance half-life. See Fujii, Sano, Fujita, Hamada & Shibata, Extended Abstracts of the 54th Autumn Meeting, 1993 of The Japan Society of Applied Physics, 29p-ZC-7 (1993).

Moreover, JP-A 207488/1990 discloses an element comprising a p-type inorganic semiconductor thin film layer and an organic compound thin film layer consisting essentially of rubrene, the element providing satisfactory luminance and stability thereof.

None of the foregoing EL elements are satisfactory in luminous life.

SUMMARY OF THE INVENTION

A primary object of the present invention is to provide an organic EL element using an organic compound in the form of a tetrolyldiamine derivative which ban a high melting point and high glass transition temperature and thus improved thermal properties, allows a thin film thereof to remain stable in an amorphous state over a long term, can form a thin film by itself without a need for a binder resin, experiences minimal physical, photo-chemical and electro-chemical changes, and has a photo-electron function.

Another object of the present invention is to provide a durable, reliable, high luiinance organic EL element having an etende emission life by using the specific compound.

A furter object of the present invention is to provide a high reliability, high luminance light emitting element featuring minimized voltage rise, current leakage, and delopmnet or growth of local dark spots during driving of the element as well as a minimized initial drop of luminance.

According to the invention, there is provided an organic electroluiminescent (EL) element or device comprising at least one layer containing at least one organic electroluminescent element-forming compound which is a tetra-aryldiamire derivative of the following formula (1).

(1)

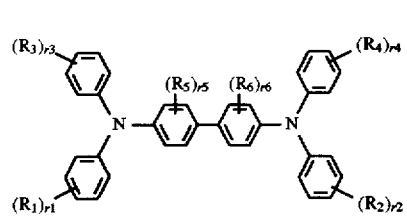

$R_1$, $R_2$, $R_3$, and $R_4$ are independently select from the group consisting of an aryl group, alkyl group, alkoxy group, aryloxy group, amino group and halogen atom, at least one of $R_1$, $R_2$, $R_3$, and $R_4$ is an aryl group; r1, r2, r3, and r4 are independently 0 or an integer of 1 to 5, the sum of r1, r2, r3, and r4 is an integer of at least 1; $R_5$ and $R_6$ are independently selected from the group consisting of an alkyl group, alkoxy group, amino group, and halogen atom; and r5 and r6 are independently 0 or an integer of 1 to 4.

Preferably, two to four of $R_1$ to $R_4$ are aryl groups, at least two of the aryl groups are attached to the corresponding benzene ring at the para- or meta-position with respect to the position of attachment to the nitrogen atom. Preferably, at least one of the aryl groups represented by $R_1$ to $R_4$ is phenyl. Preferably at least one of the aryl groups represented by $R_1$ to $R_4$ is a naphthyl, anthryl, pyrenyl, perylenyl or coronenyl group.

In one preferred embodiment, the compound has the following formula (2).

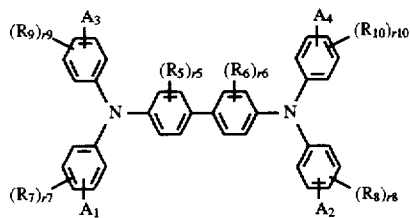

(2)

$A_1$, $A_2$, $A_3$, and $A_4$, which may be identical or different, are phenyl groups attached to the corresponding benzene ring at the para- or meta-position with respect to the position of attachment to the nitrogen atom; $R_7$, $R_8$, $R_9$, and $R_{10}$ are independently selected from the group consisting of an alkyl group, alkoxy group, aryl group, aryloxy group, amino group and halogen atom; r7, r8, r9, and r10 are independently 0 or an integer of 1 to 4; $R_5$ and $R_6$ are independently selected from the group consisting of an alkyl group, alkoxy group, amino group, and halogen atom; and r5 and r6 are independently 0 or an integer of 1 to 4.

In another preferred embodiment, the compound has the following formula (3).

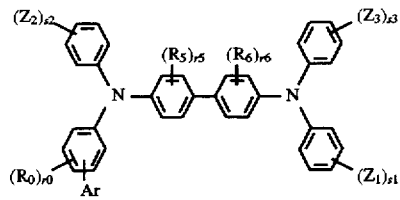

(3)

Ar is an aryl group attached to the corresponding benzene ring at the para- or meta-position with respect to the position of attachment to the-nitrogen atom; $Z_1$, $Z_2$, and $Z_3$ are independently selected from the group consisting of an alkyl group, alkoxy group, aryl group, aryloxy group, amino group and halogen atom, at least one of $Z_1$, $Z_2$, and $Z_3$ is an aryl group attached to the corresponding benzene ring at the para- or meta-position with respect to the position of attachment to the nitrogen atom, with the proviso that all of Ar, $Z_1$, $Z_2$, and $Z_3$ are not phenyl groups each attached to the corresponding benzene ring at the para- or meta-position with respect to the position of attachment to the nitrogen atom at the same time; s1, s2, and s3 are independently 0 or an integer of 1 to 5, the sum of s1, s2 and s3 is an integer of at least 1; $R_0$ is selected from the group consisting of an alkyl group, alkoxy group, aryl group, aryloxy group, amino group and halogen atom; $r_0$ is 0 or an integer of 1 to 4; $R_5$ and $R_6$ are independently selected from the group consisting of an alkyl group, alkoxy group, amino group, and halogen atom; and r5 and r6 are independently 0 or an integer of 1 to 4.

In a further preferred embodiment, the compound has the following formula (4).

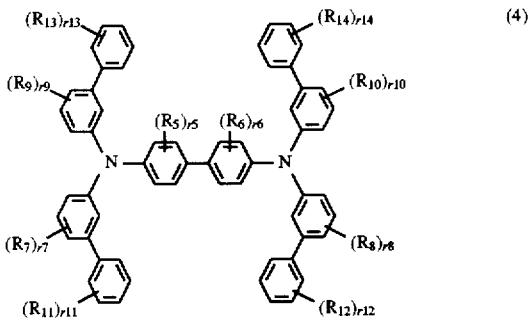

(4)

$R_7$, $R_8$, $R_9$, and $R_{10}$ are independently selected from the group consisting of an alkyl group, alkoxy group, aryl group, aryloxy group, amino group and halogen atom; r7, r8, r9, and r10 are independently 0 or an integer of 1 to 4; $R_{11}$, $R_{12}$, $R_{13}$, and $R_{14}$ are independently selected from the group consisting of an alkyl group, alkoxy group, aryl group, aryloxy group, amino group and halogen atom; r11, r12, r13, and r14 are independently 0 or an integer of 1 to 5; $R_5$ and $R_6$ are independently selected from the group Consisting of an alkyl group, alkoxy group, amino group, and halogen atom; and r5 and r6 are independently 0 or an integer of 1 to 4. More preferably r5, r6, r7, r8, r9, r10, r11, r12, r13, and r14 are equal to 0.

In a still further preferred embodiment, the compound has the following formula (5).

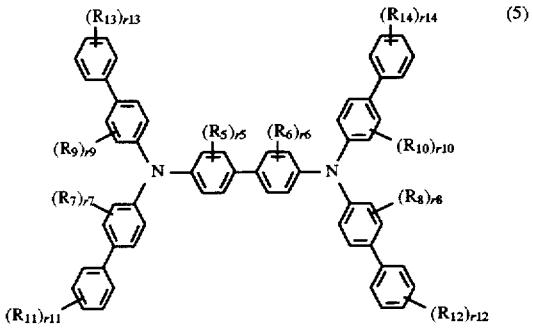

(5)

$R_5$, $R_6$, $R_7$, $R_8$, $R_9$, $R_{10}$, $R_{11}$, $R_{12}$, $R_{13}$, $R_{14}$, r5, r6, r7, r8, r9, r10, r11, r12, r13, and r14 are as defined above. More preferably, r5, r6, r7, r8, r9, r10, r11, r12, r13, and r14 are equal to 0.

In a still further preferred embodiment, the compound has the following formula (6):

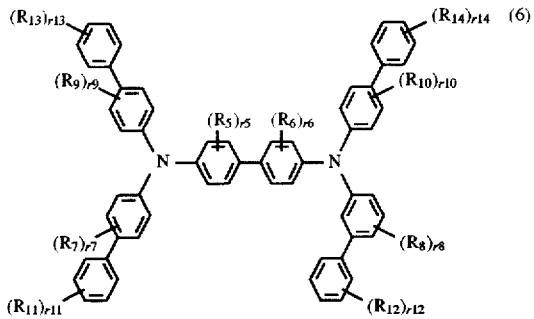

$R_5$, $R_6$, $R_7$, $R_8$, $R_9$, $R_{10}$, $R_{11}$, $R_{12}$, $R_{13}$, $R_{14}$, r5, r6, r7, r8, r9, r10, r11, r12, r13, and r14 are as defined above. More preferably, r5, r6, r7, r8, r9, r10, r11, r12, r13, and r14 are equal to 0.

In a still further preferred embodiment, the compound has the following formula (7):

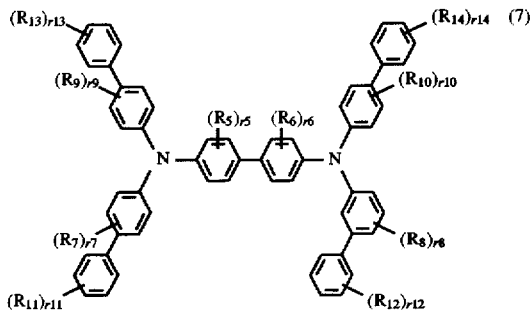

$R_5$, $R_6$, $R_7$, $R_8$, $R_9$, $R_{10}$, $R_{11}$, $R_{12}$, $R_{13}$, $R_{14}$, r5, r6, r7, r8, r9, r10, r11, r12, r13, and r14 are as defined above. More preferably, r5, r6, r7, r8, r9, r10, r11, r12, r13, and r14 are equal to 0.

In a still further preferred embodiment, the compound has the following formula (8).

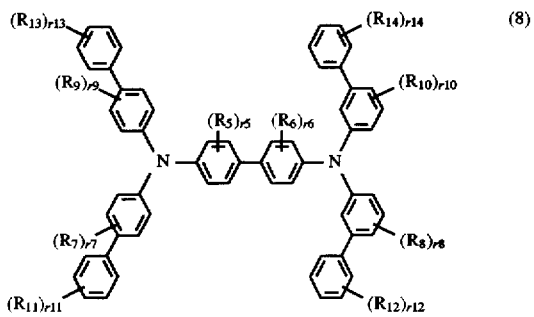

$R_5$, $R_6$, $R_7$, $R_8$, $R_9$, $R_{10}$, $R_{11}$, $R_{12}$, $R_{13}$, $R_{14}$, r5, r6, r7, r8, r9, r10, r11, r12, r13, and r14 are as defined above. More preferably, r5, r6, r7, r8, r9, r10, r11, r12, r13, and r14 are equal to 0.

In a still further preferred embodiment, the compound has the following formula (9).

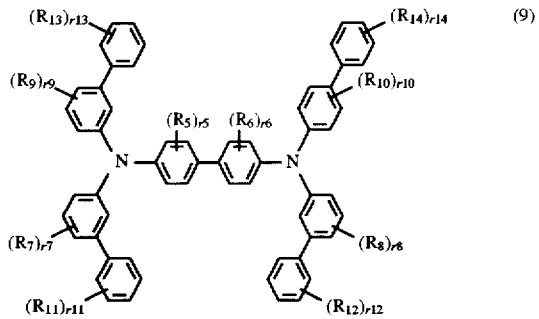

$R_5$, $R_6$, $R_7$, $R_8$, $R_9$, $R_{10}$, $R_{11}$, $R_{12}$, $R_{13}$, $R_{14}$, r5, r6, r7, r8, r9, r10, r11, r12, r13, and r14 are as defined above. More preferably, r5, r6, r7, r8, r9, r10, r11, r12, r13, and r14 are equal to 0.

In a still further preferred enbodiment, the compound has the following formula (10).

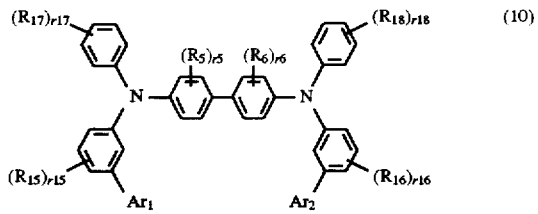

$Ar_1$ and $Ar_2$ which may be identical or different are aryl groups; $R_{15}$ and $R_{16}$ are independently selected from the group consisting of an alkyl group, alkoxy group, aryl group, aryloxy group, amino group and halogen atom; r15 and r16 are independently 0 or an integer of 1 to 4; $R_{17}$ and $R_{18}$ are independently selected from the group consisting of an alkyl group, alkoxy group, aryloxy group, amino group and halogen atom; r17 and r18 are independently 0 or an integer of 1 to 5; $R_5$ and $R_6$ are independently selected from the group consisting of an alkyl group, alkoxy group, amino group, and halogen atom; and r5 and r6 are independently 0 or an integer of 1 to 4. More preferably, r5, r6, r15, r16, r17, and r18 are equal to 0.

In a still further preferred embodiment, the compound has the following formula (11).

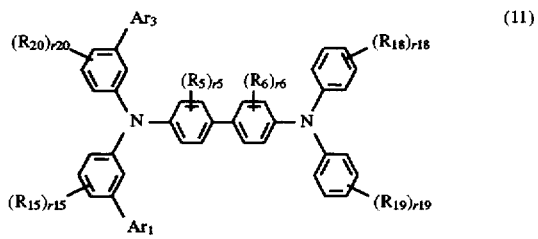

$Ar_1$ and $Ar_3$ which may be identical or different are aryl groups; $R_{15}$ and $R_{20}$ are independently selected from the group consisting of an alkyl group, alkoxy group, aryl group, aryloxy group, amino group and halogen atom; r15 and r20 are independently 0 or an integer of 1 to 4; $R_{18}$ and $R_{19}$ are independently selected from the group consisting of an alkyl group, alkoxy group, aryloxy group, amino group and halogen atom; r18 and r19 are independently 0 or an integer of 1 to 5; and $R_5$, $R_6$, r5 and r6 are as defined above. More preferably, r5, r6, r15, r18, r19, and r20 are equal to 0.

In a still further preferred embodiment, the compound has the following formula (12).

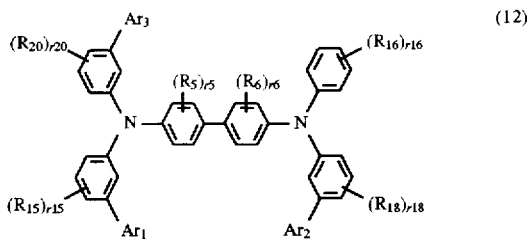

$Ar_1$, $Ar_2$, and $Ar_3$ which may be identical or different are aryl groups; $R_{15}$, $R_{16}$, and $R_{20}$ are independently selected from the group consisting of an alkyl group, alkoxy group, aryl group, aryloxy group, amino group and halogen atom; r15 r16 and r20 are independently 0 or an integer of 1 to 4; $R_{18}$ is selected from the group consisting of an alkyl group, alkoxy group, aryloxy group, amino group and halogen atom; r18 is 0 or an integer of 1 to 5; and $R_5$, $R_6$, r5 and r6 are as defined above. More preferably, r5, r6, r15, r16, r18, and r20 are equal to 0.

In a still further preferred embodiment, the compound has the following formula (13).

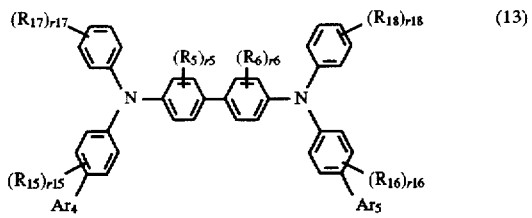

$Ar_4$ and $Ar_5$ which may be identical or different are aryl groups; $R_{15}$ and $R_{16}$ are independently selected from the group consisting of an alkyl group, alkoxy group, aryl group, aryloxy group, amino group and halogen atom; r15 and r16 are independently 0 or an integer of 1 to 4; $R_{17}$ and $R_{18}$ are independently selected from the group consisting of an alkyl group, alkoxy group, aryloxy group, amino group and halogen atom; r17 and r18 are independently 0 or an integer of 1 to 5; and $R_5$, $R_6$, r5 and r6 are as defined above. More preferably, r5, r6, r15, r16, r17, and r18 are equal to 0.

In a still further preferred embodiment, the compound has the following formula (14).

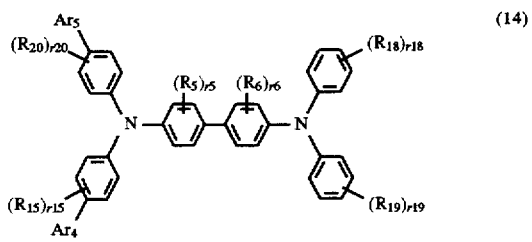

$Ar_4$ and $Ar_6$ which may be identical or different are aryl groups; $R_{15}$ and $R_{20}$ are independently selected from the group consisting of an alkyl group, alkoxy group, aryl group, aryloxy group, amino group and halogen atom; r15 and r20 are independently 0 or an integer of 1 to 4; $R_{18}$ and $R_{19}$ are independently selected from the group consisting of an alkyl group, alkoxy group, aryloxy group, amino group and halogen atom; r18 and r19 are independently 0 or an integer of 1 to 5; and $R_5$, $R_6$, r5 and r6 are as defined above. More preferably, r5, r6, r15, r18, r19, and r20 are equal to 0.

In a still further preferred embodiment, the compound has the following formula (15).

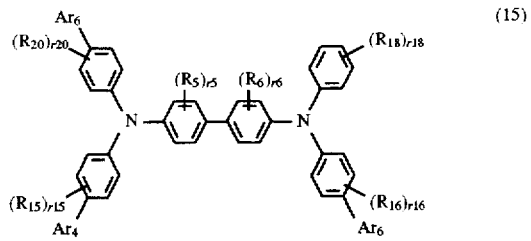

$Ar_4$, $Ar_5$, and $Ar_6$ which may be identical or different are aryl groups; $R_{15}$, $R_{16}$, and $R_{20}$ are independently selected from the group consisting of an alkyl group, alkoxy group, aryl group, aryloxy group, amino group and halogen atom; r15, r16, and r20 are independently 0 or an integer of 1 to 4; $R_{18}$ is selected from the group consisting of an alkyl group, alkoxy group, aryloxy group, amino group and halogen atom; r18 is 0 or an integer of 1 to 5; and $R_5$, $R_6$, r5 and r6 are as defined above. More preferably, r5, r6, r15, r16, r18, and r20 are equal to 0.

Preferably the organic EL element includes at least one mix layer containing a mixture of at least one organic EL element-forming compound as defined above and at least one compound having an electron injecting and transporting function. Preferably, the compound having an electron injecting and transporting function is tris(8-quinolinolato) aluminum. Preferably, the mix layer is a light emitting layer.

Preferably, at least one layer containing at least one organic EL element-forming compound is doped with a fluorescent material, typically rubrene.

Preferably, the layer containing at least one organic EL element-forming compound is a hole injecting and transporting layer and the element further includes a light emitting layer. The hole injecting and transporting layer preferably includes at least two layers having different compositions. Preferably at least one of the hole injecting and transporting layers contains a polythiophene.

Also preferably, the organic EL element further includes an electron injecting and transporting layer.

Further preferably, the layer containing at least one organic electroluminescent element-forming compound is a layer having a hole injecting and transporting function; a layer having a light emitting function or electron injecting and transporting function is disposed adjacent the layer; and the difference in ionization potential Ip between the layer having a hole injecting and transporting function and the layer having a light emitting function or electron injecting and transporting function is at least 0.25 eV.

BENEFITS OF THE INVENTION

The compounds for use in organic EL elements according to the invention are tetraaryldiamine derivatives of formula (1) having a high melting point and a high glass transition temperature (Tg). Thin films formed from these compounds as by evaporation are of quality in that they are transparent, keep a stable amorphous state at room temperature or higher, and maintain a smooth surface film of quality over an extended period of time. Therefore, the compounds can be formed into thin films by themselves without a need for binder resins.

These advantages are derived from the following facts. 1) The compound is increased in molecular weight so as to have a higher melting point. 2) A bulky substituent providing steric hindrance such as a phenyl group is introduced to optimize intermolecular overlap. 3) The number of conformations that the molecule can assume is increased to restrain rearrangement of the molecule.

Further due to inclusion of many hole injecting and transporting units such as N-phemyl groups and introduction of phenyl groups in $R_1$ to $R_4$ to form biphenyl groups, there is available an expanded $\pi$-conjugated system which is advantageous for carrier transportation. This results in a significantly improved hole injecting and transporting capability.

Since the organic EL element of the invention uses a tetraaryldiamine derivative of formula (1) as an organic EL element-forming compound in an organic compound layer, typically a hole injecting and transporting layer, the element ensures uniform plane light emission and maintains high luminance over a long period of time in a stable manner. The element maintains emission at a high luminance of about 100 to 100,000 $cd/m^2$ or even higher over a long period of time in a stable manner though the luminance depends on the wavelength of emitted radiation. It is to be noted that the organic EL elements of the invention emit light at a maximum wavelength in the range of about 350 to 700 nm. Heat resistance and durability are high enough to allow for stable operation of the element even at a current density as high as about 1 $A/cm^2$ or more.

In an embodiment wherein the inventive compound is used in an organic compound layer of an organic EL element, the energy level is optimized and carriers are effectively blocked at the interface, ensuring stable carrier recombination and light emission. Especially when the inventive compound is used in a hole injecting and transporting layer of an organic EL element, the difference in ionization potential Ip between the hole injecting and transporting layer and a layer disposed adjacent thereto and having a light emitting or luminescent function (inclusive of a light emitting layer also serving as an electron injecting and transporting layer, that is, light emitting/electron injecting and transporting layer) or between the hole injecting and transporting layer and an electron injecting and transporting layer disposed adjacent thereto (where the hole injecting and transporting layer is a layer having a hole injecting and transporting function and also serving as a light emitting layer) is optimized. Then the carrier blocking effect at the interface is enhanced and injection of polarly inferior or unstable carriers is less probable. The organic compounds in the respective layers are less susceptible to damage and few points of deactivation of carriers or excitons are created in the carrier recombination region or light emitting region. This results in stable light emission and a significantly extended life.

In an embodiment wherein an organic compound layer containing a mixture of the inventive compound and a compound having an electron injecting and transporting function is provided, typically as a light emitting layer, carrier hopping conduction paths are created in the mix layer, allowing carriers injected into the mix layer to move through a polarly predominant material. More particularly, holes move through a hole injecting and transporting material and electrons move through an electron injecting and transporting material while injection of carriers of opposite polarity is rather inhibited. The respective organic compounds are less susceptible to damage. As a result, the EL element has a substantially extended life.

In an embodiment wherein an organic compound layer containing the inventive compound is doped with a fluorescent material, by using the inventive compound in a hole injecting and transporting layer of an organic EL element, the difference in ionization potential Ip between the hole injecting and transporting layer and a layer disposed adjacent thereto and having a light emitting function (inclusive of a light emitting layer also serving as an electron injecting and transporting layer, that is, light emitting/electron injecting and transporting layer) or between the hole injecting and transporting layer and an electron injecting and transporting layer disposed adjacent thereto (where the hole injecting and transporting layer is a layer having a hole injecting and transporting function and also serving as a light emitting layer) is optimized. Then the carrier blocking effect at the interface is enhanced and injection of polarly inferior or unstable carriers is less probable. The organic compounds in the respective layers are less susceptible to damage and few points of deactivation of carriers or excitons are created in the carrier recombination region or light emitting region. Where the organic compound layer is additionally doped with a fluorescent material in the form of rubrene, which has a bipolar transporting ability and allows for carrier recombination, the damage to the organic compound is accordingly reduced. Further, since rubrene is present in proximity to the carrier recombination region, energy transfer from excitons to rubrene takes place to reduce non-radiative deactivation, resulting in stable light emission and a significantly extended life.

BRIEF DESCRIPTION OF THE DRAWINGS

The foregoing aspects and other features of the invention are explained in the following description, taken in connection with the accompanying drawings where.

DETAILED DESCRIPTION TO THE INVENTION

Figure 1:
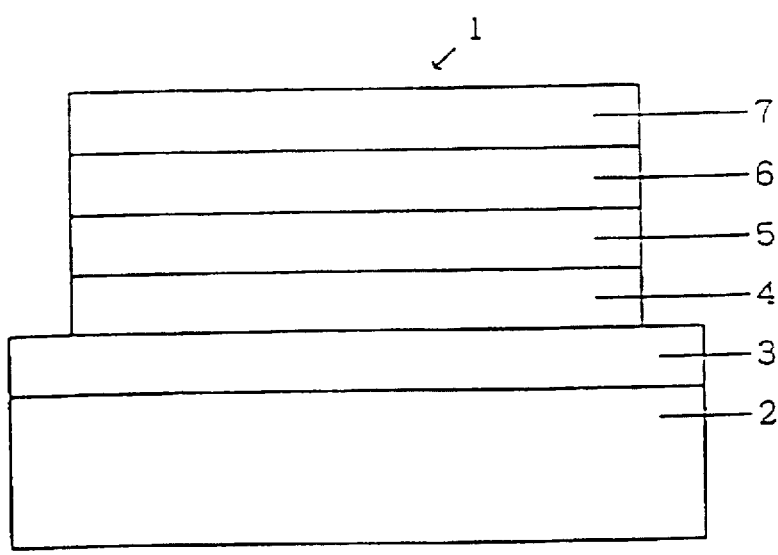
FIG. 1 is a side elevation of an exemplary organic EL element according to one embodiment of the invention.

The compound for use in an organic EL element according to the invention, which is often referred to as "inventive compound" throughout the specification, is a tetraaryldiamine derivative of formula (1).

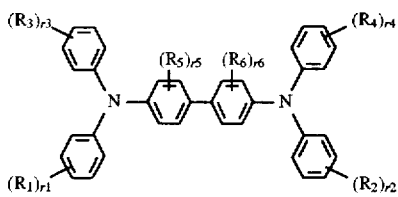

(1)

In a formula (1), $R_1$, $R_2$, $R_3$, and $R_4$ independently represent an aryl group, alkyl group, alkoxy group, aryloxy group, amino group or halogen atom. They may be identical or different. At least one of $R_1$, $R_2$, $R_3$, and $R_4$ groups is an aryl group. Letters r1, r2, r3, and r4 are independently 0 or an integer of 1 to 5. All of r1, r2, r3, and r4 are not equal to 0 at the same time, therefore, the sum of r1+ r2+r3+r4 is an integer of 1 or more which satisfies the requirement that at least one aryl group is present. $R_5$ and $R_6$ independently represent an alkyl group, alkoxy group, amino group or halogen atom. They may be identical or different. Letters r5 and r6 are independently 0 or an integer of 1 to 4.

The aryl group represented by $R_1$ to $R_4$ may be either monocyclic or polycyclic and inclusive of a fused ring and gathered rings. The aryl group preferably has 6 to 20 carbon atoms in total and may have a substituent. Exemplary substituents are alkyl, alkoxy, aryl, aryloxy, amino groups, and halogen atoms. Illustrative examples of the aryl group represented by $R_1$ to $R_4$ include phenyl, o-, m- and p-tolyl, pyrenyl, naphthyl, anthryl, biphenyl, phenylanthryl, and tolylanthryl groups, with the phenyl group being preferred. The aryl group, especially phenyl group is preferably attached to the 3- or 4-position (meta- or para-position) of the benzene ring with respect to the position of attachment to the nitrogen atom.

The alkyl group represented by $R_1$ to $R_4$ may be either normal or branched. The alkyl group preferably has 1 to 10 carbon atoms and may have a substituent. Exemplary substituents are the same as described above in conjunction with the aryl group. Illustrative examples of the alkyl group represented by $R_1$ to $R_4$ include methyl, ethyl, n- and i-propyl, and n-, i-, s- and t-butyl groups.

The alkoxy group represented by $R_1$ to $R_4$ is preferably one in which the alkyl moiety has 1 to 6 carbon atoms. It may have a substituent. Illustrative examples of the alkoxy group represented by $R_1$ to $R_4$ include methoxy, ethoxy, and t-butoxy groups.

Examples of the aryloxy group represented by $R_1$ to $R_4$ include phenoxy, 4-methylphenoxy, and 4-(t-butyl)phenoxy groups The amino group represented by $R_1$ to $R_4$ may be either substituted or unsubstituted, preferably substituted. Exemplary are dimethylamino, diethylamino, diphenylamino, bis(biphenyl)amino, N-phenyl-N-tolylamino, N-phenyl-N-biphenylamino, bis(naphthylamino), bis(anthryl)amino, and bis(pyrenyl)amino groups.

Exemplary of the halogen atom represented by $R_1$ to $R_4$ are chlorine and bromine atoms.

At least one of $R_1$ to $R_4$ is an aryl group. Preferably two to four aryl groups are present in a molecule as $R_1$ to $R_4$, and two to four of r1 to r4 age preferably integers of at least 1. Further preferably, two to four aryl groups in total are present in a molecule, more preferably two to four of r1 to r4 are equal to 1, especially r1 to r4 being equal to 1. Most preferably all of $R_1$ to $R_4$ included are aryl groups. More particularly, on the four benzene rings which may have $R_1$ to $R_4$ substituents in a molecule, there may be present two to four aryl groups in total. The benzene ring to which two to four aryl groups are attached may be identical or different among the four benzene rings although it is preferred that two to four aryl groups are individually attached to different benzene rings. It is more preferred that at least two aryl groups are attached to the corresponding benzene rings at their para- or meta-position with respect to the position of attachment to the nitrogen atom. It is preferred that among the aryl groups, at least one is a phenyl group, that is, an aryl group and the benzene ring, taken together, form a 4- or 3-biphenylyl group with respect to the nitrogen atom. Especially, two to four 4- or 3-biphenylyl groups are included. In this case, either one or both of 4- and 3-biphenylyl groups may be present. Preferred aryl groups other than phenyl include 1-or 2-naphthyl, 1-, 2- or 9-anthryl, pyrenyl, perylenyl, and coronenyl groups. Also preferably, aryl groups other than phenyl are attached to the corresponding benzene rings at their para- or meta-position with respect to the position of attachment to the nitrogen atom. A mixture of phenyl and other aryl groups is also acceptable.

In formula (1), $R_5$ and $R_6$ represent an alkyl group, alkoxy group, amino group or halogen atom, examples of which are the same as described for $R_1$ to $R_4$. Although letters r5 and r6 are independently 0 or an integer of 1 to 4, it is preferred that both r5 and r6 be equal to 0. It is preferred that the biphenylene group connecting the two arylamino groups be unsubstituted.

Where r1 to r4 are integers of at least 2, the groups represented by each of $R_1$ to $R_4$ may be identical or different. Similarly, where r5 and r6 are integers of at least 2, the groups represented by each of $R_5$ and $R_6$ may be identical or different.

Preferred among the compound of formula (1) are compounds of formulae (2) and (3).

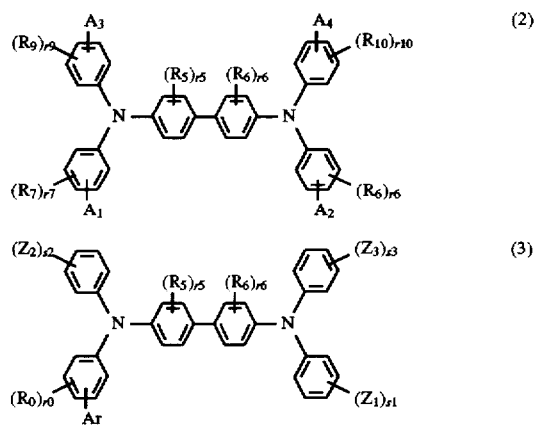

Formula (2) is first described. In formula (2), $A_1$, $A_2$, $A_3$, and $A_4$, which may be identical or different, are phenyl groups attached to the corresponding benzene rings at their para- or meta-position (4- or 3-position) with respect to the position of attachment to the nitrogen atom. These phenyl groups may be substituted or unsubstituted, with the preferred substituents being the same as described for the aryl group represented by $R_1$ to $R_4$.

$R_7$ to $R_{10}$ independently represent an alkyl group, alkoxy group, aryl group, aryloxy group, amino group or halogen atom, they may be identical or different. Illustrative examples of these groups are the same as described for $R_1$ to $R_4$ of formula (1).

Letters r7 to r10 are independently 0 or an integer of 1 to 4. Preferably r7 to r10 are equal to 0.

$R_5$, $R_6$, r5 and r6 are as defined for formula (1), with r5=r6=0 being preferred.

Where r7 to r10 are integers of at least 2, the groups represented by each of $R_7$ to $R10$ may be identical or different.

Next formula (3) is described. In formula (3), Ar is an aryl group attached to the corresponding benzene ring at its para- or meta-position with respect to the position of attachment to the nitrogen atom. Exemplary aryl groups are the same as the aryl group represented by $R_1$ to $R_4$ in formula (1). The aryl group may be substituted or unsubstituted, with the preferred substituents being the same as described for the aryl group represented by $R_1$ to $R_4$. An amino group is a preferred substituent. It is noted that the amino group may be cyclized to form a heterocyclic ring. Exemplary amino groups are those amino groups described in conjunction with $R_1$ to $R_4$.

$Z_1$, $Z_2$, and $Z_3$ independently represent an alkyl group, alkoxy group, aryl group, aryloxy group, amino group or halogen atom. Examples of these groups are the same as previously described in conjunction with $R_1$ to $R_4$ in formula (1). At least one of $Z_1$, $Z_2$, and $Z_3$ is an aryl group attached to the corresponding benzene ring at the para- or meta-position with respect to the position of attachment to the nitrogen atom. It is to be noted that, all of Ar, $Z_1$, $Z_2$, and $Z_3$ are not phenyl groups each attached to the corresponding benzene ring at the para- or meta-position with respect to the position of attachment to the nitrogen atom at the same time. It is preferred that two to three of the four benzene rings each have an aryl group at the para-or meta-position. It is thus preferred that one or two of $Z_1$ to $Z_3$ groups are such aryl groups. Preferred aryl groups include 1- and 2-naphthyl, 1-, 2- and 9-anthryl, pyrenyl, perylenyl and coronenyl groups, with phenyl being most preferred. The aryl groups represented by $Z_1$ to $Z_3$ may be substitute or unsubstituted, with the preferred substituents being the same as described for the aryl group represented by $R_1$ to $R_4$. An amino group is a preferred substituent. Exemplary amino groups are those amino groups described in conjunction with $R_1$ to $R_4$.

Letters s1, s2, and s3 are independently 0 or an integer of 1 to 5. They are not equal to 0 at the same time, that is, the sum of s1, s2 and s3 is an integer of at least 1. Preferably s1, to s3 are respectively 0 or 1, more preferably one or two of $s_1$ to 63 are equal to 1 and the remainings are 0. $Z_1$ to $z_3$ included when s1 to s3 are equal to 1 are preferably aryl groups, especially phenyl groups attached to the corresponding benzene rings at their para- or meta-position with respect to the position of attachment to the nitrogen atom. Where s1 to s3 in formula (3) are integers of at least 2, the respective $Z_1$, to $Z_3$ groups may be identical or different.

In formula (3), $R_0$ and r0 are as defined for $R_7$ and r7 in formula (2), respectively. $R_5$, $R_6$, r5 and r6 are as defined in formula (2), with their preferred examples and ranges being also the same.

Most preferred among the compound of formula (2) are compounds of formulae (4) to (9).

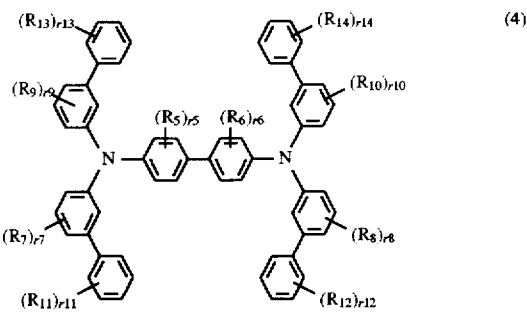

(4)

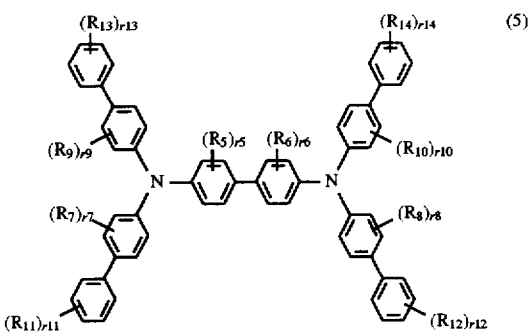

(5)

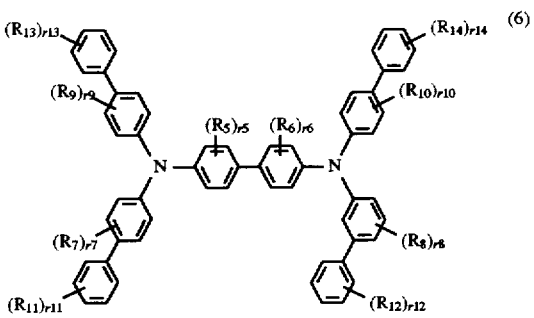

(6)

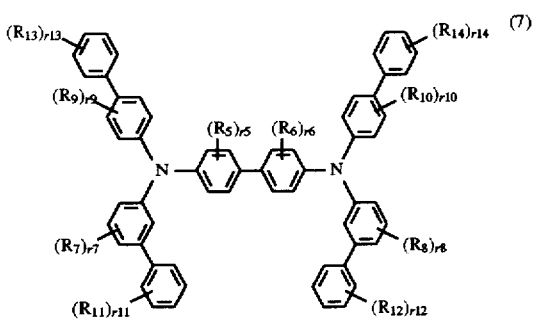

(7)

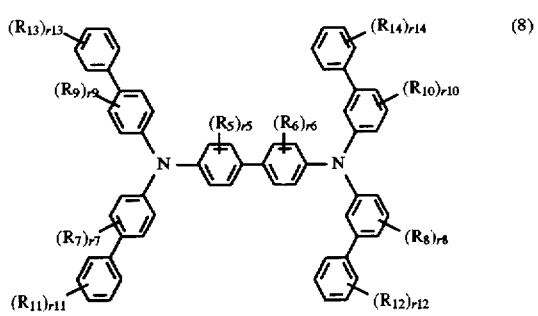

(8)

-continued

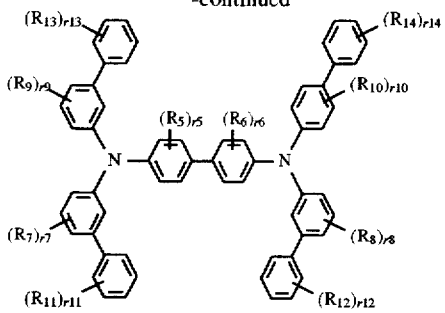
(9)

In these formulae, $R_{11}$ to $R_{14}$ independently represent an alkyl group, alkoxy group, aryl group, aryloxy group, amino group or halogen atom. They may be identical or different. Illustrative examples of these groups are the same as described for $R_1$ to $R_4$ of formula (1)

Letters r11 to r14 are independently 0 or an integer of 1 to 5. It is preferred in all formulae (4) to (9) that r11 to r14 be equal to 0. Where r11 to r14 are integers of at least 2, the groups represented by each of $R_{11}$ to $R_{14}$ may be identical or different.

In formulae (4) to (9), $R_5$ to $R_{10}$ and r5 to r10 are as defined in formula (2), with their preferred examples And ranges being also the same.

Most preferred among the compound of formula (3) are compounds of formulae (10) to (15).

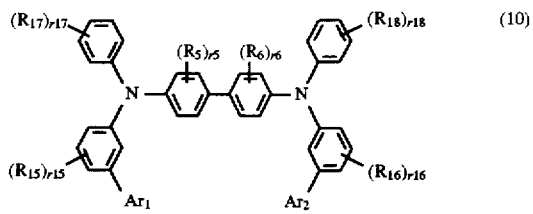
(10)

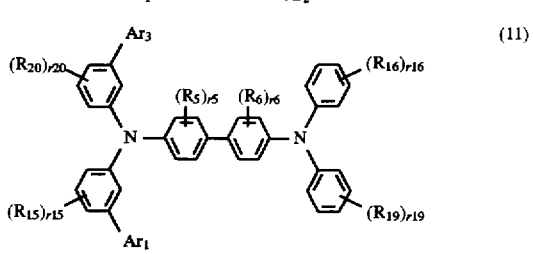
(11)

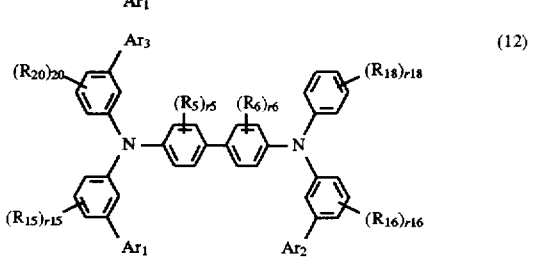
(12)

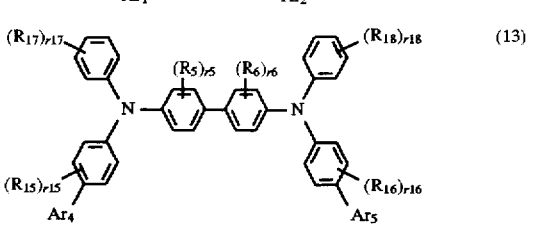
(13)

-continued

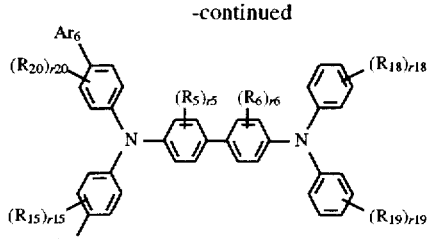
(14)

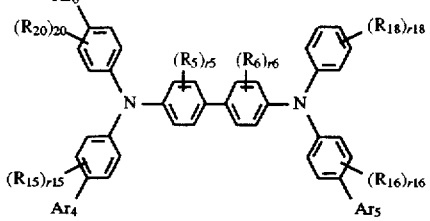
(15)

In these formulae, $Ar_1$ to $Ar_6$ are aryl groups. $Ar_1$ and $Ar_2$ in formula (10), $Ar_1$ and $Ar_3$ in formula (11), $Ar_1$, $Ar_2$ and $Ar_3$ in formula (12), $Ar_4$ and $Ar_5$ in formula (13), $Ar_4$ and $Ar_6$ in formula (14), and $Ar_4$, $Ar_5$ and $Ar_6$ in formula (15) may be identical or different. Illustrative examples of the aryl group are the same as described for $R_1$ to $R_4$ of formula (1), with the phenyl group being especially preferred.

$R_{15}$ in formulae (10) to (15), $R_{16}$ in formulae (10), (12), (13) and (15), and $R_{20}$ in formulae (11), (12), (14) and (15) independently represent an alkyl group, alkoxy group, aryl group, aryloxy group, amino group or halogen atom. $R_{15}$ and $R_{16}$ in formula (10) or (13), $R_{15}$ and $R_{20}$ in formula (11) or (14), and $R_{15}$, R16 and $R_{20}$ in formula (12) or (15) may be identical or different. Illustrative examples of these groups are the same as described for $R_1$ to $R_4$ of formula (1).

Letters r15 in formulae (10) to (15), r16 in formulae (10), (12), (13) and (15), and r20 in formulae (11), (12), (14) and (15) are independently 0 or an integer of 1 to 4, with r15=r16=r20=0 being preferred.

$R_{17}$ in formulae (10) and (13), $R_{18}$ in formulae (10) to (15), and $R_{19}$ in formulae (11) and (14) independently represent an alkyl group, alkoxy group, aryloxy group, amino group or halogen atom. $R_{17}$ and $R_{18}$ in formula (10) or (13) and R18 and R19 in formula (11) or (14) may be identical or different. Illustrative examples of these groups are the same as described for $R_1$ to $R_4$ of formula (1).

Letters r17 in formulae (10) and (13), r18 in formulae (10) to (15), and r19 in formulae (11) and (14) are independently 0 or an integer of 1 to 5, with r17=r18=r19=0 being preferred.

In formulae (10) to (15), where r15, r16 and r20 are integers of at least 2, the groups represented by each of $R_{15}$, $R_{16}$ and $R_{20}$ may be identical or different and where r17, r18 and r19 are integers of at least 2, the groups represented by each of R17, $R_{18}$ and $R_{19}$ may be identical or different.

In formulae (10) to (15), $R_5$, $R_6$, r5 and r6 are as defined for formula (1), with r5=r6=0 being preferred.

Illustrative, non-limiting examples of the compound of formula (1) are given below. Formulae (16) through (27) are general formulae. Tables 1 through 12 show combinations of R groups an formulae (16) through (27), respectively. In these Tables, except for $Ar_1$ to $Ar_6$, where all R groups under the same heading are hydrogen atoms, it is shown simply by H. Where there is a substituent, only the substituent is shown, indicating that the remaining are hydrogen atoms.

TABLE 1

(Structure (16): a tetraaryl biphenyl diamine with substituents $R^1$–$R^{44}$ on the various phenyl rings, with two diarylamino groups on a central biphenyl, each N bearing two biphenyl substituents.)

| Compound No. | $R^1$–$R^4$ | $R^5$–$R^9$ | $R^{10}$–$R^{13}$ | $R^{14}$–$R^{18}$ |
|---|---|---|---|---|
| I-1 | H | H | H | H |
| I-2 | H | $R^6 = CH_3$ | H | $R^{17} = CH_3$ |
| I-3 | H | $R^7 = CH_3$ | H | $R^{16} = CH_3$ |
| I-4 | H | $R^7 = t\text{-}C_4H_9$ | H | $R^{16} = t\text{-}C_4H_9$ |
| I-5 | H | $R^7 = OCH_3$ | H | $R^{16} = OCH_3$ |
| I-6 | H | $R^7 = Ph$ | H | $R^{16} = Ph$ |
| I-7 | H | $R^7 = $ —C$_6$H$_4$—CH$_3$ (p-tolyl) | H | $R^{16} = $ —C$_6$H$_4$—CH$_3$ (p-tolyl) |
| I-8 | H | $R^7 = OPh$ | H | $R^{16} = OPh$ |
| I-9 | H | $R^7 = N(C_2H_5)_2$ | H | $R^{16} = N(C_2H_5)_2$ |
| I-10 | H | $R^7 = N(Ph)_2$ | H | $R^{16} = N(Ph)_2$ |
| I-11 | H | $R^7 = Cl$ | H | $R^{16} = Cl$ |
| I-12 | $R^2 = CH_3$ | H | $R^{11} = CH_3$ | H |
| I-13 | $R^2 = OCH_3$ | H | $R^{11} = OCH_3$ | H |
| I-14 | $R^2 = Ph$ | H | $R^{11} = Ph$ | H |
| I-15 | $R^2 = OPh$ | H | $R^{11} = OPh$ | H |
| I-16 | $R^2 = N(C_2H_5)_2$ | H | $R^{11} = N(C_2H_5)_2$ | H |
| I-17 | $R^2 = Cl$ | H | $R^{11} = Cl$ | H |
| I-18 | H | H | H | H |
| I-19 | H | H | H | H |
| I-20 | H | H | H | H |
| I-21 | H | H | H | H |
| I-22 | H | H | H | H |
| I-23 | $R^2 = Ph$ | $R^7 = Ph$ | $R^{11} = Ph$ | $R^{16} = Ph$ |
| I-24 | $R^2 = N(Ph)_2$ | H | $R^{11} = Ph$ | H |
| I-25 | H | $R^6 = CH_3$ | H | $R^{16} = CH_3$ |
| I-26 | H | $R^6 = R^8 = CH_3$ | H | H |
| I-27 | H | $R^6 = R^8 = CH_3$ | H | H |
| I-28 | H | $R^7 = N(Ph)_2$ | H | $R^{16} = N(Ph)_2$ |
| I-29 | H | $R^6 = N(Ph)_2$ | H | $R^{17} = N(Ph)_2$ |
| I-30 | H | $R^7 = N(\text{-C}_6H_4\text{-C}_6H_5)_2$ (di(3-biphenylyl)amino) | H | $R^{16} = N(\text{-C}_6H_4\text{-C}_6H_5)_2$ |

TABLE 1-continued

| | | | | |
|---|---|---|---|---|
| I-31 | H | $R^6 = N(\text{3-biphenylyl})_2$ | H | $R^{17} = N(\text{3-biphenylyl})_2$ |
| I-32 | H | $R^7 = N(\text{3-tolyl})_2$ | H | $R^{16} = N(\text{3-tolyl})_2$ |
| I-33 | H | $R^6 = \text{Ph}$ | H | $R^{17} = \text{Ph}$ |
| I-34 | H | $R^7 = N(\text{Ph})_2$ | H | H |
| I-35 | H | $R^6 = N(\text{Ph})_2$ | H | H |
| I-36 | H | $R^7 = N(\text{4-biphenylyl})_2$ | H | $R^{16} = N(\text{4-biphenylyl})_2$ |
| I-37 | H | $R^6 = N(\text{4-biphenylyl})_2$ | H | $R^{17} = N(\text{4-biphenylyl})_2$ |
| I-38 | H | $R^7 = N(\text{4-tolyl})(\text{Ph})$ | H | $R^{16} = N(\text{4-tolyl})(\text{Ph})$ |
| I-39 | H | $R^6 = N(\text{4-tolyl})(\text{Ph})$ | H | $R^{17} = N(\text{4-tolyl})(\text{Ph})$ |
| I-40 | H | $R^7 = N(\text{4-biphenylyl})(\text{Ph})$ | H | $R^{16} = N(\text{4-biphenylyl})(\text{Ph})$ |

TABLE 1-continued
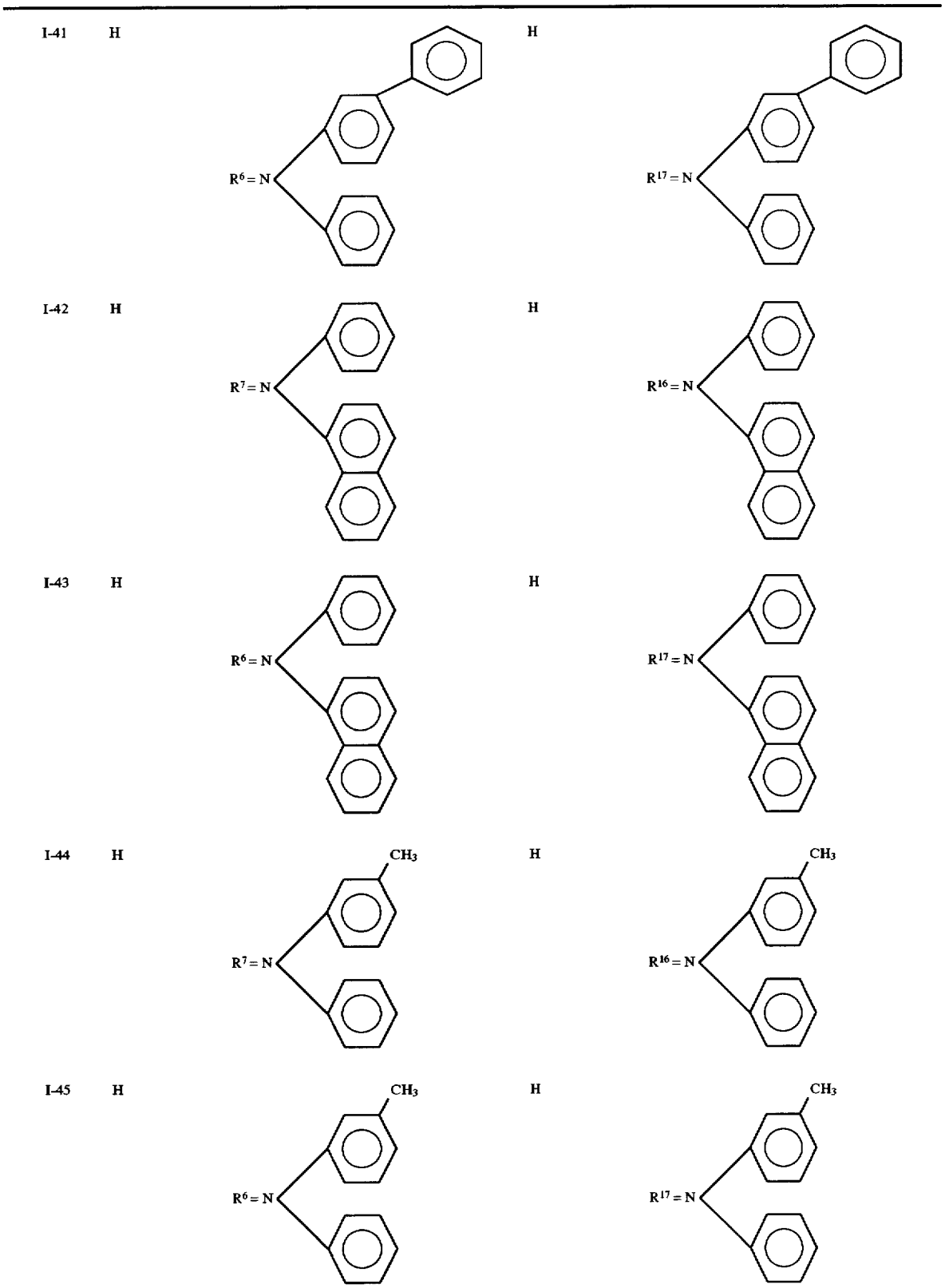

TABLE 1-continued

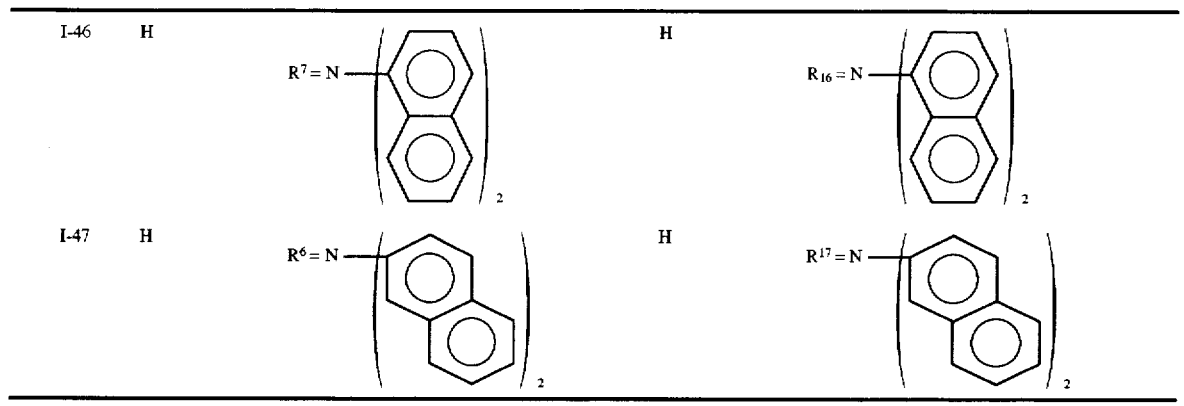

| Compound No. | $R^{19}$~$R^{22}$ | $R^{23}$~$R^{27}$ | $R^{28}$~$R^{31}$ | $R^{32}$~$R^{36}$ | $R^{37}$~$R^{44}$ |
|---|---|---|---|---|---|
| I-1 | H | H | H | H | H |
| I-2 | H | $R^{26} = CH_3$ | H | $R^{35} = CH_3$ | H |
| I-3 | H | $R^{25} = CH_3$ | H | $R^{34} = CH_3$ | H |
| I-4 | H | $R^{25} = t\text{-}C_4H_9$ | H | $R^{34} = t\text{-}C_4H_9$ | H |
| I-5 | H | $R^{25} = OCH_3$ | H | $R^{34} = OCH_3$ | H |
| I-6 | H | $R^{25} = Ph$ | H | $R^{34} = Ph$ | H |
| I-7 | H | $R^{25} = \text{—}\bigcirc\text{—}CH_3$ | H | $R^{34} = \text{—}\bigcirc\text{—}CH_3$ | H |
| I-8 | H | $R^{25} = OPh$ | H | $R^{34} = OPh$ | H |
| I-9 | H | $R^{25} = N(C_2H_5)_2$ | H | $R^{34} = N(C_2H_5)_2$ | H |
| I-10 | H | $R^{25} = N(Ph)_2$ | H | $R^{34} = N(Ph)_2$ | H |
| I-11 | H | $R^{25} = Cl$ | H | $R^{34} = Cl$ | H |
| I-12 | $R^{20} = CH_3$ | H | $R^{29} = CH_3$ | H | H |
| I-13 | $R^{20} = OCH_3$ | H | $R^{29} = OCH_3$ | H | H |
| I-14 | $R^{20} = Ph$ | H | $R^{29} = Ph$ | H | H |
| I-15 | $R^{20} = OPh$ | H | $R^{29} = OPh$ | H | H |
| I-16 | $R^{20} = N(C_2H_5)_2$ | H | $R^{29} = N(C_2H_5)_2$ | H | H |
| I-17 | $R^{20} = Cl$ | H | $R^{29} = Cl$ | H | H |
| I-18 | H | H | H | H | $R^{37} = R^{42} = CH_3$ |
| I-19 | H | H | H | H | $R^{38} = R^{43} = OCH_3$ |
| I-20 | H | H | H | H | $R^{38} = R^{43} = N(CH_3)_2$ |
| I-21 | H | H | H | H | $R^{38} = R^{43} = Cl$ |
| I-22 | H | H | H | H | $R^{40} = R^{43} = CH_3$ |
| I-23 | $R^{20} = Ph$ | $R^{25} = Ph$ | $R^{29} = Ph$ | $R^{34} = Ph$ | H |
| I-24 | $R^{20} = Ph$ | H | $R^{29} = Ph$ | H | H |
| I-25 | H | $R^{26} = CH_3$ | H | $R^{34} = CH_3$ | H |
| I-26 | H | $R^{24} = R^{26} = CH_3$ | H | H | H |
| I-27 | H | H | H | $R^{34} = R^{36} = CH_3$ | H |
| I-28 | H | H | H | H | H |
| I-29 | H | H | H | H | H |
| I-30 | H | H | H | H | H |
| I-31 | H | H | H | H | H |
| I-32 | H | H | H | H | H |
| I-33 | H | $R^{26} = Ph$ | H | $R^{35} = Ph$ | H |
| I-34 | H | $R^{25} = N(Ph)_2$ | H | H | H |
| I-35 | H | $R^{26} = N(Ph)_2$ | H | H | H |
| I-36 | H | H | H | H | H |
| I-37 | H | H | H | H | H |
| I-38 | H | H | H | H | H |
| I-39 | H | H | H | H | H |
| I-40 | H | H | H | H | H |
| I-41 | H | H | H | H | H |
| I-42 | H | H | H | H | H |
| I-43 | H | H | H | H | H |
| I-44 | H | H | H | H | H |
| I-45 | H | H | H | H | H |
| I-46 | H | H | H | H | H |
| I-47 | H | H | H | H | H |

TABLE 2

(17)

[Structure: Tetraaryl benzidine-type compound with substituents R37-R44 on central biphenyl, R51-R59 and R69-R77 on left aryl groups, R60-R68 and R78-R86 on right aryl groups]

| Compound No. | R⁵¹–R⁵⁴ | R⁵⁵–R⁵⁹ | R⁶⁰–R⁶³ | R⁶⁴–R⁶⁸ |
|---|---|---|---|---|
| II-1 | H | H | H | H |
| II-2 | H | R⁵⁶ = CH₃ | H | R⁶⁵ = CH₃ |
| II-3 | H | R⁵⁷ = CH₃ | H | R⁶⁶ = CH₃ |
| II-4 | H | R⁵⁷ = t-C₄H₉ | H | R⁶⁶ = t-C₄H₉ |
| II-5 | H | R⁵⁷ = OCH₃ | H | R⁶⁶ = OCH₃ |
| II-6 | H | R⁵⁷ = Ph | H | R⁶⁶ = Ph |
| II-7 | H | R⁵⁷ = –C₆H₄–CH₃ (para) | H | R⁶⁶ = –C₆H₄–CH₃ (para) |
| II-8 | H | R⁵⁷ = OPh | H | R⁶⁶ = OPh |
| II-9 | H | R⁵⁷ = N(C₂H₅)₂ | H | R⁶⁶ = N(C₂H₅)₂ |
| II-10 | H | R⁵⁷ = N(Ph)₂ | H | R⁶⁶ = N(Ph)₂ |
| II-11 | H | R⁵⁷ = Cl | H | R⁶⁶ = Cl |
| II-12 | H | R⁵⁷ = –C₆H₄–CH₃ (meta) | H | R⁶⁶ = –C₆H₄–CH₃ (meta) |
| II-13 | R⁵² = CH₃ | H | R⁶² = CH₃ | H |
| II-14 | R⁵² = OCH₃ | H | R⁶² = OCH₃ | H |
| II-15 | R⁵² = Ph | H | R⁶² = Ph | H |
| II-16 | R⁵² = OPh | H | R⁶² = OPh | H |
| II-17 | R⁵² = N(C₂H₅)₂ | H | R⁶² = N(C₂H₅)₂ | H |
| II-18 | R⁵² = Cl | H | R⁶² = Cl | H |
| II-19 | H | H | H | H |
| II-20 | H | H | H | H |
| II-21 | H | H | H | H |
| II-22 | H | H | H | H |
| II-23 | H | H | H | H |
| II-24 | H | R⁵⁷ = CH₃ | H | R⁶⁵ = CH₃ |
| II-25 | H | R⁵⁶ = R⁵⁸ = CH₃ | H | H |
| II-26 | H | R⁵⁷ = CH₃ | H | R⁶⁶ = CH₃ |
| II-27 | H | R⁵⁶ = R⁵⁸ = CH₃ | H | R⁶⁵ = R⁶⁷ = CH₃ |
| II-28 | H | R⁵⁷ = N(Ph)₂ | H | R⁶⁶ = N(Ph)₂ |

TABLE 2-continued

| | | | | |
|---|---|---|---|---|
| II-29 | H | $R^{57} = N(\text{3-biphenyl})_2$ | H | $R^{66} = N(\text{3-biphenyl})_2$ |
| II-30 | H | $R^{57} = N(\text{4-biphenyl})_2$ | H | $R^{66} = N(\text{4-biphenyl})_2$ |
| II-31 | H | $R^{58} = N(Ph)_2$ | H | $R^{65} = N(Ph)_2$ |
| II-32 | H | $R^{58} = N(\text{3-biphenyl})_2$ | H | $R^{65} = N(\text{3-biphenyl})_2$ |
| II-33 | H | $R^{58} = N(\text{4-biphenyl})_2$ | H | $R^{65} = N(\text{4-biphenyl})_2$ |
| II-34 | H | $R^{57} = N(\text{4-tolyl})(Ph)$ | H | $R^{66} = N(\text{4-tolyl})(Ph)$ |
| II-35 | H | $R^{58} = N(\text{4-tolyl})(Ph)$ | H | $R^{65} = N(\text{4-tolyl})(Ph)$ |
| II-36 | H | $R^{57} = N(\text{3-tolyl})(Ph)$ | H | $R^{66} = N(\text{3-tolyl})(Ph)$ |

TABLE 2-continued
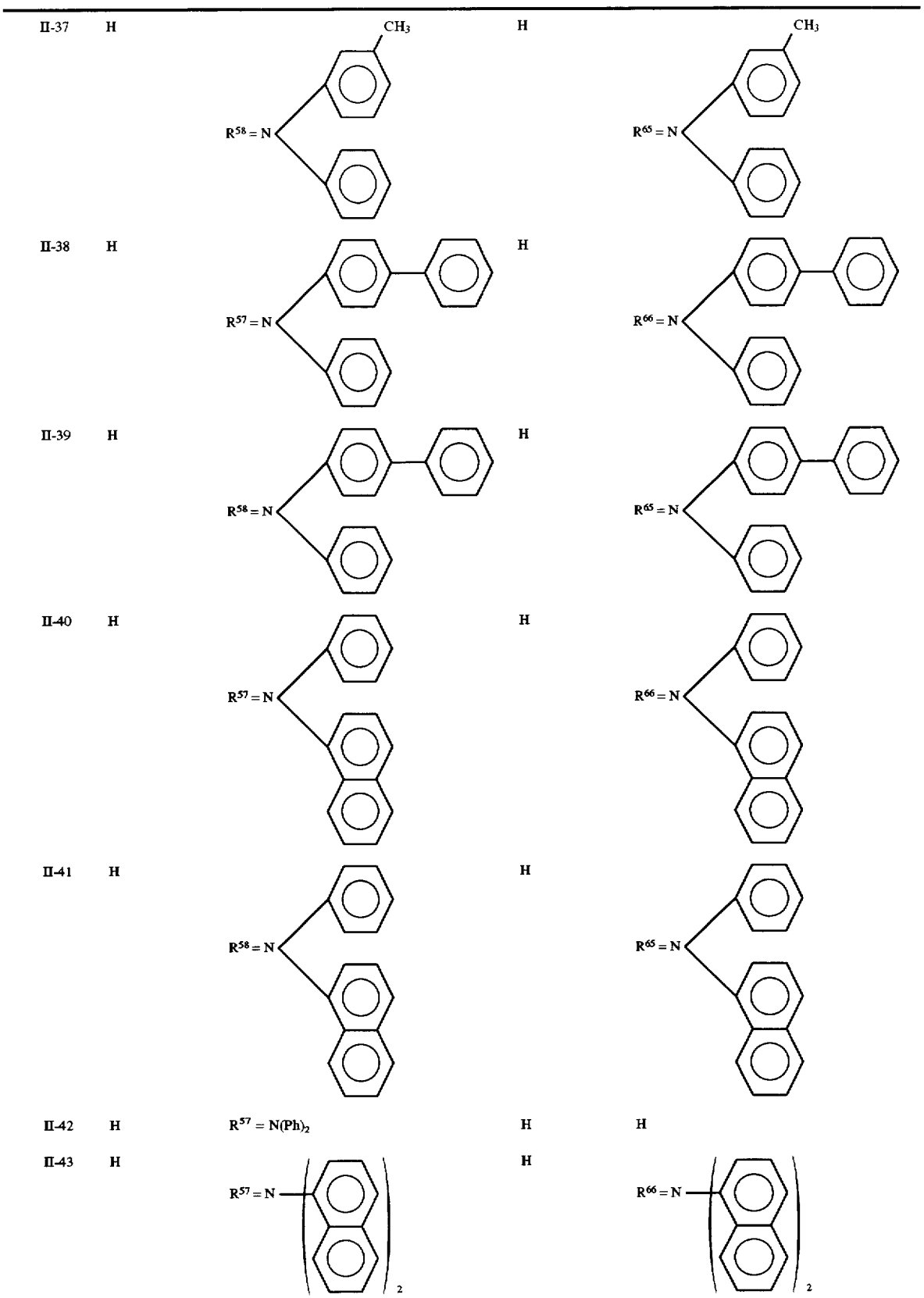

TABLE 2-continued

| II-44 | H | $R^{57}=N-$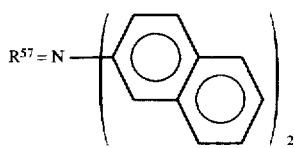$)_2$ | H | $R^{66}=N-$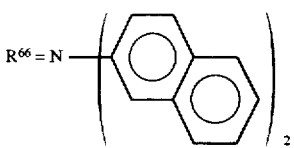$)_2$ | |

| Compound No. | $R^{69} \sim R^{72}$ | $R^{73} \sim R^{77}$ | $R^{78} \sim R^{81}$ | $R^{82} \sim R^{86}$ | $R^{37} \sim R^{44}$ |
|---|---|---|---|---|---|
| II-1 | H | H | H | H | H |
| II-2 | H | $R^{74}$ = CH$_3$ | H | $R^{83}$ = CH$_3$ | H |
| II-3 | H | $R^{75}$ = CH$_3$ | H | $R^{84}$ = CH$_3$ | H |
| II-4 | H | $R^{75}$ = t-C$_4$H$_9$ | H | $R^{84}$ = t-C$_4$H$_9$ | H |
| II-5 | H | $R^{75}$ = OCH$_3$ | H | $R^{84}$ = OCH$_3$ | H |
| II-6 | H | $R^{75}$ = Ph | H | $R^{84}$ = Ph | H |
| II-7 | H | $R^{76}=$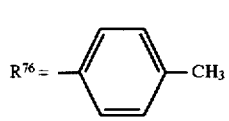$-CH_3$ | H | $R^{84}=$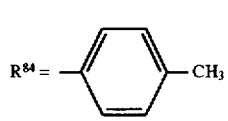$-CH_3$ | H |
| II-8 | H | $R^{75}$ = OPh | H | $R^{84}$ = OPh | H |
| II-9 | H | $R^{75}$ = N(C$_2$H$_5$)$_2$ | H | $R^{84}$ = N(C$_2$H$_5$)$_2$ | H |
| II-10 | H | $R^{75}$ = N(Ph)$_2$ | H | $R^{84}$ = N(Ph)$_2$ | H |
| II-11 | H | $R^{75}$ = Cl | H | $R^{84}$ = Cl | H |
| II-12 | H | $R^{75}=$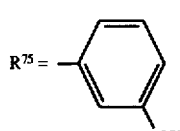$-CH_3$ | H | $R^{84}=$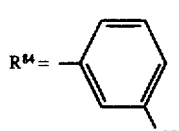$-CH_3$ | H |
| II-13 | $R^{72}$ = CH$_3$ | H | $R^{79}$ = CH$_3$ | H | H |
| II-14 | $R^{72}$ = OCH$_3$ | H | $R^{79}$ = OCH$_3$ | H | H |
| II-15 | $R^{72}$ = Ph | H | $R^{79}$ = Ph | H | H |
| II-16 | $R^{72}$ = OPh | H | $R^{79}$ = OPh | H | H |
| II-17 | $R^{72}$ = N(C$_2$H$_5$)$_2$ | H | $R^{79}$ = N(C$_2$H$_5$)$_2$ | H | H |
| II-18 | $R^{72}$ = Cl | H | $R^{79}$ = Cl | H | H |
| II-19 | H | H | H | H | $R^{37} = R^{42}$ = CH$_3$ |
| II-20 | H | H | H | H | $R^{38} = R^{43}$ = OCH$_3$ |
| II-21 | H | H | H | H | $R^{38} = R^{43}$ = N(CH$_3$)$_2$ |
| II-22 | H | H | H | H | $R^{38} = R^{43}$ = Cl |
| II-23 | H | H | H | H | $R^{40} = R^{43}$ = CH$_3$ |
| II-24 | H | $R^{75}$ = CH$_3$ | H | $R^{83}$ = CH$_3$ | H |
| II-25 | H | $R^{74} = R^{76}$ = CH$_3$ | H | H | H |
| II-26 | H | $R^{74}$ = CH$_3$ | H | $R^{85}$ = CH$_3$ | H |
| II-27 | H | H | H | H | H |
| II-28 | H | H | H | H | H |
| II-29 | H | H | H | H | H |
| II-30 | H | H | H | H | H |
| II-31 | H | H | H | H | H |
| II-32 | H | H | H | H | H |
| II-33 | H | H | H | H | H |
| II-34 | H | H | H | H | H |
| II-35 | H | H | H | H | H |
| II-36 | H | H | H | H | H |
| II-37 | H | H | H | H | H |
| II-38 | H | H | H | H | H |
| II-39 | H | H | H | H | H |
| II-40 | H | H | H | H | H |
| II-41 | H | H | H | H | H |
| II-42 | H | $R^{75}$ = N(Ph)$_2$H | H | H | H |
| II-43 | H | H | H | H | H |
| II-44 | H | H | H | H | H |

TABLE 3

(18')

[Structure: bis(diarylamino)biphenyl with substituents R10–R18, R37–R44, R51–R59, R69–R86]

| Compound No. | R51~R54 | R55~R59 | R10~R13 | R14~R18 | R69~R72 |
|---|---|---|---|---|---|
| III-1 | H | H | H | H | H |
| III-2 | H | R58 = CH3 | H | R17 = CH3 | H |
| III-3 | H | R57 = CH3 | H | R16 = CH3 | H |
| III-4 | H | R58 = t-C4H9 | H | R17 = t-C4H9 | H |
| III-5 | H | R58 = OCH3 | H | R17 = OCH3 | H |
| III-6 | H | R59 = Ph | H | R16 = Ph | H |
| III-7 | H | R58 = –C6H4–CH3 | H | R17 = –C6H4–CH3 | H |
| III-8 | H | R58 = OPh | H | R17 = OPh | H |
| III-9 | H | R58 = N(C2H5)2 | H | R17 = N(C2H5)2 | H |
| III-10 | H | R58 = N(Ph)2 | H | R17 = N(Ph)2 | H |
| III-11 | H | R58 = Cl | H | R17 = Cl | H |
| III-12 | R52 = CH3 | H | R11 = CH3 | H | R72 = CH3 |
| III-13 | R52 = OCH3 | H | R11 = OCH3 | H | R72 = OCH3 |
| III-14 | R52 = Ph | H | R11 = Ph | H | R72 = Ph |
| III-15 | R52 = OPh | H | R11 = OPh | H | R72 = OPh |
| III-16 | R52 = N(C2H5)2 | H | R11 = N(C2H5)2 | H | R72 = N(C2H5)2 |
| III-17 | R52 = Cl | H | R11 = Cl | H | R72 = Cl |
| III-18 | H | H | H | H | H |
| III-19 | H | H | H | H | H |
| III-20 | H | H | H | H | H |
| III-21 | H | H | H | H | H |
| III-22 | H | H | H | H | H |
| III-23 | H | R57 = CH3 | H | R16 = CH3 | H |
| III-24 | H | R57 = CH3 | H | R17 = CH3 | H |
| III-25 | H | H | H | H | H |
| III-26 | H | H | H | H | H |
| III-27 | H | H | H | H | H |
| III-28 | H | H | H | H | H |
| III-29 | H | H | H | H | H |
| III-30 | H | H | H | H | H |
| III-31 | H | H | H | H | H |
| III-32 | H | H | H | H | H |
| III-33 | H | H | H | H | H |
| III-34 | H | H | H | H | H |
| III-35 | H | H | H | H | H |
| III-36 | H | H | H | H | H |
| III-37 | H | H | H | H | H |
| III-38 | H | H | H | H | H |
| III-39 | H | H | R11 = Ph | H | H |

TABLE 3-continued

| | | | | |
|---|---|---|---|---|
| III-40 | H | H | $R^{11} =$ (phenyl with CH$_3$) | H | H |
| III-41 | H | H | $R^{11} =$ (phenyl-N(Ph)$_2$) | H | H |

| Compound No. | $R^{73}\sim R^{77}$ | $R^{78}\sim R^{81}$ | $R^{82}\sim R^{86}$ | $R^{37}\sim R^{44}$ |
|---|---|---|---|---|
| III-1 | H | H | H | H |
| III-2 | $R^{76} = CH_3$ | H | $R^{83} = CH_3$ | H |
| III-3 | $R^{75} = CH_3$ | H | $R^{84} = CH_3$ | H |
| III-4 | $R^{76} = t\text{-}C_4H_9$ | H | $R^{83} = t\text{-}C_4H_9$ | H |
| III-5 | $R^{76} = OCH_3$ | H | $R^{83} = OCH_3$ | H |
| III-6 | $R^{75} = Ph$ | H | $R^{84} = Ph$ | H |
| III-7 | $R^{76} = $ (p-tolyl) | H | $R^{83} = $ (p-tolyl) | H |
| III-8 | $R^{76} = OPh$ | H | $R^{83} = OPh$ | H |
| III-9 | $R^{76} = N(C_2H_5)_2$ | H | $R^{83} = N(C_2H_5)_2$ | H |
| III-10 | $R^{76} = N(Ph)_2$ | H | $R^{83} = N(Ph)_2$ | H |
| III-11 | $R^{76} = Cl$ | H | $R^{83} = Cl$ | H |
| III-12 | H | $R^{79} = CH_3$ | H | H |
| III-13 | H | $R^{79} = OCH_3$ | H | H |
| III-14 | H | $R^{79} = Ph$ | H | H |
| III-15 | H | $R^{79} = OPh$ | H | H |
| III-16 | H | $R^{79} = N(C_2H_5)_2$ | H | H |
| III-17 | H | $R^{79} = Cl$ | H | H |
| III-18 | H | H | H | $R^{37} = R^{42} = CH_3$ |
| III-19 | H | H | H | $R^{38} = R^{41} = CH_3$ |
| III-20 | H | H | H | $R^{38} = R^{41} = OCH_3$ |
| III-21 | H | H | H | $R^{38} = R^{41} = N(CH_3)_2$ |
| III-22 | H | H | H | $R^{38} = R^{41} = Cl$ |
| III-23 | $R^{74} = CH_3$ | H | $R^{85} = CH_3$ | H |
| III-24 | $R^{75} = CH_3$ | H | $R^{85} = CH_3$ | H |
| III-25 | $R^{75} = N(Ph)_2$ | H | $R^{84} = N(Ph)_2$ | H |
| III-26 | $R^{76} = N(Ph)_2$ | H | $R^{83} = N(Ph)_2$ | H |
| III-27 | $R^{75} = N(\text{biphenyl})_2$ | H | $R^{84} = N(\text{biphenyl})_2$ | H |
| III-28 | $R^{76} = N(\text{biphenyl})_2$ | H | $R^{83} = N(\text{biphenyl})_2$ | H |
| III-29 | $R^{76} = N(\text{m-biphenyl})_2$ | H | $R^{84} = N(\text{m-biphenyl})_2$ | H |

TABLE 3-continued
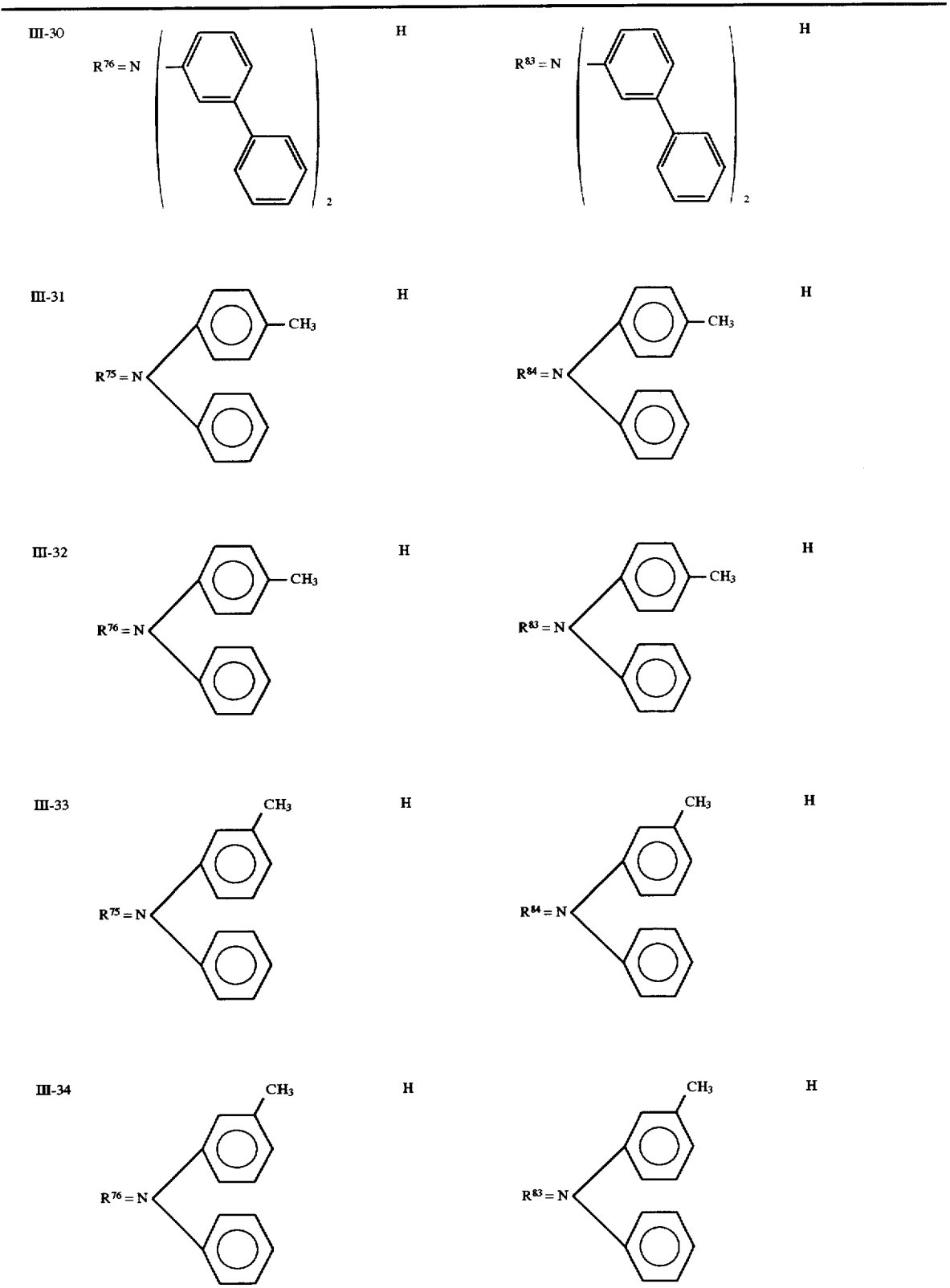

TABLE 3-continued
| | | | | |
|---|---|---|---|---|
| III-35 | 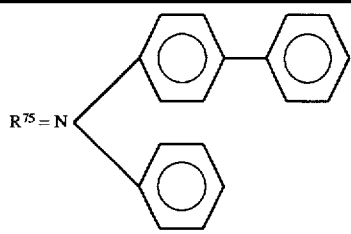 | H | 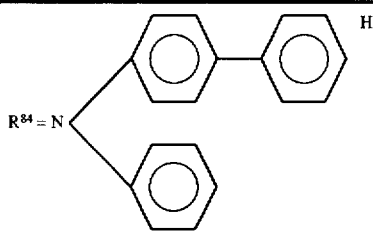 | H |
| III-36 | 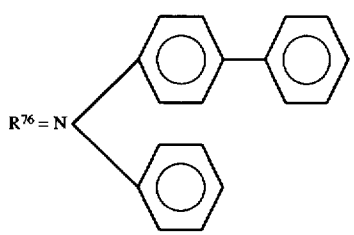 | H | 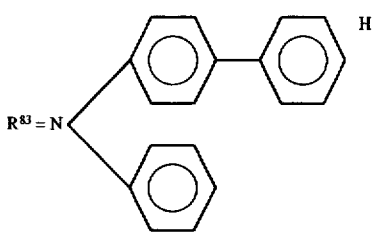 | H |
| III-37 | 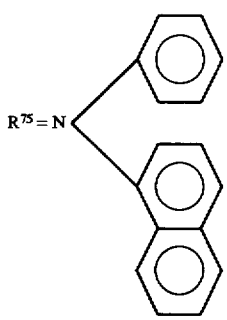 | H | 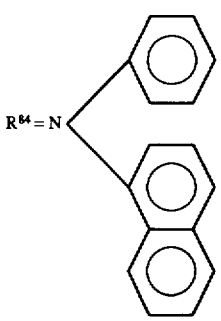 | H |
| III-38 | 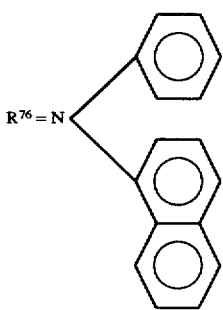 | H | 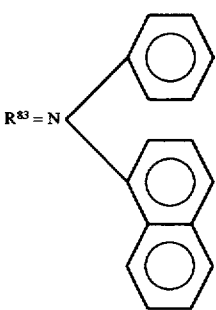 | H |
| III-39 | H | H | H | H |
| III-40 | H | H | H | H |
| III-41 | H | H | H | H |

TABLE 4

[Structure (19): a symmetric diamine-based compound with multiple phenyl rings bearing substituents R¹–R⁸⁶, with two central N atoms]

| Compound No. | $R^1$–$R^4$ | $R^5$–$R^9$ | $R^{10}$–$R^{13}$ | $R^{14}$–$R^{18}$ | $R^{69}$–$R^{72}$ | $R^{73}$–$R^{77}$ | $R^{78}$–$R^{81}$ | $R^{82}$–$R^{86}$ | $R^{37}$–$R^{44}$ |
|---|---|---|---|---|---|---|---|---|---|
| IV-1 | H | H | H | H | H | H | H | H | H |
| IV-2 | $R^2 = CH_3$ | $R^6 = CH_3$ | H | $R^{17} = CH_3$ | H | $R^{76} = CH_3$ | H | $R^{83} = CH_3$ | H |
| IV-3 | $R^2 = OCH_3$ | $R^7 = t\text{-}C_4H_9$ | H | $R^{16} = CH_3$ | H | $R^{75} = CH_3$ | H | $R^{84} = t\text{-}C_4H_9$ | H |
| IV-4 | $R^2 = Ph$ | $R^5 = OCH_3$ | H | $R^{17} = OCH_3$ | H | $R^{76} = OCH_3$ | H | $R^{83} = OCH_3$ | H |
| IV-5 | $R^2 = OPh$ | | H | | H | | H | | H |
| IV-6 | H | $R^6 = $ [p-tolyl] | H | $R^{17} = $ [p-tolyl] | H | $R^{76} = $ [p-tolyl] | H | $R^{83} = $ [p-tolyl] | H |
| IV-7 | | $R^6 = OPh$ | | $R^{17} = OPh$ | H | $R^{76} = OPh$ | H | $R^{83} = OPh$ | H |
| IV-8 | | $R^6 = N(C_2H_5)_2$ | | $R^{17} = N(C_2H_5)_2$ | H | $R^{76} = N(C_2H_5)_2$ | H | $R^{83} = N(C_2H_5)_2$ | H |
| IV-9 | | $R^6 = N(Ph)_2$ | | $R^{17} = N(Ph)_2$ | H | $R^{76} = N(Ph)_2$ | H | $R^{83} = N(Ph)_2$ | H |
| IV-10 | | $R^6 = Cl$ | $R^{11} = CH_3$ | $R^{17} = Cl$ | H | $R^{76} = Cl$ | H | $R^{83} = Cl$ | H |
| IV-11 | | $R^7 = Ph$ | $R^{11} = OCH_3$ | $R^{16} = Ph$ | H | $R^{75} = Ph$ | H | $R^{84} = Ph$ | H |
| IV-12 | | H | $R^{11} = Ph$ | H | H | H | H | H | H |
| IV-13 | | H | $R^{11} = OPh$ | H | H | H | H | H | H |
| IV-14 | | H | $R^{11} = N(C_2H_5)_2$ | H | H | H | H | H | H |
| IV-15 | $R^2 = N(C_2H_5)_2$ | H | $R^{11} = Cl$ | H | H | H | H | H | H |
| IV-16 | $R^2 = Cl$ | H | | H | H | H | H | H | H |
| IV-17 | H | H | | H | H | H | H | H | H |
| IV-18 | H | H | | H | H | H | H | H | H |
| IV-19 | H | H | | H | H | H | H | H | H |
| IV-20 | H | H | | H | H | H | H | H | H |
| IV-21 | H | $R^5 = CH_3$ | | $R^{17} = CH_3$ | H | $R^{75} = CH_3$ | H | $R^{84} = CH_3$ | $R^{38} = R^{41} = CH_3$ |
| IV-22 | H | $R^6 = CH_3$ | | $R^{16} = CH_3$ | H | $R^{76} = CH_3$ | H | $R^{84} = CH_3$ | $R^{38} = R^{41} = OCH_3$ |
| IV-23 | H | H | | H | H | H | H | $R^{84} = N(Ph)_2$ | $R^{38} = R^{41} = N(CH_3)_2$ |
| IV-24 | H | H | | H | H | H | H | H | $R^{38} = R^{41} = Cl$ |

TABLE 4-continued

| | | | | | | | | |
|---|---|---|---|---|---|---|---|---|
| IV-33 | H | H | H | H | H | $R^{76}=N$—CH₂—C₆H₄—CH₃ / C₆H₄— | H | $R^{83}=N$—CH₂—C₆H₄—CH₃ / C₆H₄— | H |
| IV-34 | H | H | H | H | H | $R^{75}=N$—CH₂—C₆H₄(C₆H₅) / C₆H₄— | H | $R^{84}=N$—CH₂—C₆H₄(C₆H₅) / C₆H₄— | H |
| IV-35 | H | H | H | H | H | $R^{76}=N$—CH₂—C₆H₄(C₆H₅) / C₆H₄— | H | $R^{83}=N$—CH₂—C₆H₄(C₆H₅) / C₆H₄— | H |
| IV-36 | H | H | H | H | H | $R^{75}=N$—CH₂—C₆H₅ / naphthyl | H | $R^{84}=N$—CH₂—C₆H₅ / naphthyl | H |
| IV-37 | H | H | H | H | H | $R^{76}=N$—CH₂—C₆H₅ / naphthyl | H | $R^{83}=N$—CH₂—C₆H₅ / naphthyl | H |
| IV-38 | H | | H | | H | $R^{75}=N$—CH₂—C₆H₄(C₆H₅) / C₆H₄— | H | $R^{84}=N$—CH₂—C₆H₄(C₆H₅) / C₆H₄— | H |

TABLE 4-continued

| | | | | | | |
|---|---|---|---|---|---|---|
| IV-39 | H | H | H | H | R<sup>75</sup>=N(naphthyl)<sub>2</sub> | H | R<sup>84</sup>=N(naphthyl)<sub>2</sub> | H |
| IV-40 | H | H | H | H | R<sup>75</sup>=N(naphthyl)<sub>2</sub> | H | R<sup>84</sup>=N(naphthyl)<sub>2</sub> | H |
| IV-41 | H | H | H | H | R<sup>75</sup>=N(CH<sub>3</sub>)<sub>2</sub> | H | R<sup>84</sup>=N(CH<sub>3</sub>)<sub>2</sub> | H |
| IV-42 | H | H | H | H | R<sup>76</sup>=N(CH<sub>3</sub>)<sub>2</sub> | H | | |
| IV-43 | H | H | H | H | R<sup>75</sup>=anthracenyl-Ph | H | R<sup>84</sup>=anthracenyl-Ph | H |

Due to complexity, see original table.

TABLE 5

Structure (20): A tetraaryl diamine compound with two nitrogen atoms, each connected to biphenyl groups bearing substituents R10–R18, R28–R44, R51–R59, and R69–R77.

| Compound No. | R51–R54 | R55–R59 | R10–R13 | R14–R18 | R69–R72 | R73–R77 | R28–R31 | R32–R36 | R37–R44 |
|---|---|---|---|---|---|---|---|---|---|
| V-1 | H | H | H | H | H | H | H | H | H |
| V-2 | H | $R^{58}$ = CH$_3$ | H | $R^{17}$ = CH$_3$ | H | $R^{76}$ = CH$_3$ | H | $R^{35}$ = CH$_3$ | H |
| V-3 | H | $R^{57}$ = C$_2$H$_5$ | H | $R^{16}$ = C$_2$H$_5$ | H | $R^{75}$ = C$_2$H$_5$ | H | $R^{34}$ = C$_2$H$_5$ | H |
| V-4 | H | $R^{58}$ = t-C$_4$H$_9$ | H | $R^{17}$ = t-C$_4$H$_9$ | H | $R^{76}$ = t-C$_4$H$_9$ | H | $R^{35}$ = t-C$_4$H$_9$ | H |
| V-5 | H | $R^{58}$ = OCH$_3$ | H | $R^{17}$ = OCH$_3$ | H | $R^{76}$ = OCH$_3$ | H | $R^{35}$ = OCH$_3$ | H |
| V-6 | H | $R^{58}$ = (4-CH$_3$-C$_6$H$_4$) | H | $R^{17}$ = (4-CH$_3$-C$_6$H$_4$) | H | $R^{76}$ = (4-CH$_3$-C$_6$H$_4$) | H | $R^{36}$ = (4-CH$_3$-C$_6$H$_4$) | H |
| V-7 | H | $R^{58}$ = OPh | H | $R^{17}$ = OPh | H | $R^{76}$ = OPh | H | $R^{35}$ = OPh | H |
| V-8 | H | $R^{58}$ = N(C$_2$H$_5$)$_2$ | H | $R^{17}$ = N(C$_2$H$_5$)$_2$ | H | $R^{76}$ = N(C$_2$H$_5$)$_2$ | H | $R^{35}$ = N(C$_2$H$_5$)$_2$ | H |
| V-9 | H | $R^{58}$ = N(Ph)$_2$ | H | $R^{17}$ = N(Ph)$_2$ | H | $R^{76}$ = N(Ph)$_2$ | H | $R^{35}$ = N(Ph)$_2$ | H |
| V-10 | H | $R^{58}$ = Cl | H | $R^{17}$ = Cl | H | $R^{76}$ = Cl | H | $R^{35}$ = Cl | H |
| V-11 | H | $R^{57}$ = Ph | H | $R^{16}$ = Ph | H | $R^{75}$ = Ph | H | $R^{34}$ = Ph | H |
| V-12 | H | $R^{57}$ = CH$_3$ | H | $R^{16}$ = CH$_3$ | H | $R^{75}$ = CH$_3$ | H | $R^{35}$ = CH$_3$ | H |
| V-13 | H | $R^{57}$ = CH$_3$ | H | $R^{17}$ = CH$_3$ | H | $R^{76}$ = CH$_3$ | H | $R^{36}$ = CH$_3$ | H |
| V-14 | H | H | $R^{11}$ = CH$_3$ | H | H | H | H | $R^{29}$ = CH$_3$ | H |
| V-15 | H | H | $R^{11}$ = OCH$_3$ | H | H | H | H | $R^{29}$ = OCH$_3$ | H |
| V-16 | H | H | $R^{11}$ = Ph | H | H | H | H | H | H |
| V-17 | H | H | $R^{11}$ = OPh | H | H | H | H | H | H |
| V-18 | H | H | $R^{11}$ = N(C$_2$H$_5$)$_2$ | H | H | H | H | H | H |
| V-19 | H | H | $R^{11}$ = Cl | H | H | H | H | H | H |
| V-20 | H | H | H | H | H | H | $R^{29}$ = Ph | H | H |
| V-21 | H | H | H | H | H | H | $R^{29}$ = OPh | H | H |
| V-22 | H | H | H | H | H | H | $R^{29}$ = N(C$_2$H$_5$)$_2$ | H | H |
| V-23 | H | H | H | H | H | H | $R^{29}$ = Cl | H | H |
| V-24 | H | $R^{57}$ = N(Ph)$_2$ | H | H | H | $R^{75}$ = N(Ph)$_2$ | H | H | $R^{38}$ = $R^{41}$ = CH$_3$ |
| | | | | | | | | | $R^{38}$ = $R^{41}$ = OCH$_3$ |
| | | | | | | | | | $R^{38}$ = $R^{41}$ = N(CH$_3$)$_2$ |
| | | | | | | | | | $R^{38}$ = $R^{41}$ = Cl |

TABLE 5-continued
| | | | | | | | |
|---|---|---|---|---|---|---|---|
| V-25 | H | H | R$^{58}$ = N(Ph)$_2$ | H | H | R$^{76}$ = N(Ph)$_2$ | H | H |
| V-26 | H | H | 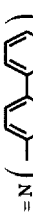 R$^{57}$=N | H | H |  R$^{75}$=N | H | H |
| V-27 | H | H |  R$^{58}$=N | H | H | 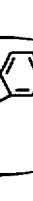 R$^{76}$=N | H | H |
| V-28 | H | H | 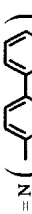 R$^{57}$=N | H | H |  R$^{75}$=N | H | H |
| V-29 | H | H |  R$^{58}$=N | H | H |  R$^{76}$=N | H | H |
| V-30 | H | H |  R$^{57}$=N | H | H | 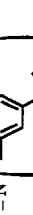 R$^{75}$=N | H | H |
| V-31 | H | H |  R$^{58}$=N | H | H |  R$^{75}$=N | H | H |

TABLE 5-continued
| | | | | | | | | | |
|---|---|---|---|---|---|---|---|---|---|
| V-32 | H | H |  R⁵⁷=N | H | H | H | H |  R⁷⁵=N | H | H |
| V-33 | H | H | 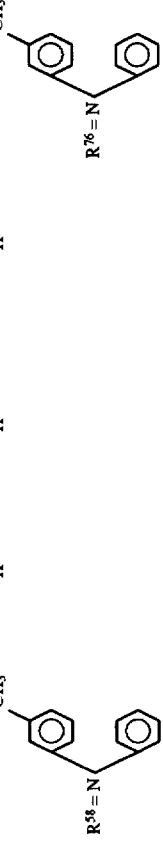 R⁵⁸=N | H | H | H | H | 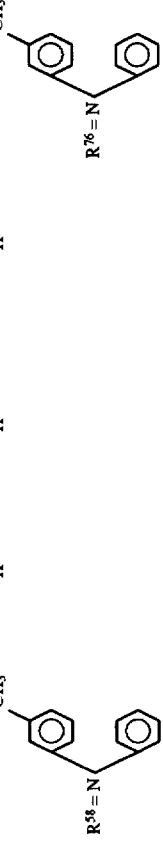 R⁷⁶=N | H | H |
| V-34 | H | H |  R⁵⁷=N | H | H | H | H |  R⁷⁵=N | H | H |
| V-35 | H | H | 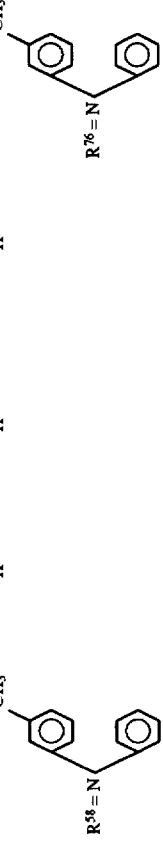 R⁵⁸=N | H | H | H | H | 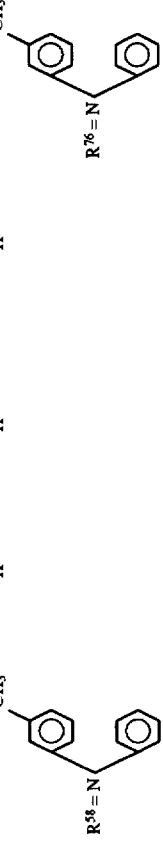 R⁷⁶=N | H | H |

TABLE 5-continued
| | | | | | | | | |
|---|---|---|---|---|---|---|---|---|
| V-36 | H | H | H | R⁵⁷=N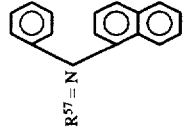 | H | R⁷⁵=N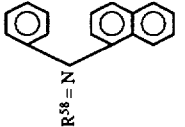 | H | H |
| V-37 | H | H | H | R⁵⁸=N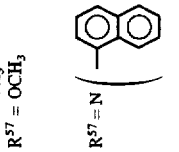 | H | R⁷⁶=N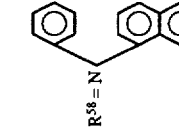 | H | H |
| V-38 | H | H | H | R⁵⁷ = CH₃ | H | R⁷⁵ = CH₃ | H | H |
| V-39 | | | | R⁵⁶ = CH₃ | | R⁷⁴ = CH₃ | | |
| V-40 | | | | R⁵⁷ = OCH₃ | | R⁷⁵ = OCH₃ | | |
| V-41 | H | H | H | R⁵⁷=N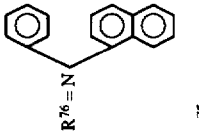₂ | H | R⁷⁵=N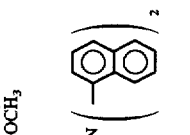₂ | H | H |
| V-42 | H | H | H | R⁵⁷=N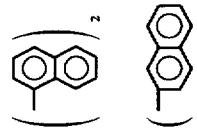₂ | H | R⁷⁵=N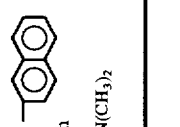₂ | H | H |
| V-43 | H | H | H | R⁵⁷=N—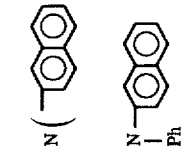<br>Ph | H | R⁷⁵=N—<br>Ph | H | H |
| V-44 | H | H | H | R⁵⁷ = N(CH₃)₂ | H | R⁵⁷ = N(CH₃)₂ | H | H |
| V-45 | H | H | R¹⁷ = Ph | H | H | H | H | R³³ = Ph |

TABLE 6

(21)

| Compound No. | $R^1$–$R^4$ | $R^5$–$R^9$ | $R^{10}$–$R^{13}$ | $R^{14}$–$R^{18}$ | $R^{19}$–$R^{22}$ | $R^{22}$–$R^{27}$ | $R^{78}$–$R^{81}$ | $R^{82}$–$R^{86}$ | $R^{37}$–$R^{44}$ |
|---|---|---|---|---|---|---|---|---|---|
| VI-1 | H | H | H | H | H | H | H | H | H |
| VI-2 | H | $R^8 = CH_3$ | H | $R^{17} = CH_3$ | H | $R^{26} = CH_3$ | H | $R^{83} = CH_3$ | H |
| VI-3 | H | $R^7 = CH_3$ | H | $R^{16} = CH_3$ | H | $R^{25} = CH_3$ | H | $R^{84} = CH_3$ | H |
| VI-4 | H | $R^7 = t\text{-}C_4H_9$ | H | $R^{17} = t\text{-}C_4H_9$ | H | $R^{26} = t\text{-}C_4H_9$ | H | $R^{88} = t\text{-}C_4H_9$ | H |
| VI-5 | H | $R^8 = OCH_3$ | H | $R^{17} = OCH_3$ | H | $R^{26} = OCH_3$ | H | $R^{83} = OCH_3$ | H |
| VI-6 | H | $R^6 =$  | H | $R^{17} =$  | H | $R^{26} =$  | H | $R^{63} =$ [p-tolyl] | H |
| VI-7 | H | $R^6 = OPh$ | H | $R^{17} = OPh$ | H | $R^{26} = OPh$ | H | $R^{83} = OPh$ | H |
| VI-8 | H | $R^5 = N(C_2H_5)_2$ | H | $R^{17} = N(C_2H_5)_2$ | H | $R^{26} = N(C_2H_5)_2$ | H | $R^{83} = N(C_2H_5)_2$ | H |
| VI-9 | H | $R^6 = N(Ph)_2$ | H | $R^{17} = N(Ph)_2$ | H | $R^{26} = N(Ph)_2$ | H | $R^{83} = N(Ph)_2$ | H |
| VI-10 | H | $R^5 = Cl$ | H | $R^{17} = Cl$ | H | $R^{26} = Cl$ | H | $R^{83} = Cl$ | H |
| VI-11 | H | $R^7 = Ph$ | H | $R^{16} = Ph$ | H | $R^{25} = Ph$ | H | $R^{84} = Ph$ | H |
| VI-12 | $R^2 = CH_3$ | H | $R^{11} = CH_3$ | H | $R^{20} = CH_3$ | H | H | H | H |
| VI-13 | $R^2 = OCH_3$ | H | $R^{11} = OCH_3$ | H | $R^{20} = OCH_3$ | H | H | H | H |
| VI-14 | $R^2 = Ph$ | H | $R^{11} = Ph$ | H | $R^{20} = Ph$ | H | H | H | H |
| VI-15 | $R^2 = N(C_2H_5)_2$ | H | $R^{11} = N(C_2H_5)_2$ | H | $R^{20} = N(C_2H_5)_2$ | H | H | H | H |
| VI-16 | $R^2 = Cl$ | H | $R^{11} = Cl$ | H | $R^{20} = Cl$ | H | H | H | H |
| VI-17 | H | H | H | H | H | H | H | H | H |
| VI-18 | H | H | H | H | H | H | H | H | H |
| VI-19 | H | H | H | H | H | H | H | H | $R^{38} = R^{41} = CH_3$ |
| VI-20 | H | H | H | H | H | H | H | H | $R^{38} = R^{41} = OCH_3$ |
| VI-21 | H | H | H | H | H | H | H | H | $R^{38} = R^{41} = N(CH_3)_2$ |
| VI-22 | H | $R^7 = CH_3$ | H | $R^{17} = CH_3$ | H | $R^{25} = CH_3$ | H | $R^{84} = CH_3$ | $R^{38} = R^{41} = Cl$ |
| VI-23 | H | $R^6 = CH_3$ | H | $R^{16} = CH_3$ | H | $R^{26} = CH_3$ | H | $R^{84} = CH_3$ | H |
| VI-24 | H | H | H | H | H | $R^{25} = N(Ph)_2$ | H | $R^{84} = N(Ph)_2$ | H |

TABLE 6-continued

| | | | | | | | | |
|---|---|---|---|---|---|---|---|---|
| VI-25 | H | H | H | H | R²⁶ = N(Ph)₂ | H | R⁸³ = N(Ph)₂ | H |
| VI-26 | H | H | H | H | R²⁵=N(biphenyl)₂ | H | R⁸⁴=N(biphenyl)₂ | H |
| VI-27 | H | H | H | H | R²⁶=N(biphenyl)₂ | H | R⁸³=N(biphenyl)₂ | H |
| VI-28 | H | H | H | H | R²⁵=N(m-biphenyl)₂ | H | R⁸⁴=N(m-biphenyl)₂ | H |
| VI-29 | H | H | H | H | R²⁶=N(m-biphenyl)₂ | H | R⁸³=N(m-biphenyl)₂ | H |
| VI-30 | H | H | H | H | R²⁵=N(p-tolyl)(Ph) | H | R⁸⁴=N(p-tolyl)(Ph) | H |
| VI-31 | H | H | H | H | R²⁶=N(p-tolyl)(Ph) | H | R⁸³=N(p-tolyl)(Ph) | H |
| VI-32 | H | H | H | H | R²⁵=N(o-tolyl)(Ph) | H | R⁸⁴=N(o-tolyl)(Ph) | H |

TABLE 6-continued

| | | | | | | | | |
|---|---|---|---|---|---|---|---|---|
| VI-33 | H | H | H | H | H | [benzyl-N(R$^{26}$)-tolyl] | H | [benzyl-N(R$^{83}$)-tolyl] | H |
| VI-34 | H | H | H | H | H | [benzyl-N(R$^{25}$)-biphenyl] | H | [benzyl-N(R$^{84}$)-biphenyl] | H |
| VI-35 | H | H | H | H | H | [benzyl-N(R$^{26}$)-biphenyl] | H | [benzyl-N(R$^{83}$)-biphenyl] | H |
| VI-36 | H | H | H | H | H | [benzyl-N(R$^{25}$)-naphthyl] | H | [benzyl-N(R$^{84}$)-naphthyl] | H |
| VI-37 | H | H | H | H | | [benzyl-N(R$^{26}$)-naphthyl] | H | [benzyl-N(R$^{83}$)-naphthyl] | H |
| VI-38 | H | H | H | H | H | H | H | R$^{84}$ = CH$_3$ | H |
| VI-39 | H | H | H | H | H | H | H | R$^{83}$ = CH$_3$ | H |
| VI-40 | H | H | H | H | H | H | H | R$^{84}$ = Ph | H |
| VI-41 | H | H | H | H | H | H | H | R$^{84}$ = N(Ph)$_2$ | H |
| VI-42 | H | H | H | H | H | H | H | R$^{84}$ = OPh | H |
| VI-43 | H | H | H | H | H | H | H | R$^{84}$ = OCH$_3$ | H |

TABLE 6-continued

| | | | | | | | | |
|---|---|---|---|---|---|---|---|---|
| VI-44 | H | H | H | H | H | H | H | R⁸⁴ = N(–m-biphenyl)₂ | H |
| VI-45 | H | H | H | H | H | H | H | R⁸⁴ = N(2-naphthyl)(Ph) | H |
| VI-46 | H | H | H | H | H | H | H | R⁸⁴ = N(1-naphthyl)(Ph) | H |
| VI-47 | H | H | H | H | H | H | H | H | H |
| VI-48 | H | R⁶ = Ph | H | R¹⁵ = Ph | H | R²⁴ = Ph | H | R⁸⁴ = N(CH₃)₂ | H |
| VI-49 | H | R⁶ = N(Ph)₂ | H | R¹⁶ = N(Ph)₂ | H | R²⁴ = N(Ph)₂ | H | H | H |
| VI-50 | H | R⁶ = CH₃ | H | R¹⁵ = CH₃ | H | R²⁴ = CH₃ | H | H | H |
| VI-51 | H | R⁷ = CH₃ | H | R¹⁶ = CH₃ | H | R²⁵ = CH₃ | H | H | H |
| VI-52 | H | R⁷ = N(Ph)₂ | H | R¹⁶ = N(Ph)₂ | H | R²⁵ = N(Ph)₂ | H | H | H |

TABLE 7

(22)

[Structure: tetraaryl biphenyl diamine bearing substituents R37–R44 on the central biphenyl, R101–R104 and R105–R108 on the Ar1 and Ar2 rings, and R109–R113, R114–R118 on the two N-aryl rings; Ar1 and Ar2 are attached to the nitrogens.]

| Compound No. | Ar1 | Ar2 | R101~R104 | R105~R108 | R109~R113 | R114~R118 | R37–R44 |
|---|---|---|---|---|---|---|---|
| VII-1 | Ph | Ph | H | H | H | H | H |
| VII-2 | Ph | Ph | H | H | $R^{110}$ = CH$_3$ | $R^{115}$ = CH$_3$ | H |
| VII-3 | Ph | Ph | H | H | $R^{110}$ = t-C$_4$H$_9$ | $R^{115}$ = t-C$_4$H$_9$ | H |
| VII-4 | Ph | Ph | H | H | $R^{110}$ = OCH$_3$ | $R^{115}$ = OCH$_3$ | H |
| VII-5 | Ph | Ph | H | H | H | $R^{115}$ = H | H |
| VII-6 | Ph | Ph | H | H | $R^{111}$ = Ph | H | H |
| VII-7 | Ph | Ph | H | H | $R^{110}$ = p-tolyl | $R^{116}$ = p-tolyl | H |
| VII-8 | Ph | Ph | H | H | $R^{110}$ = OPh | $R^{115}$ = OPh | H |
| VII-9 | Ph | Ph | H | H | $R^{110}$ = N(C$_2$H$_5$)$_2$ | $R^{115}$ = N(C$_2$H$_5$)$_2$ | H |
| VII-10 | Ph | Ph | H | H | $R^{110}$ = N(Ph)$_2$ | $R^{115}$ = N(Ph)$_2$ | H |
| VII-11 | Ph | Ph | H | H | $R^{110}$ = Cl | $R^{115}$ = Cl | H |
| VII-12 | Ph | Ph | $R^{102}$ = CH$_3$ | H | H | H | H |
| VII-13 | Ph | Ph | $R^{102}$ = OCH$_3$ | H | $R^{111}$ = CH$_3$ | $R^{115}$ = CH$_3$ | H |
| VII-14 | Ph | Ph | $R^{102}$ = Ph | $R^{106}$ = CH$_3$ | $R^{111}$ = OCH$_3$ | $R^{115}$ = OCH$_3$ | H |
| VII-15 | Ph | Ph | $R^{102}$ = OPh | $R^{106}$ = OCH$_3$ | H | H | H |
| VII-16 | Ph | Ph | $R^{102}$ = N(C$_2$H$_5$)$_2$ | $R^{106}$ = Ph | H | H | H |
| VII-17 | Ph | Ph | $R^{102}$ = Cl | $R^{106}$ = OPh | H | H | H |
| VII-18 | Ph | Ph | H | $R^{106}$ = N(C$_2$H$_5$)$_2$ | H | H | H |
| VII-19 | Ph | Ph | H | $R^{106}$ = Cl | H | H | $R^{38} = R^{43}$ = CH$_3$ |
| VII-20 | Ph | Ph | H | H | H | H | $R^{38} = R^{43}$ = OCH$_3$ |
| VII-21 | Ph | Ph | H | H | H | H | $R^{38} = R^{43}$ = N(CH$_3$)$_2$ |
| VII-22 | Ph | Ph | H | H | H | H | $R^{38} = R^{43}$ = Cl |
| VII-23 | Ph | Ph | H | H | H | H | H |
| VII-24 | 4-methylphenyl | 4-methylphenyl | H | H | H | H | H |
| VII-25 | 4-biphenylyl | 4-biphenylyl | H | H | H | H | H |

TABLE 7-continued
| | | | | | | |
|---|---|---|---|---|---|---|
| VII-26 |  |  | H | H | H | H |
| VII-27 | Ph | Ph | H | H | H | H |
| VII-28 |  |  | H | H | H | H |
| VII-29 | 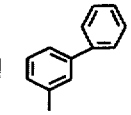 | 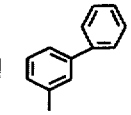 | H | H | H | H |
| VII-30 |  |  | H | H | H | H |
| VII-31 | 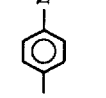 | 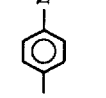 | H | H | H | H |
| VII-32 | 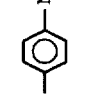 | 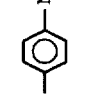 | H | H | H | H |
| VII-33 | 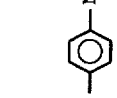 | 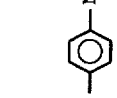 | H | H | H | H |
| VII-34 |  |  | H | H | H | H |

TABLE 7-continued

| | | | | | | |
|---|---|---|---|---|---|---|
| VII-35 | (structure) | (structure) | H | H | H | H | H |
| VII-36 | (structure) | (structure) | H | H | H | H | H |
| VII-37 | (structure) | (structure) | H | H | H | H | H |
| VII-38 | (structure) | (structure) | H | H | H | H | H |
| VII-39 | (structure) | (structure) | H | H | H | H | H |
| VII-40 | (structure) | (structure) | H | H | H | H | H |
| VII-41 | (structure) | (structure) | H | H | H | H | H |
| VII-42 | (structure) | (structure) | H | H | H | H | H |

TABLE 7-continued

| | | | | | | |
|---|---|---|---|---|---|---|
| VII-43 | (anthracene) | (anthracene) | H | H | H | H |
| VII-44 | (pyrene-like) | (pyrene-like) | H | H | H | H |
| VII-45 | (perylene-like) | (perylene-like) | H | H | H | H |
| VII-46 | (coronene) | (coronene) | H | H | H | H |

TABLE 8

(23)

[Structure (23): A biphenyl-based diamine compound with two nitrogen centers, each bearing Ar1/Ar3 substituents and phenyl rings with R101-R104, R115-R118, R124-R127, R37-R44, R114-R118, R115-R116, R117, R119-R121, R122-R123 substituents]

| Compound No. | Ar₁ | Ar₃ | R¹⁰¹–R¹⁰⁴ | R¹¹⁴–R¹¹⁸ | R¹²⁴–R¹²⁷ | R¹¹⁴–R¹¹⁸ | R³⁷–R⁴⁴ |
|---|---|---|---|---|---|---|---|
| VIII-1 | Ph | Ph | H | H | H | H | H |
| VIII-2 | Ph | Ph | H | H | H | H | R³⁷ = R⁴² = Cl |
| VIII-3 | Ph | Ph | H | H | H | H | R³⁸ = R⁴³ = CH₃ |
| VIII-4 | Ph | Ph | H | H | H | H | R³⁸ = R⁴³ = OCH₃ |
| VIII-5 | Ph | Ph | H | H | H | H | R³⁸ = R⁴³ = N(CH₃)₂ |
| VIII-6 | Ph | Ph | R¹²² = OCH₃ | R¹¹⁵ = OCH₃ | H | H | H |
| VIII-7 | Ph | Ph | H | R¹²² = [p-tolyl] | H | R¹¹⁵ = [p-tolyl] | H |
| VIII-8 | Ph | Ph | H | R¹²² = OPh | H | R¹¹⁵ = OPh | H |
| VIII-9 | Ph | Ph | H | R¹²² = N(C₂H₅)₂ | H | R¹¹⁵ = N(C₂H₅)₂ | H |
| VIII-10 | Ph | Ph | H | R¹²² = N(Ph)₂ | H | R¹¹⁵ = N(Ph)₂ | H |
| VIII-11 | Ph | Ph | H | R¹²² = Cl | H | R¹¹⁵ = Cl | H |
| VIII-12 | Ph | Ph | H | R¹²² = t-C₄H₉ | H | R¹¹⁵ = t-C₄H₉ | H |
| VIII-13 | Ph | Ph | H | R¹²² = CH₃ | H | R¹¹⁵ = CH₃ | H |
| VIII-14 | Ph | Ph | H | R¹²¹ = CH₃ | H | R¹¹⁶ = CH₃ | H |
| VIII-15 | Ph | Ph | H | R¹²¹ = Ph | H | H | H |
| VIII-16 | Ph | Ph | R¹⁰² = CH₃ | H | R¹²⁶ = CH₃ | H | H |
| VIII-17 | Ph | Ph | R¹⁰² = OCH₃ | H | R¹²⁶ = OCH₃ | H | H |
| VIII-18 | Ph | Ph | R¹⁰² = Ph | H | R¹²⁶ = Ph | H | H |
| VIII-19 | Ph | Ph | R¹⁰² = OPh | H | R¹²⁶ = OPh | H | H |
| VIII-20 | Ph | Ph | R¹⁰² = N(C₂H₅)₂ | H | R¹²⁶ = N(C₂H₅)₂ | H | H |
| VIII-21 | Ph | Ph | R¹⁰² = Cl | H | R¹²⁶ = Cl | H | H |
| VIII-22 | [p-tolyl] | [p-tolyl] | H | H | H | H | H |
| VIII-23 | [biphenyl] | [biphenyl] | H | H | H | H | H |
| VIII-24 | [m-tolyl (CH₃-phenyl)] | [m-tolyl (CH₃-phenyl)] | H | H | H | H | H |

TABLE 8-continued
| | | | | | | | |
|---|---|---|---|---|---|---|---|
| VIII-25 |  | 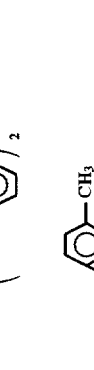 | H | H | H | H | H |
| VIII-26 | 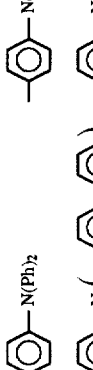 | 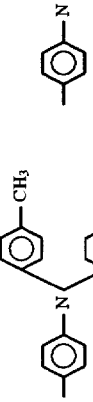 | H | H | H | H | H |
| VIII-27 | 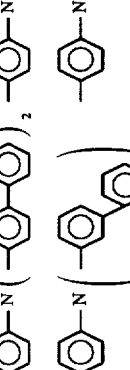 | 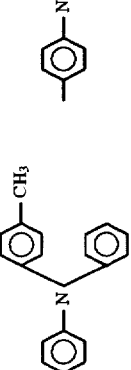 | H | H | H | H | H |
| VIII-28 | 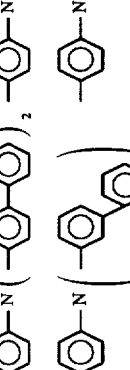 | 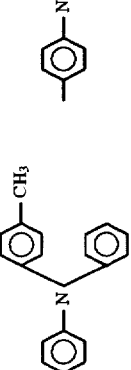 | H | H | H | H | H |
| VIII-29 | 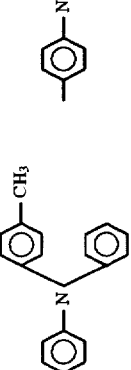 | 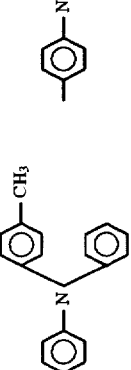 | H | H | H | H | H |
| VIII-30 | 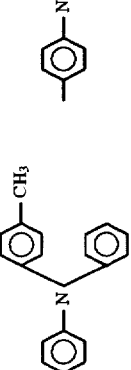 | 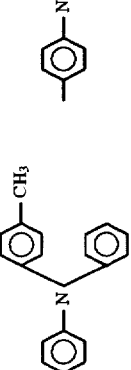 | H | H | H | H | H |
| VIII-31 | 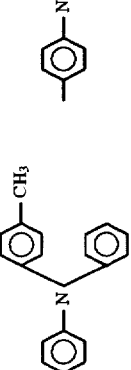 | 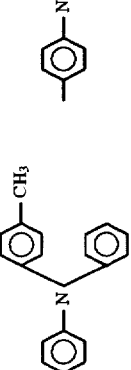 | H | H | H | H | H |

TABLE 8-continued

| ID | Structure 1 | Structure 2 | | | | | | |
|---|---|---|---|---|---|---|---|---|
| VIII-32 | N(p-tolyl)(CH2Ph)(CH2Ph) | N(p-tolyl)(CH2Ph)(CH2Ph) | H | H | H | H | H | H |
| VIII-33 | N(p-tolyl)(CH2Ph)(CH2-naphthyl) | N(p-tolyl)(CH2Ph)(CH2-naphthyl) | H | H | H | H | H | H |
| VIII-34 | 2-methylnaphthyl | 2-methylnaphthyl | H | H | H | H | H | H |
| VIII-35 | 4-OPh-tolyl | 4-OPh-tolyl | H | H | H | H | H | H |
| VIII-36 | 3,5-dimethylphenyl-Ph | 3,5-dimethylphenyl | H | H | H | H | H | $R^{37} = R^{42} = CH_3$ |
| VIII-37 | | | | | | | H | H |
| VIII-38 | 2-methylanthracenyl | 2-methylanthracenyl | H | H | H | H | H | H |
| VIII-39 | 9-anthracenyl | 9-anthracenyl | H | H | H | H | H | H |

TABLE 8-continued

| | | | | | | | |
|---|---|---|---|---|---|---|---|
| VIII-40 | (anthracene-like) | (anthracene-like) | H | H | H | H | H |
| VIII-41 | (naphthalene-like) | (naphthalene-like) | H | H | H | H | H |
| VIII-42 | (pyrene-like) | (pyrene-like) | H | H | H | H | H |
| VIII-43 | (chrysene-like) | (chrysene-like) | H | H | H | H | H |
| VIII-44 | (coronene-like) | (coronene-like) | H | H | H | H | H |

TABLE 9

(24)

[Structure: tetraaryl-benzidine type diamine with substituents R37-R44 on central biphenyl, R101-R104 and R105-R108 on Ar2/Ar1 phenyls, R114-R118 on one N-aryl, R124-R127 on another N-aryl, with Ar1, Ar2, Ar3 groups attached to N atoms]

| Compound No. | Ar₁ | Ar₂ | Ar₃ | R¹⁰¹–R¹⁰⁴ | R¹⁰⁵–R¹⁰⁸ | R¹²⁴–R¹²⁷ | R¹¹⁴–R¹¹⁸ | R³⁷–R³⁴ |
|---|---|---|---|---|---|---|---|---|
| IX-1 | Ph | Ph | Ph | H | H | H | H | H |
| IX-2 | Ph | Ph | Ph | H | H | H | R¹¹⁶ = CH₃ | R³⁷ = R⁴³ = CH₃ |
| IX-3 | Ph | Ph | Ph | H | H | H | H | R³⁸ = R⁴³ = OCH₃ |
| IX-4 | Ph | Ph | Ph | H | H | H | H | R³⁸ = R⁴³ = N(CH₃)₂ |
| IX-5 | Ph | Ph | Ph | H | H | H | R¹¹⁵ = CH₃ | R³⁸ = R⁴³ = Cl |
| IX-6 | Ph | Ph | Ph | H | H | H | R¹¹⁵ = t-C₄H₉ | H |
| IX-7 | Ph | Ph | Ph | H | H | H | R¹¹⁵ = OCH₃ | H |
| IX-8 | Ph | Ph | Ph | H | H | H |  | H |
| IX-9 | Ph | Ph | Ph | H | H | H | R¹¹⁵ = —C₆H₄—CH₃ | H |
| IX-10 | Ph | Ph | Ph | H | H | H | R¹¹⁵ = OPh | H |
| IX-11 | Ph | Ph | Ph | H | H | H | R¹¹⁵ = N(C₂H₅)₂ | H |
| IX-12 | Ph | Ph | Ph | H | H | H | R¹¹⁵ = N(Ph)₂ | H |
| IX-13 | Ph | Ph | Ph | R¹⁰² = CH₃ | R¹⁰⁶ = CH₃ | R¹²⁶ = CH₃ | R¹¹⁵ = Cl | H |
| IX-14 | Ph | Ph | Ph | R¹⁰² = OCH₃ | R¹⁰⁶ = OCH₃ | R¹²⁶ = OCH₃ | H | H |
| IX-15 | Ph | Ph | Ph | R¹⁰² = Ph | R¹⁰⁶ = Ph | R¹²⁶ = Ph | H | H |
| IX-16 | Ph | Ph | Ph | R¹⁰² = OPh | R¹⁰⁶ = OPh | R¹²⁶ = OPh | H | R³⁷–R⁴⁴ |
| IX-17 | Ph | Ph | Ph | R¹⁰² = N(C₂H₅)₂ | R¹⁰⁶ = N(C₂H₅)₂ | R¹²⁶ = N(C₂H₅)₂ | H | H |
| IX-18 | Ph | Ph | Ph | R¹⁰² = Cl | R¹⁰⁶ = Cl | R¹²⁶ = Cl | H | H |
| IX-19 | Ph | Ph | Ph | H | H | H | H | H |
| IX-20 | —C₆H₄—CH₃ | —C₆H₄—CH₃ | —C₆H₄—CH₃ | H | H | H | H | H |
| IX-21 | —C₆H₄—C₆H₅ | —C₆H₄—C₆H₅ | —C₆H₄—C₆H₅ | H | H | H | H | H |

TABLE 9-continued
| | | | | | | | | |
|---|---|---|---|---|---|---|---|---|
| IX-22 |  |  |  | H | H | H | H | H |
| IX-23 |  |  |  | H | H | H | H | H |
| IX-24 |  |  |  | H | H | H | H | H |
| IX-25 |  |  |  | H | H | H | H | H |
| IX-26 |  |  |  | H | H | H | H | H |
| IX-27 |  |  |  | H | H | H | H | H |
| IX-28 |  |  |  | H | H | H | H | H |
| IX-29 |  |  |  | H | H | H | H | H |

TABLE 9-continued

| | | | | | | | | |
|---|---|---|---|---|---|---|---|---|
| IX-30 | ![structure] | ![structure] | ![structure] | H | H | H | H | H |
| IX-31 | ![structure] | ![structure] | ![structure] | H | H | H | H | H |
| IX-32 | p-tolyl-N(Ph)₂ | p-tolyl-N(Ph)₂ | p-tolyl-N(Ph)₂ | H | H | H | H | H |
| IX-33 | p-tolyl-N(Ph)₂ / Ph | p-tolyl-N(Ph)₂ / Ph | Ph | H | H | H | H | H |
| IX-34 | Ph | p-tolyl-N(Ph)₂ / Ph | p-tolyl-N(Ph)₂ / Ph | H | H | H | H | H |
| IX-35 | biphenyl / Ph | Ph | Ph | H | H | H | H | H |
| IX-36 | Ph | naphthyl / Ph | naphthyl | H | H | H | H | H |
| IX-37 | m-tolyl-CH₃ | m-tolyl-CH₃ / Ph | p-tolyl-CH₃ / Ph | H | H | H | H | H |
| IX-38 | p-tolyl-CH₃ | p-tolyl-CH₃ / Ph | Ph | H | H | H | H | H |
| IX-39 | biphenyl | biphenyl | Ph | H | H | H | H | H |

TABLE 9-continued

| | | | | | | | | |
|---|---|---|---|---|---|---|---|---|
| IX-40 | (naphthyl) | Ph | Ph | H | H | H | H | H | H |
| IX-41 | (biphenyl) | Ph | Ph | H | H | H | H | H | H |
| IX-42 | (anthracenyl) | Ph | Ph | H | H | H | H | H | H |
| IX-43 | (anthracenyl) | Ph | Ph | H | H | H | H | H | H |
| IX-44 | (anthracenyl) | Ph | Ph | H | H | H | H | H | H |
| IX-45 | (pyrenyl) | Ph | Ph | H | H | H | H | H | H |
| IX-46 | (pyrenyl) | Ph | Ph | H | H | H | H | H | H |
| IX-47 | (coronenyl) | Ph | Ph | H | H | H | H | H | H |

TABLE 10

(25)

| Compound No. | Ar$_4$ | Ar$_5$ | R$^{201}$–R$^{204}$ | R$^{205}$–R$^{208}$ | R$^{209}$–R$^{213}$ | R$^{214}$–R$^{218}$ | R$^{37}$–R$^{44}$ |
|---|---|---|---|---|---|---|---|
| X-1 | Ph | Ph | H | H | H | H | H |
| X-2 | 4-MeC$_6$H$_4$-N(Ph)$_2$ | 4-MeC$_6$H$_4$-N(Ph)$_2$ | H | H | H | H | H |
| X-3 | (biphenylyl)$_2$N-C$_6$H$_4$- | (biphenylyl)$_2$N-C$_6$H$_4$- | H | H | H | H | H |
| X-4 | Ph(biphenylyl)N-C$_6$H$_4$- | Ph(biphenylyl)N-C$_6$H$_4$- | H | H | H | H | H |
| X-5 | (4-biphenylyl)$_2$N-C$_6$H$_4$- | (4-biphenylyl)$_2$N-C$_6$H$_4$- | H | H | H | H | H |
| X-6 | Ph(4-biphenylyl)N-C$_6$H$_4$- | Ph(4-biphenylyl)N-C$_6$H$_4$- | H | H | H | H | H |
| X-7 | Ph(4-MeC$_6$H$_4$)N-C$_6$H$_4$- | Ph(4-MeC$_6$H$_4$)N-C$_6$H$_4$- | H | H | H | H | H |

TABLE 10-continued

TABLE 10-continued

| | | | | | | |
|---|---|---|---|---|---|---|
| X-17 | ![structure] | ![structure] | H | H | H | H |
| X-18 | ![structure] | ![structure] | H | H | H | $R^{37} = R^{42} = CH_3$ |
| X-19 | ![structure] | ![structure] | H | H | H | $R^{37} = R^{42} = CH_3$ |
| X-20 | ![structure] | ![structure] | H | H | H | H |
| X-21 | ![structure] | ![structure] | H | H | H | H |
| X-22 | ![structure] | ![structure] | H | H | H | H |
| X-23 | ![structure] | ![structure] | H | H | H | H |
| X-24 | ![structure] | ![structure] | H | H | H | H |
| X-25 | Ph | Ph | H | H | $R^{210} = CH_3$ | $R^{215} = CH_3$ | H |
| X-26 | Ph | Ph | H | H | $R^{211} = CH_3$ | $R^{216} = CH_3$ | H |
| X-27 | Ph | Ph | H | H | $R^{211} = t\text{-}C_4H_9$ | $R^{216} = t\text{-}C_4H_9$ | H |
| X-28 | Ph | Ph | H | H | $R^{211} = OCH_3$ | $R^{216} = OCH_3$ | H |
| X-29 | Ph | Ph | H | H | $R^{211} = Ph$ | H | H |
| X-30 | Ph | Ph | H | H | $R^{211} =$ (tolyl) | $R^{216} =$ (tolyl) | H |

TABLE 10-continued

| | | | | | |
|---|---|---|---|---|---|
| X-31 | Ph | Ph | H | H | $R^{211}$ = OPh | $R^{216}$ = OPh | H |
| X-32 | Ph | Ph | H | H | $R^{211}$ = N(C$_2$H$_5$)$_2$ | $R^{216}$ = N(C$_2$H$_5$)$_2$ | H |
| X-33 | Ph | Ph | H | H | $R^{211}$ = N(Ph)$_2$ | $R^{216}$ = N(Ph)$_2$ | H |
| X-34 | Ph | Ph | H | H | $R^{211}$ = Cl | $R^{216}$ = Cl | H |
| X-35 | Ph | Ph | H | H | $R^{211}$ = CH$_3$ | $R^{215}$ = CH$_3$ | H |
| X-36 | Ph | Ph | H | H | H | H | $R^{38}$ = $R^{43}$ = CH$_3$ |
| X-37 | Ph | Ph | H | H | H | H | $R^{38}$ = $R^{43}$ = OCH$_3$ |
| X-38 | Ph | Ph | H | H | H | H | $R^{38}$ = $R^{43}$ = N(CH$_3$)$_2$ |
| X-39 | Ph | Ph | H | H | H | H | $R^{38}$ = $R^{43}$ = Cl |
| X-40 | Ph | Ph | H | H | H | H | $R^{37}$ = $R^{42}$ = CH$_3$ |
| X-41 | Ph | Ph | H | H | H | H | H |
| X-42 | 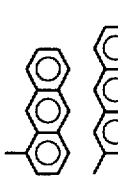 | 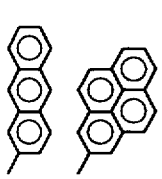 | H | H | H | H | H |
| X-43 |  | 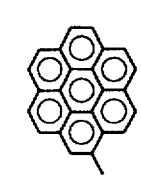 | H | H | H | H | H |
| X-44 | 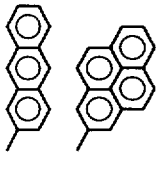 | 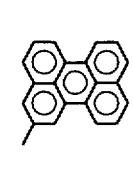 | H | H | H | H | H |
| X-45 | 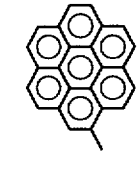 | 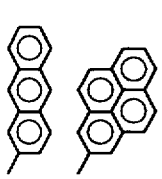 | H | H | H | H | H |

TABLE 11

(structure 26 shown with R groups labeled: R201-R204, R37-R44, R214-R227, Ar4, Ar6)

| Compound No. | Ar4 | Ar6 | R201–R204 | R219–R223 | R224–R227 | R214–R218 | R37–R44 |
|---|---|---|---|---|---|---|---|
| XI-1 | Ph | Ph | H | H | H | H | H |
| XI-2 | Ph | Ph | H | H | H | H | R37 = R42 = Cl |
| XI-3 | Ph | Ph | H | H | H | H | R37 = R42 = OCH3 |
| XI-4 | Ph | Ph | | | | | R37 = R42 = CH3 |
| XI-5 | 4-biphenyl | 4-biphenyl | H | H | H | H | H |
| XI-6 | 3-biphenyl | 3-biphenyl | H | H | H | H | H |
| XI-7 | 2-naphthyl | 2-naphthyl | H | H | H | H | H |
| XI-8 | 1-naphthyl | 1-naphthyl | H | H | H | H | H |

TABLE 11-continued

| | | | | | | |
|---|---|---|---|---|---|---|
| XI-9 | [anthracene] | [anthracene] | H | H | H | H | H | H |
| XI-10 | [Ph-N(Ph)₂] | [Ph-N(Ph)₂] | H | H | H | H | H | H |
| XI-11 | [Ph-N(biphenyl)₂] | [Ph-N(biphenyl)₂] | H | H | H | H | H | H |
| XI-12 | [Ph-N(CPh₂)] | [Ph-N(CPh₂)] | H | H | H | H | H | H |
| XI-13 | [Ph-N(Ph)(biphenyl)] | [Ph-N(Ph)(biphenyl)] | H | H | H | H | H | H |
| XI-14 | [Ph-N(Ph)(naphthyl)] | [Ph-N(Ph)(naphthyl)] | H | H | H | H | H | H |
| XI-15 | [Ph-N(Ph)(naphthyl)] | [Ph-N(Ph)(naphthyl)] | H | H | H | H | H | H |
| XI-16 | [Ph-N(Ph)(pyrenyl)] | [Ph-N(Ph)(pyrenyl)] | H | H | H | H | H | H |

TABLE 11-continued

| | | | | | | |
|---|---|---|---|---|---|---|
| XI-17 |  | H | H | H | H | H |
| XI-18 |  | H | H | H | H | H |
| XI-19 |  | H | H | H | H | H |
| XI-20 |  | H | H | H | H | H |
| XI-21 |  | H | H | H | H | H |
| XI-22 |  | H | H | H | H | H |
| XI-23 |  | H | $R^{220} = CH_3$ | H | $R^{215} = CH_3$ | H |
| XI-24 | Ph | Ph | H | $R^{220} = CH_3$ | H | H |
| XI-25 | Ph | Ph | H | $R^{221} = CH_3$ | H | $R^{217} = CH_3$ | H |
| XI-26 | Ph | Ph | H | $R^{221} = t\text{-}C_4H_9$ | H | $R^{216} = t\text{-}C_4H_9$ | H |
| XI-27 | Ph | Ph | H | $R^{221} = OCH_3$ | H | $R^{216} = OCH_3$ | H |
| XI-28 | Ph | Ph | H | $R^{221} = Ph$ | H | H | H |
| XI-29 | Ph | Ph | H | $R^{221} = OPh$ | H | $R^{216} = OPh$ | H |
| XI-30 | Ph | Ph | H | $R^{221} = N(C_2H_5)_2$ | H | $R^{216} = N(C_2H_5)_2$ | H |
| XI-31 | Ph | Ph | H | $R^{221} = N(Ph)_2$ | H | $R^{216} = N(Ph)_2$ | H |
| XI-32 | Ph | Ph | H | $R^{221} = Cl$ | H | $R^{216} = Cl$ | H |
| XI-33 | Ph | Ph | H | $R^{221} = CH_3$ | H | $R^{217} = CH_3$ | H |
| XI-34 | Ph | Ph | H | H | H | H | $R^{38} = R^{43} = CH_3$ |
| XI-35 | Ph | Ph | H | H | H | H | $R^{38} = R^{43} = OCH_3$ |
| XI-36 | Ph | Ph | H | H | H | H | $R^{38} = R^{43} = Cl$ |
| XI-37 | Ph | Ph | H | H | H | H | $R^{38} = R^{43} = N(CH_3)_2$ |
| XI-38 | Ph | Ph | H |  | H |  | H |
| XI-39 |  |  | H | H | H | H | H |

TABLE 11-continued
| | | | | | | |
|---|---|---|---|---|---|---|
| XI-40 |  |  | H | H | H | H |
| XI-41 |  |  | H | H | H | H |
| XI-42 | 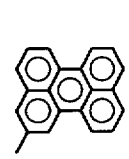 | 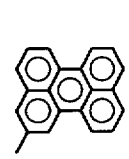 | H | H | H | H |
| XI-43 | 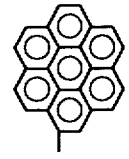 | 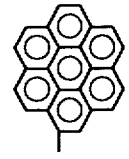 | H | H | H | H |

TABLE 12

(27)

| Compound No. | Ar$_4$ | Ar$_5$ | Ar$_6$ | R$^{201}$–R$^{204}$ | R$^{205}$–R$^{208}$ | R$^{224}$–R$^{227}$ | R$^{214}$–R$^{218}$ | R$^{37}$–R$^{44}$ |
|---|---|---|---|---|---|---|---|---|
| XII-1 | Ph | Ph | Ph | H | H | H | H | H |
| XII-2 | Ph | Ph | Ph | H | H | H | R$^{215}$ = CH$_3$ | R$^{37}$ = R$^{42}$ = CH$_3$ |
| XII-3 | Ph | Ph | Ph | H | H | H | R$^{215}$ = OCH$_3$ | H |
| XII-4 | Ph | Ph | Ph | H | H | H | R$^{215}$ = OPh | H |
| XII-5 | Ph | Ph | Ph | H | H | H | R$^{215}$ = Cl | R$^{37}$ = R$^{42}$ = Cl |
| XII-6 | 3-CH$_3$-C$_6$H$_4$ | 3-CH$_3$-C$_6$H$_4$ | Ph | H | H | H | H | H |
| XII-7 | 4-N(Ph)$_2$-C$_6$H$_4$ | 4-N(Ph)$_2$-C$_6$H$_4$ | Ph | H | H | H | H | H |
| XII-8 | 4-N(Ph)(3-CH$_3$-C$_6$H$_4$)-C$_6$H$_4$ | 4-N(Ph)(3-CH$_3$-C$_6$H$_4$)-C$_6$H$_4$ | Ph | H | H | H | H | H |
| XII-9 | 4-N(4-CH$_3$-C$_6$H$_4$)$_2$-C$_6$H$_4$ | 4-N(4-CH$_3$-C$_6$H$_4$)$_2$-C$_6$H$_4$ | Ph | H | H | H | H | H |
| XII-10 | 4-N(3-CH$_3$-C$_6$H$_4$)$_2$-C$_6$H$_4$ | 4-N(3-CH$_3$-C$_6$H$_4$)$_2$-C$_6$H$_4$ | Ph | H | H | H | H | H |
| XII-11 | 4-N(3-CH$_3$-C$_6$H$_4$)$_2$-C$_6$H$_4$ | 4-N(3-CH$_3$-C$_6$H$_4$)$_2$-C$_6$H$_4$ | 4-N(3-CH$_3$-C$_6$H$_4$)$_2$-C$_6$H$_4$ | H | H | H | H | H |

TABLE 12-continued

| | | | | | | | |
|---|---|---|---|---|---|---|---|
| XII-12 | (structure) | (structure) | (structure) | H | H | H | H |
| XII-13 | (structure) | (structure) | (structure) | H | H | H | H |
| XII-14 | (structure) | (structure) | (structure) | H | H | H | H |
| XII-15 | (structure) | (structure) | (structure) | H | H | H | H |
| XII-16 | (structure) | (structure) | (structure) | H | H | H | H |
| XII-17 | (structure) | (structure) | (structure) | H | H | H | H |
| XII-18 | (structure) | (structure) | (structure) | H | H | H | H |
| XII-19 | (structure) | (structure) | (structure) | H | H | H | H |
| XII-20 | (structure) | (structure) | (structure) | H | H | H | H |
| XII-21 | (structure) | (structure) | (structure) | H | H | H | H |
| XII-22 | (structure) | (structure) | (structure) | H | H | H | H |
| XII-23 | (structure) | (structure) | (structure) | H | H | H | H |
| XII-24 | (structure) | (structure) | (structure) | H | H | H | H |

TABLE 12-continued

| | | | | | | | | |
|---|---|---|---|---|---|---|---|---|
| XII-25 | 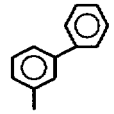 | 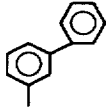 | Ph | H | H | H | H | H |
| XII-26 |  | Ph |  | H | H | H | H | H |
| XII-27 |  |  |  | H | H | H | H | H |
| XII-28 |  |  |  | H | H | H | H | H |
| XII-29 | Ph | Ph | Ph | H | H | H | $R^{215} = CH_3$ | H |
| XII-30 | Ph | Ph | Ph | H | H | H | $R^{216} = CH_3$ | H |
| XII-31 | Ph | Ph | Ph | H | H | H | $R^{216} = t\text{-}C_4H_9$ | H |
| XII-32 | Ph | Ph | Ph | H | H | H | $R^{216} = OCH_3$ | H |
| XII-33 | Ph | Ph | Ph | H | H | H | $R^{216} =$  | H |
| XII-34 | Ph | Ph | Ph | H | H | H | $R^{216} = OPh$ | H |
| XII-35 | Ph | Ph | Ph | H | H | H | $R^{216} = N(C_2H_5)_2$ | H |
| XII-36 | Ph | Ph | Ph | H | H | H | $R^{216} = N(Ph)_2$ | H |
| XII-37 | Ph | Ph | Ph | H | H | H | $R^{216} = Cl$ | H |
| XII-38 | Ph | Ph | Ph | H | H | H | H | $R^{38} = R^{43} = CH_3$ |
| XII-39 | Ph | Ph | Ph | H | H | H | H | $R^{38} = R^{43} = OCH_3$ |
| XII-40 | Ph | Ph | Ph | H | H | H | H | $R^{38} = R^{43} = N(CH_3)_2$ |
| XII-41 | Ph | Ph | Ph | H | H | H | H | $R^{38} = R^{43} = Cl$ |
| XII-42 | Ph | Ph | Ph | H | H | H | H | $R^{37} = R^{43} = CH_3$ |
| XII-43 |  |  | Ph | H | H | H | H | H |
| XII-44 |  |  | Ph | H | H | H | H | H |

TABLE 12-continued
| | | | | | | |
|---|---|---|---|---|---|---|
| XII-45 | 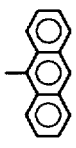 |  | Ph | H | H | H | H |
| XII-46 |  |  | Ph | H | H | H | H |
| XII-47 | 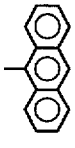 | 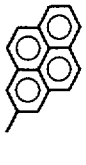 | Ph | H | H | H | H |
| XII-48 |  |  | Ph | H | H | H | H |

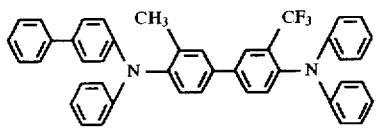
XIII-1

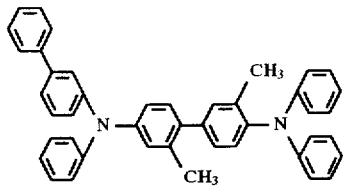
XIII-2

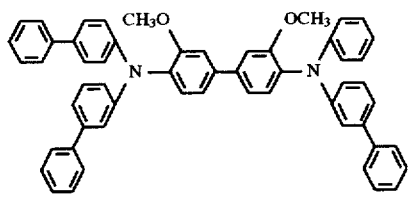
XIII-3

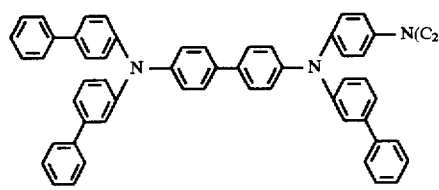
XIII-4

The inventive compounds can be synthesized by exactly or approximately the same method as described in Jean Piccard, Herr. Chim. Acta., 7, 789 (1924) and Jean Piccard, J. Am. Chem. Soc., 48, 2878 (1926). More particularly, they can be prepared by effecting Ullman reaction, that is, by heating a combination of a di(biphenyl)amine compound and a diiodobiphenyl compound, a combination of a N,N'-diphenylbenzidine compound and iodobiphenyl compound or a similar combination in the presence of copper. These compounds can be identified by elemental analysis, infrared absorption spectroscopy (IR), nuclear magnetic resonance spectroscopy (proton NMR), etc.

In general, the inventive compounds have a molecular weight of about 640 to about 2,000, a high melting point of about 190° to about 300° C., and a high glass transition temperature (Tg) of about 80° to about 200° C. By conventional vacuum deposition or the like, they form a transparent, smooth film of quality which maintains a stable amorphous state even above room temperature and over a long period of time. Some of the inventive compounds do not have a melting point and remain amorphous at elevated temperatures. Without a need for binder resin, the inventive compounds can be formed into a thin film by themselves.

The inventive compounds may be used alone or in admixture of two or more.

The organic EL element of the invention includes at least one organic compound layer. The organic compound layer or at least one of organic compound layers contains the inventive compound. One exemplary structure of the organic EL element according to the present invention is shown in FIG. 1. The EL element generally designated at 1 in FIG. 1 includes on a substrate 2, an anode 3, a hole injecting and transporting layer 4, a light emitting layer 5, an electron injecting and transporting layer 6, and a cathode 7 stacked in the described order from bottom to top.

The light emitting layer has multi-functions of injecting holes and electrons, transporting them, and recombining holes and electrons to create excitons. A relatively electronically neutral compound is preferably used in the light emitting layer. The hole injecting and transporting layer has functions of facilitating injection of holes from the anode, transporting them, and obstructing electron transportation. The electron injecting and transporting layer has functions of facilitating injection of electrons from the cathode, transporting them, and obstructing hole transportation. These two layers are effective for increasing the number of holes and electrons injected into the light emitting layer and confining holes and electrons therein for optimizing the recombination region to improve light emission efficiency. Therefore the hole and electron injecting and transporting layers are optionally provided by taking into account the magnitude of the respective functions of the compound used in the light emitting layer for electron injection and transportation and hole injection and transportation. For example, if the compound used in the light emitting layer has an enhanced hole or electron injecting and transporting function, the hole or electron injecting and transporting layer may be omitted because the light emitting layer itself can also serve as a hole or electron injecting and transporting layer. In some cases, both the hole and electron injecting and transporting layers may be omitted. Each of the hole and electron injecting and transporting layers may consist of two sublayers, one sublayer having an injection function and another sublayer having a transporting function.

The thicknesses of the light admitting layer, hole injecting and transporting layer, and electron injecting and transporting layer are not critical and varies with a particular formation technique. Usually a single layer is about 5 to 1,000 nm thick, especially about 10 to 200 nm.

The thicknesses of he hole injecting and transporting layer and electron injecting and transporting layer are equal to or range from 1/10 to 10 times the thickness of the light emitting layer although they depend on the design of a recombination/light emitting region. When the electron or hole injecting and transporting layer is divided into an injection layer and a transporting layer, preferably the injection layer is at least 1 nm thick and the transporting layer is at least 20 nm thick. The upper limit of thickness is about 100 nm for the injection layer and about 1,000 nm for the transporting layer. These film thickness ranges also apply when two (first and second) injecting and transporting layers are formed.

A freedom of design of the recombination/light emitting region is available by controlling the film thicknesses in consideration of the carrier mobility and carrier density (which is dependent on ionization potential and electron affinity) of the light emitting layer, hole injecting and transporting layer, and electron injecting and transporting layer to be combined. This enables free design of luminous color, control of the luminance and spectrum of light emission by the interference of the electrodes, and control of the space distribution of light emission.

The inventive compound is applicable to either a light emitting layer or a hole injecting and transporting layer. Preferably the inventive compound is used in a hole injecting and transporting layer because it excels in hole injecting and transporting ability.

Described below is the preferred embodiment wherein the inventive compound is used in a hole injecting and transporting layer. The hole injecting and transporting layer may be formed by evaporating the inventive compound or by dispersing the inventive compound in a resin binder and coating the dispersion. Especially by evaporation, a satisfactory amorphous film is deposited.

Any of various organic compound used in conventional organic EL elements, for example, the organic compounds described in JP-A 295695/1988, 191694/1990, and 000792/1991 may be concomitantly used in the hole injecting and transporting layer. For example, any of aromatic tertiary amines other than the inventive compounds, hydrazone derivatives, carbazole derivatives, triazole derivatives, imidazole derivatives, oxadiazole derivatives having an amino group, and polythiophenes may be used in a layered or mixed manner along with the inventive compound.

Where the hole injecting and transporting layer is formed as comprising a hole injecting layer and a hole transporting layer, two or more compounds are selected in a proper combination from the compounds commonly used in hole injecting and transporting layers, in this regard, it is preferred to laminate layers such that a layer of a compound having a lower ionization potential may, be disposed adjacent to the anode (ITO etc.). It is also preferred to use a compound having better thin film forming ability at the anode surface. This order of lamination also applies where a plurality of hole infecting and transporting layers are provided. Such an order of lamination is effective for lowering drive voltage and preventing current leakage and development and growth of local dark spots. Since evaporation is utilizable in manufacturing elements, thin films of about 1 to 10 nm thick can be formed uniform and pinhole-free. This restrains any change in color tone of light emission and a drop of efficiency by re-absorption even if a compound having a low ionization potential and absorption in the visible range is used in the hole injecting and transporting layer.

Polythiophene is a preferred organic compound to be combined wig the hole injecting and transporting layer containing the inventive compound as a major component. From the standpoint of ionization potential, it is recommended to deposit by evaporation polythiophene on an anode as a hole injecting layer or a first hole injecting and transporting layer of good thin film quality and then deposit the inventive compound thereto as a hole transporting layer or a second hole injecting and transporting layer.

The polythiophees which can be used in the invention include a polymer A having a structural unit of formula (28), a copolymer B having structural units of formulae (28) and (29), and a polymer C having a structural unit of formula (30).

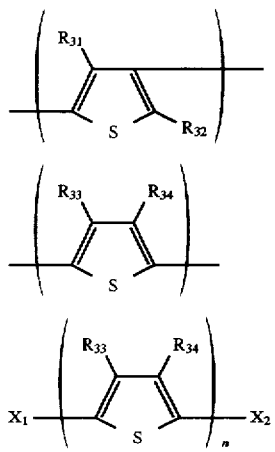

First thiophene polymer A is described. Polymer A has a structural unit of formula (28). For example, polymer A is represented by the following formula (31).

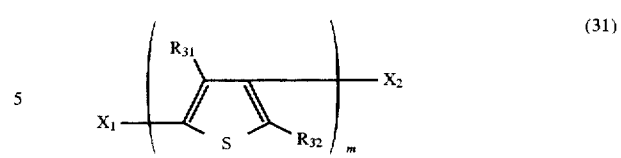

In formulae (28) and (31), each of $R_{31}$ and $R_{32}$ is a hydrogen atom, an aromatic hydrocarbon group or an aliphatic hydrocarbon group while $R_{31}$ and $R_{32}$ may be identical or different. The aromatic hydrocarbon groups represented by $R_{31}$ and $R_{32}$ may be substituted or substituted ones and preferably have 6 to 15 carbon atoms. Exemplary substituents, if any, are alkyl, alkoxy, amino and cyano groups. Exemplary aromatic hydrocarbon groups include phenyl, tolyl, methoxyphenyl, biphenyl and naphthyl groups. The aliphatic hydrocarbon groups represented by $R_{31}$ and $R_{32}$ include alkyl and cycloalkyl groups which may be substituted or unsubstituted ones. Preferred are those groups having 1 to 6 carbon atoms, for example, methyl, ethyl, i-propyl and t-butyl groups. Preferably $R_{31}$ and $R_{32}$ are hydrogen atoms or aromatic hydrocarbon groups, with hydrogen being most preferred.

Polymer A in the layer has an average degree of polymerization, represented by m in formula (31), of 4 to 100, preferably 5 to 40, more preferably 5 to 20. Polymer A may be either a homopolymer consisting of identical recurring units of formula (28) or a copolymer consisting essentially of recurring units of formula (28) having different combinations of $R_{31}$ and $R_{32}$. The copolymer may be any of random, alternate and block copolymers. Polymer A in the layer preferably has a weight average molecular weight of about 300 to about 10,000.

Polymer A is terminated with terminal groups, represented by $X_1$ and $X_2$ in formula (31), which are hydrogen atoms or halogen atoms such as chlorine, bromine and iodine. The terminal groups introduced generally depend on the starting material from which polymer A is synthesized. Alternatively, a suitable substituent may be introduced at the final stage of polymerization reaction.

Preferably polymer A consists of structural units of formula (28) although it may contain less than 10 mol % of another monomeric component.

Some illustrative, preferred examples of polymer A are shown below by picking up the combination of $R_{31}$ and $R_{32}$ in formula (28) or (31).

TABLE 13

| | Polymer A | | |
|---|---|---|---|
| Polymer | $R_{31}$ | $R_{32}$ | |
| A-1 | H | H | homopolymer |
| A-2 | H | Ph | homopolymer |
| A-3 | Ph | H | homopolymer |
| A-4 | Ph | Ph | homopolymer |
| A-5 | H | $CH_3$ | homopolymer |
| A-6 | H | $t-C_4H_9$ | homopolymer |

Next thiophene copolymer B is described copolymer B has structural units of formula (28) and (29). For example, copolymer B is represented by the following formula (32).

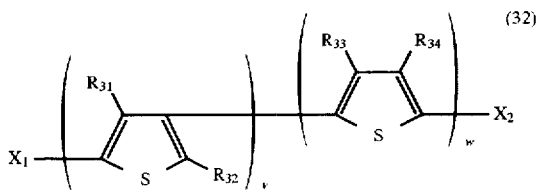

Formula (28) is as defined above. Then in formula (32), $R_{31}$ and $R_{32}$ are as defined above for formula (28).

In formulae (29) and (32), each of $R_{33}$ and $R_{34}$ is a hydrogen atom, an aromatic hydrocarbon group or an aliphatic hydrocarbon group while $R_{33}$ and $R_{34}$ may be identical or different. Examples of the aromatic and aliphatic hydrocarbon groups represented by $R_{33}$ ad $R_{34}$ are the same as enumerated for $R_{31}$ and $R_{32}$, with their preferred examples being also the same. Further $R_{33}$ and $R_{34}$ to together may form a ring which is fused to the thiophene ring. A benzene ring is a typical fused ring.

Like polymer A, copolymer B in the layer has an average degree of polymerization, represented by v +w in formula (32), of 4 to 100, preferably 5 to 40, more preferably 5 to 20. The molar ratio of the structural unit of formula (28) to the structural unit of formula (29) may range from about 10/1 to about 1/10. Copolymer 3 in the layer, preferably has a weight average molecular weight of about 300 to about 10,000.

Copolymer B is terminated with terminal groups, represented by $X_1$ and $X_2$ in formula (32), which are hydrogen atoms or halogen atoms as in polymer A. The terminal groups generally depend on the starting materials from which copolymer B is synthesized.

Preferably copolymer B consists of structural units of formulae (28) and (29) although it may contain less than 10 mol % of another monomeric component. Copolymer B may be any of random, alternate and block copolymers, which are all encompassed by the structural formula (32). The structural units of each of formulae (28) and (29) may be identical or different.

Some illustrative, preferred examples of copolymer B an shown below by picking up the combination of $R_{31}$, $R_{32}$, $R_{33}$ and $R_{34}$ in formula (32).

TABLE 14

| Copolymer | Copolymer B | | | |
|---|---|---|---|---|
| | $R_{31}$ | $R_{32}$ | $R_{33}$ | $R_{34}$ |
| B-1 | H | H | H | H |
| B-2 | H | $CH_3$ | H | H |
| B-3 | H | Ph | H | H |
| B-4 | H | Ph | Ph | Ph |

Next thiophene polymer C is described. Polymer C is represented by formula (30) wherein $R_{33}$ and $R_{34}$ are as defined for formula (29), with their preferred examples being also the same.

$X_1$ and $X_2$ represent terminal groups and may be either identical or different. Like the terminal groups of polymer A and copolymer B, the terminal groups represented by $X_1$ and $X_2$ are hydrogen atoms or halogen atoms such as chlorine, bromine and iodine. The terminal groups $X_1$ and $X_2$ generally depend on the starting material from which polymer C is synthesized.

Like polymer A and copolymer B, polymer C in the layer has an average degree of polymerization, represented by n in formula (30), of 4 to 100, preferably 5 to 40, more preferably 5 to 20. Polymer C may be either a homopolymer consisting of recurring units having an identical combination of $R_{33}$ and $R_{34}$ or a copolymer consisting essentially of recurring units having different combinations of $R_{33}$ and $R_{34}$. The copolymer may be any of random, alternate and block copolymers. Polymer C in the layer preferably has a weight average molecular weight of about 300 to about 10,000.

Preferably polymer C is of the structure shown by formula (30) although it may contain less than 10 mol % of another monomeric component like polymer A and copolymer B.

Some illustrative, preferred examples of polymer C are shown below by picking up the combination of $R_{33}$ and $R_{34}$ in formula (30).

TABLE 15

| | Polymer C | | |
|---|---|---|---|
| Copolymer | $R_{33}$ | $R_{34}$ | |
| C-1 | H | H | homopolymer |
| C-2 | H | Ph | homopolymer |
| C-3 | Ph | Ph | homopolymer |
| C-4 | H | 4-methoxyphenyl | homopolymer |
| C-5 | $CH_3$ | $CH_3$ | homopolymer |
| C-6 | H | $CH_3$ | homopolymer |

In the practice of the invention, use of a polythiophene in the form of polymer C is most preferred. Polythiophenes may be used alone or in admixture of two or more.

The polythiophenes used herein have a melting point of higher than 300° C. and some have no melting point. They can be evaporated and deposited in vacuum to form amorphous or microcrystalline thin films of quality.

In the above-mentioned embodiment: wherein the inventive compound is used in the hole injecting and transporting layer, the light emitting layer contains a fluorescent or luminescent material which is a compound having a light emitting function. The fluorescent or luminescent material may be selected from compounds as disclosed in JP-A 264692/1988, for example, quinacridone, rubrene, and styryl dyes alone or in admixture. Other useful examples include metal complex dyes such as tris(8-quinolinolato)aluminum, tetraphenylbutadiene, anthracene, perylene, coronene, and 12-phthaloperinone derivatives. By evaporating the organic fluorescent or luminescent material or by dispersing it in a resin binder and coating the dispersion, a light emitting layer is formed to a predetermined thickness.

For the electron injecting and transporting layer, there may be used organic metal complex derivatives such as tris(8-quinolinolato)aluminum, oxadiazole derivatives, perylene quinoline derivatives, quinoxaline derivatives, diphenylquinone derivatives, and nitro-substituted fluorene derivatives. In an embodiment wherein the electron injecting and transporting layer also serves as a light emitting layer, use of tris(8-quinolinolato)aluminum is preferred. Like the hole injecting and transporting layer and light emitting layer, the electron injecting and transporting layer may be formed by evaporation.

Where the electron injecting and transporting layer is fodred as comprising an electron injecting layer and an electron transporting layer, two or more compounds are selected in a proper combination from the compounds commonly used in electron injecting and transporting layers. In this regard, it is preferred to laminate layers such that a layer of a compound having a greater electron affinity may be disposed adjacent to the cathode. This order of lamination also applies where a plurality of electron injecting and transporting layers are provided.

The organic compound layer may further contain a single oxygen quencher. Exemplary quechers include rubrene, nickel complexes, diphenylisobenzofuran, and tertiary amines, with the rubrene being preferred. When combined with the inventive compound, the quencher may be present in an amount of less than 10 mol % of the inventive compound.

In okn preferred embodiment of the present invention, the organic cold layer or layers are preferably doped with rubrene. Doping may be carried out throughout the organic compound layer, preferably throughout the hole injecting and transporting layer. It is believed preferable that rubrene be present in a carrier recobination region, a light emitting region and the proximity thereof, for example, the interface of an organic compound layer in contact with a hole injecting and transporting layer. Then doping need not necessarily be carried out throughout the hole injecting and transporting layer. Therefore doping may be limited to a half area of the hole injecting and transporting layer which is disposed adjacent to the light emitting layer (which may also serve as an electron injecting and transporting layer) or the electron injecting and transporting layer (where the hole injecting and transporting layer also serves as a light emitting layer) although doping is generally carried out throughout the hole injecting and transporting layer. In some cases, doping may be carried out throughout the hole injecting and transporting layer or a half area of the hole injecting a transporting layer which is disposed adjacent to the light emitting layer or the electron injecting and transporting layer and a half region of the light emitting layer or electron injecting and transporting layer which is disposed adjacent to the hole injecting and transporting layer. Combined use of the inventive compound and rubrene is preferred particularly in the hole injecting and transporting layer.

The doping concentration of rubrene is preferably about 0.1 to 500 by weight, more preferably about 0.1 to 30% by weight, most preferably about 0.1 to 20%; by weight of the entire layer to be doped because higher concentrations of rubrene can cause concentration quenching.

Besides rubrene, it is alo contemplated to dope with other fluorescent or luminescent materials.

In one preferred embodiment of the invention, interposed between a layer containing the inventive compound and a layer contains a compound having another function is a mix layer containing a mixture of both the compounds, especially as a light emitting layer. For enhancing luminous intensity, the mix layer may be doped with a compound having a light emitting function (or fluorescent or luminescent material).

Since the inventive compound has a hole injecting Me transporting function, it is especially preferred to provide a mix layer containing a mixture of the inventive compound and a compound having an electron injecting and transporting function (inclusive of a compound further having a light emitting function) as a light emitting layer. The compound having an electron injecting and transporting function used in this mixture may be selected from the previously mentioned compounds for electron injection and transportation. Specifically use of tris(8-quinolinolato)aluninum is preferred.

In the mix layer, the compounds having a hole or electron injecting and transporting function may be used alone or in admixture of two or more. The compound having a hole injecting and transporting function used in this mixture may be selected from the previously mentioned compounds for hole injecting and transporting as well as the inventive compounds.

In one especially preferred structure, a hole injecting and transporting layer containing the inventive compound is disposed on a hole injecting and transporting layer containing polythiopheze, and a mix layer containing a mixture of the inventive compound and a compound having an electron injecting and transporting function is interleaved between the hole and electron injecting and transporting layers as a light emitting layer.

With respect to the mix ratio, which depends on carrier mobility, it is preferred that the inventive compound occupies about 30 to 70%, more preferably about 40 to 60%, especially about 50% by weight of the mix layer. Differently stated, the weight ratio of the inventive compound to the compound having an electron injecting and transporting function preferably ranges from about 30/70 to 70/30, more preferably from about 40/60 to 60/40, especially about 50/50.

The thickess of the mix layer preferably ranges from the thickness corresponding to a single molecule layer to less than the thickness of an organic compound layer. More particularly the mix layer has a thickness of from about 1 to about 85 nm, =ere preferably about 5 to 60 nm, most preferably about 5 to 50 nm.

Preferably the mix layer is formed by co-deposition, that is, by simultaneously evaporating the compounds from distinct sources. If both the compounds have equal or close vapor pressure or evaporation temperature, they may be pre-mixed in a common evaporation boat, from which they are evaporated together. In the mix layer, preferably both the compounds are uniformly mixed although the compounds can be present in island form.

It is to be noted that the mix layer may also be used as an organic compound layer other than the light emitting layer. However, it is preferred that the mix layer for part of organic compound layers included in the element. If all the organic compound layers are mix layers, the element sometimes fails to provide uniform light emission at high luminance.

In the preferred embodiment, the inventive compound is used in the hole injecting and transporting layer as mentioned above. The difference in ionization potential Ip between the hole injecting and transporting layer and a light emitting layer disposed adjacent thereto (which may also serve as electron injecting and transporting layer) should preferably be at least 0.25 eV, especially 0.25 to 0.40 eV. It is understood that where a layer containing the inventive compound is a layer having a hole injecting and transporting function and also serving as a light emitting layer, the layer disposed adjacent thereto is a electron injecting and transporting layer, and accordingly the difference in ionization potential Ip in this case is that between the layer containing the inventive compound and the electron injecting and transporting layer. Note that the inventive compounds have an ionization potential Ip of about 5.0 to 5.4 eV in absolute value.

It is to be noted that the ionization potential Ip is determined by evaporating a compound onto a glass substrate having an ITO transparent electrode or slide glass to form a compound mono-layer film of about 10 to 200 nm thick and measuring the ionization potential of the sample film by means of a low energy electron spectrometer Surface Analyzer model AC-1 manufactured by Riken Kiki Co., Ltd. according to Shirahashi, Isobe & uda, Electronic Parts and Materials, 123 (1985).

Figure 2:
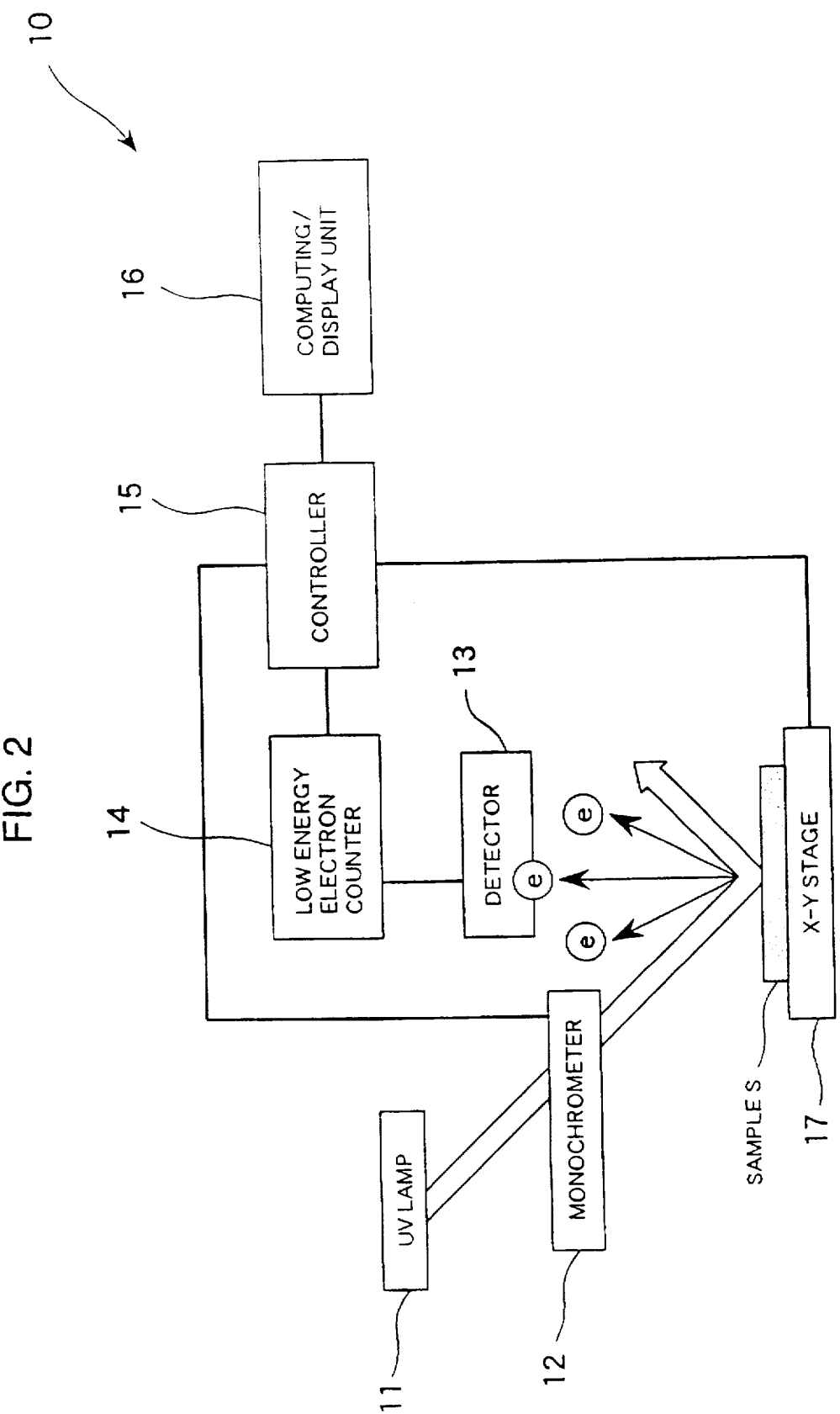
FIG. 2 is a block diagram showing a low energy electron spectrometer system.

FIG. 2 shows the construction of the low energy electron spectrometer system. The spectrometer generally designated at 10 includes a ultraviolet lamp 11, a monochrometer 12, a detector 13, a low energy electron counter 14, a controller 15, a computing/display unit 16, and an X-Y stage 17. On measurement, a sample S rests on the X-Y stage 17.

Figure 3:
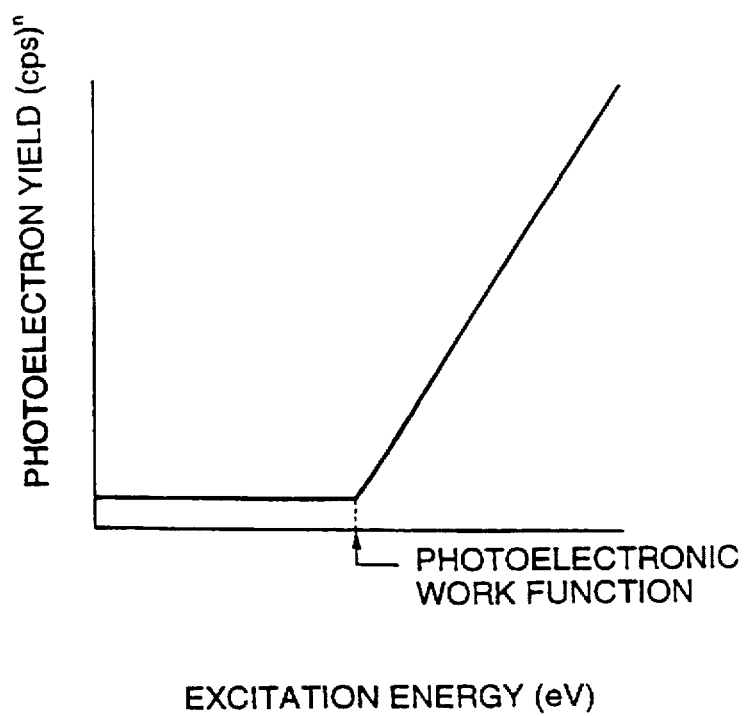
FIG. 3 is a graph showing a photoelectron yield as a function of excitation energy.

The UV lamp 11 in the form of a deuterium discharge lamp emits UV radiation toward the monochrometer 12 through which a light beam having a wavelength of 200 to 360 nm is passed and directed to the surface of the sample S. The light beam having a wavelength of 200 to 360 nm has energy of 6.2 to 3.4 eV as converted according to the equation: $E=hv=h(c/\lambda)$ wherein E is an energy, h is Planck's constant, v is a frequency, and $\lambda$ is a wavelength. When the light is swept from a lower excitation energy level to a higher excitation energy level, electron emission due to the photoelectric effect starts at a certain energy level. This energy level is generally known as a photoelectric work function. The thus emitted photoelectrons are detected and counted by the detector 13 and the low energy electron counter 14. The count is subject to arithmetic operations including a background correction and a correction for a count loss during a dead time and then displayed on the display unit 16 for indicating an electron emission as a function of excitation energy (basic characteristic) as shown in FIG. 3. As seen from the basic characteristic, the relationship between the photoelectron yield (count per second, cps) and the excitation energy (eV) is linear provided that a factorial of photoelectron yield (cps)$^n$ is on the ordinate and the excitation energy is an the abscissa. The value of n is generally ½. The controller 15 serves for wavelength driving of the monochrometer 12, control of the sample position on the X-Y stage 17, and count control of the low energy electron counter 14.

Therefore, the photoelectron work function obtained from FIG. 3 is the ionization potential Ip used herein.

Where a layer containing the inventive compound further contains another compound, the ionization potential Ip of this layer is regarded equal to the ionization potential Ip measured from a single layer film of the inventive compound if the inventive compound is a major component (typically having a content of more than 50% by weight). Where a layer to be compared with the inventive compound-containing layer contains two or more compounds, the ionization potential Ip of this layer is regarded equal to the ionization potential Ip measured from a single layer film of the primary compound constituting the majority (typically having a content of more than 50% by weight).

As a general rule, the absolute value of ionization potential Ip of a single layer film of the inventive compound is lower than that of a compound to be compared therewith.

It should be understood that the concept of ionization potential is not applicable to the arrangement wherein a mix layer is interposed between the relevant layers.

In the practice of the invention, the cathode is preferably made of a material having a low work function, for example, Li, Na, ZV, Al, Ag, In and alloys containing at least one of those metals. The cathode should preferably be microcrystalline, especially amorphous. The cathode is preferably about 10 to 1,000 nm thick.

In order that the EL element produce plane light emission, at least one of the electrodes should be transparent or semi-transparent. Since the material of the cathode is limited as mentioned just above, it is preferred to select the material and thickness of the anode so as to provide a transmittance of at least 80% to Me emitted radiation. For example, the anode is preferably made of indium tin oxide (ITO), $SnO_2$, Ni, Au, Pt, Pd, and doped polypyrrole. The anode preferably has a thickness of about 10 to 500 nm. In order that the element be more reliable, the drive voltage should be low. For example, ITO having 10 to 30 $\Omega/cm^2$ is preferred.

The substrate may be made of any desired material although a transparent or semi-transparent material such as glass and resins is used in the illustrated embodiment wherein light exits from the substrate side. The substrate may be provided with a color or fluorescent filter film, a color-conversion film or layer or dielectric reflecting film for controlling emission light color. Where the substrate is made of an opaque material, the layer stacking order may be reversed from that shown in FIG. 1.

Next, it is described how to prepare the organic EL element using the inventive compound. The cathode and anode are preferably formed by gas phase deposition techniques such as vacuum evaporation and sputtering. The light emitting layer and hole and electron injecting and transporting layers are preferably formed by vacuum evaporation because homogeneous thin films are available. By utilizing vacuum evaporation, there is obtained a homogeneous thin film which is amorphous or has a grain size of less than 0.1 μm. The lower limit of grain size is generally about 0.001 μm. If the grain size is more than 0.1 μm, uneven light emission takes place and the drive voltage of the element must be increased with a substantial lowering of electric charge injection efficiency.

The conditions for vacuum evaporation are not critical although a vacuum of $10^{-3}$ Pa or lower and an evaporation rate of about 0.1 to 1 nm/sec. are preferred. It is preferred to successively form layers in vacuum because the successive formation in vacuum can avoid adsorption of impurities at the interface between the layers, thus ensuring high quality and a lower drive voltage.

In th embodiment wherein the respective layers are formed by vacuum evaporation, where it is desired for a single layer to contain two or more compounds, boats having the compounds received therein are individually temperature controlled to achieve co-deposition. It is also acceptable to evaporate a pre-mix of two or more compounds. Also employable are solution coating techniques such as spin coating, dipping and casting and Langmuir-Blodgett'S technique. For the solution coating, the inventive compound may be dispersed in a matrix material such as a polymer.

The organic EL element of the invention is generally of the DC drive type while it can be of the AC or pulse drive type. The applied voltage is generally about 2 to 20 volts.

It is understood that the inventive compounds are also applicable as organic semiconductor materials having donor property to photo-electric transducer elements other than the organic EL element, for example, photo-cells and photo-sensors. They are also useful as thermochromic materials utilizing transition between amorphous and crystalline states.

EXAMPLE

Examples of the present invention are given below by way of illustration and not by way of limitation. Herein "mp" is a melting point and "Tg" is a glass transition temperature.

Example 1

Synthesis of N,N,N',N'-tetra(3-biphenylyl)benzidine, compound No. I-1

A 2-1atmospheric hydrogenation reactor was charged with 250 g (1.26 mol) of m-nitrobiphenyl, 12.5 q of 5% Pd-Cl, and 1250 ml of ethanol. A theoretical amount of hydrogen gas was absorbed at room temperature. The catalyst was removed by filtration and the filtrate was distilled of the solvent, obtaining 212 g of m-aminobiphenyl (yield 99.9%). Another batch of reaction was effected on the same scale except that 254 g (1.28 mol) of m-nitrobiphenyl was used, obtaining 215 g of m-aminobiphenyl (yield 99.7%).

A 10-1 reactor was charged with 775 m. of conc. hydrochloric acid, 775 ml of water, and 775 g of ice, and 125 g (0.740 mol) of m-aminobiphenyl was sided therein. To the reactor maintained below 0° C., 750 ml of an aqueous solution of 56.3 g (0.816 mol) sodium nitrite was added dropwise over 30 minutes and stirring was continued for a further 50 minutes at the temperature. To the resulting diazonium salt aqueous solution maintained below 0° C., 1250 ml of an aqueous solution of 185 g (1.12 mol) potassium iodide was added dropwise over one hour. After addition, stirring was continued for one hour at the temperature and then for 2 hours at room temperature.

The reaction solution was extracted with ethyl acetate. The organic layer was washed with water, dried over magnesium sulfate, and distilled of the solvent, obtaining a crude crystal. Another batch of reaction was effected on the same scale. The resulting crude crystals were combined together and purified through a silica gel column with n-hexane, obtaining 297 g of m-iodobiphenyl (yield 71.7% for the two batches combined).

A 2-1 reactor was charged with 140 g (0.828 mol) of maminobiphenyl, 232 g (0.829 mol) of m-iodobipheyl, 63.1 g (0.457 mol) of potassium carbonate, 13.9 g of copper powder, and 800 ml of nitrobenzene. In an argon stream, the contents were heated under reflux for 32 hours. At the end of reaction, the insoluble was removed by filtration and the filtrate was distilled of the solvent. The still residue was purified through a silica gel column with a 4/1 mixture of n-hexane and toluene, obtaining 44.5 g of di(3-biphenyl) amine of high purity (yield 16.7%).

A 500-ml reactor was charged with 44.5 g (0.139 mol) of di(3-biphenyl)amine, 27.6 g (0.0680 mol) of 4,4'-diiodobiphenyl, 34.3 g (0.249 mol) of potassium carbonate, 2.3 g of copper powder, and 180 ml of nitrobenzene. In an argon stream, the contents were heated under reflux for 24 hours. At the end of reaction, the insoluble was removed by filtration and the filtrate was distilled of the solvent. The still residue was purified through a silica gel column with a 3/1 mixture of n-hexane and toluene, obtaining 30 g of N,N,N', N'-tetra(3-biphenylyl)benzidine of primary purity grade (yield 55.7%). It was further purified by recrystallization from toluene, obtaining 6.0 g of a 99.58% pure fraction and 5.0 g of a 99.23% pure fraction (combined yield 20.496). Further purification by sublimation yielded 8.0 g of a 99.99% pure product.

mass analysis; m/e 792 (M⁺).

Figure 4:
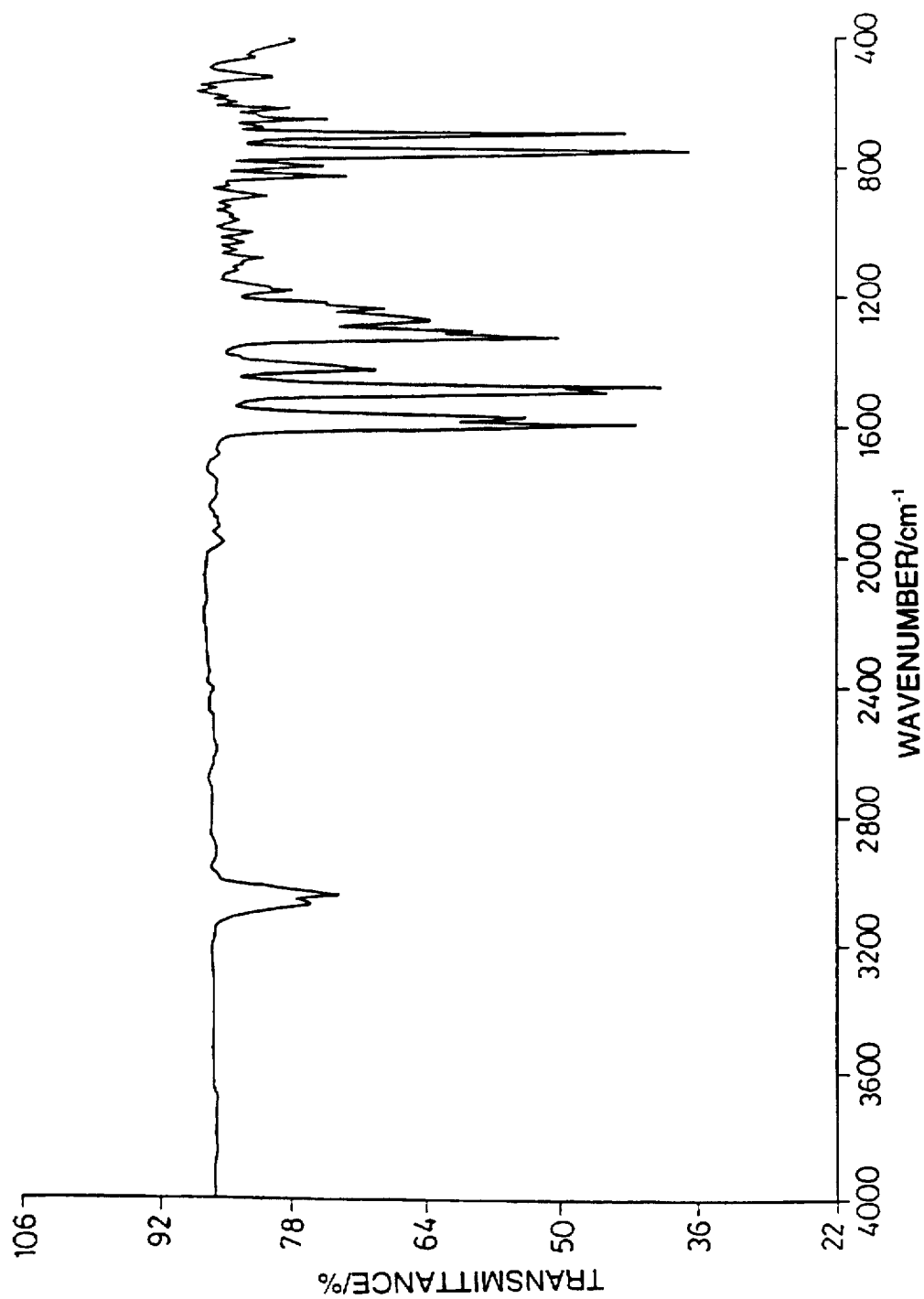
FIG. 4 is a diagram showing a IR absorption spectrum of the inventive compound (I-1) of Example 1.

IR absorption spectrum FIG. 4.

Figure 5:
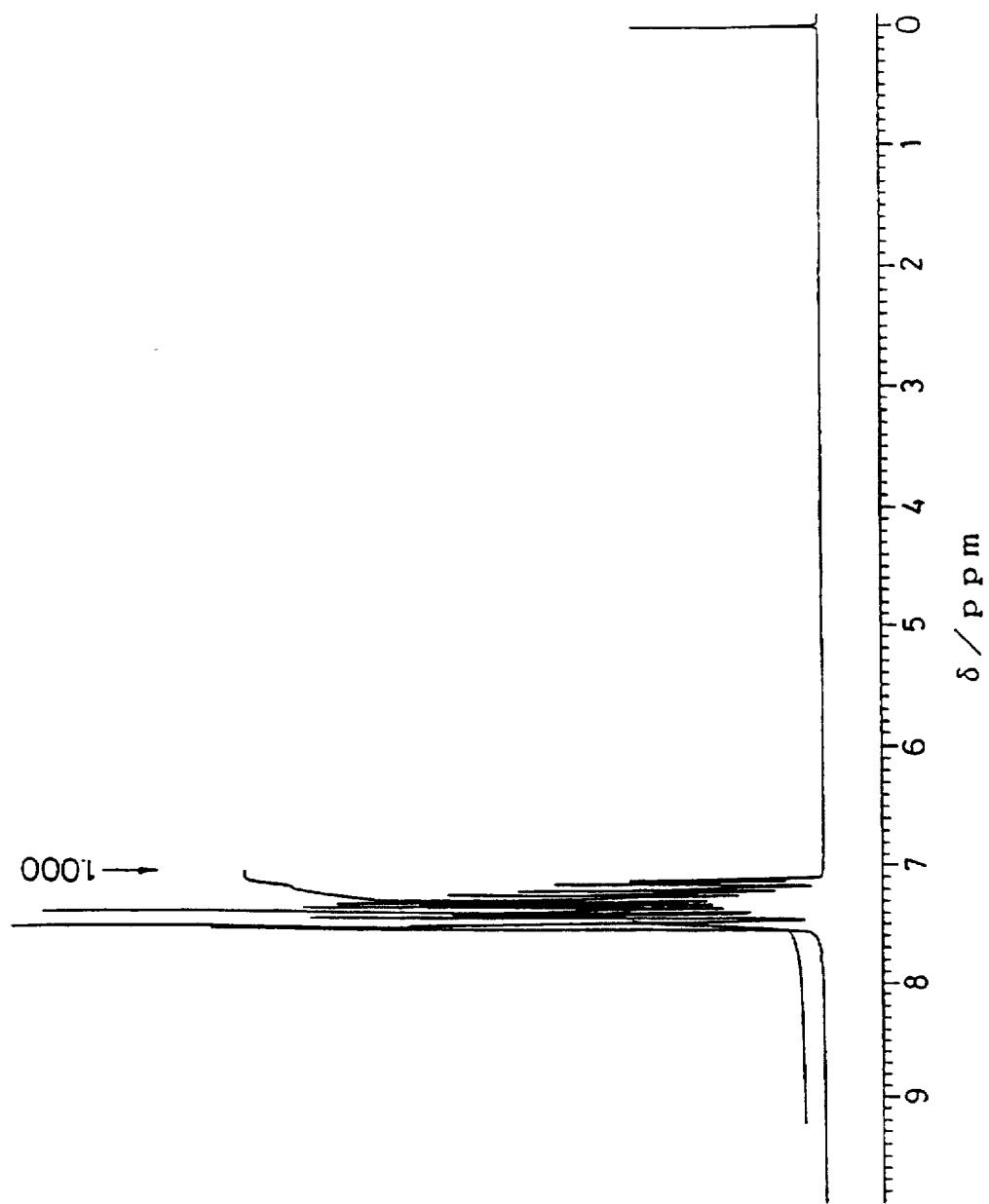
FIG. 5 is a diagram showing a NMR spectrum of compound (I-1).

NM spectrum; FIG. 5.

Differential scanning calorimetry (DSC): mp 207.4° C. Tg 95. 8° C.

Example 2

Synthesis of N,N,N',N'-tetra(4-biphenyl)berizidine, compound No. II-1

A reactor was charged with 72.5 g (0.429 mol) of 4-aminobiphenyl, 120 g (0.429 mol) of 4-iodobiphonyl, 32.6 g (0.236 mol) of potassium carbonate, 6.8 g (0.107 mol) of copper, and 430 ml of nitrobezene. Reaction was effected overnight at 210° C. At the end of reaction, the reaction solution was allowed to cool down, the copper salts were removed by vacuum filtration, and the filtrate was washed with chloroform and vacuum distilled of the solvent. To the residue was added 500 ml of methanol. On cooling, crystals precipitated and were recovered by filtration. The thus recovered crystals, 49 g, was dissolved in 250 ml of dimnethylfoxmamide (DMF) with heating. The solution was cooled with water for allowing tribiphenylamine by-product to precipitate, which was removed by filtration. The filtrate was poured into 1000 ml of water for allowing crystals to precipitate. The precipitate was recovered by filtration and washed with water and t with methanol.

The thus obtained wet crystals, 35 g, were recrystallized from 750 ml of toluene, obtaining di(4-biphenyl)amine in yellowish green flake crystal form. The mother liquor was concentrated to recover secondary crystals. The combined amount was 19 g (yield 13.8%).

A reactor was charged with 15 g (0.0467 mol) of di(4-biphenyl)amine, 9.5 g (0.0234 mol) of 4,4'-diiodobiphenyl, 9.7 g (0.0702 mol) of potassium carbonate, 0.74 g (0.0117 mol) of copper, and 76 ml of nitrobenzens. Reaction was effected for two days at 220° C. At the end of reaction, 750 ml of DMF was added to the reaction solution, from which the copper salts were removed by filtration while hot. The filtrate was cooled down and the precipitating crystals were recovered by filtration. The thus obtained wet crystals, 25 g, were recrystallized three times from a 100-fold volume of toluene, obtaining 9 g of the end product, N,N,N',N'-tetra (4-biphenylyl)benzidine in pale yellow crystal form (yield 48.6%). Further purification by sublimation yielded a 99.99% pure product.

mass analysis: m/e 792 (M⁺).

Figure 6:
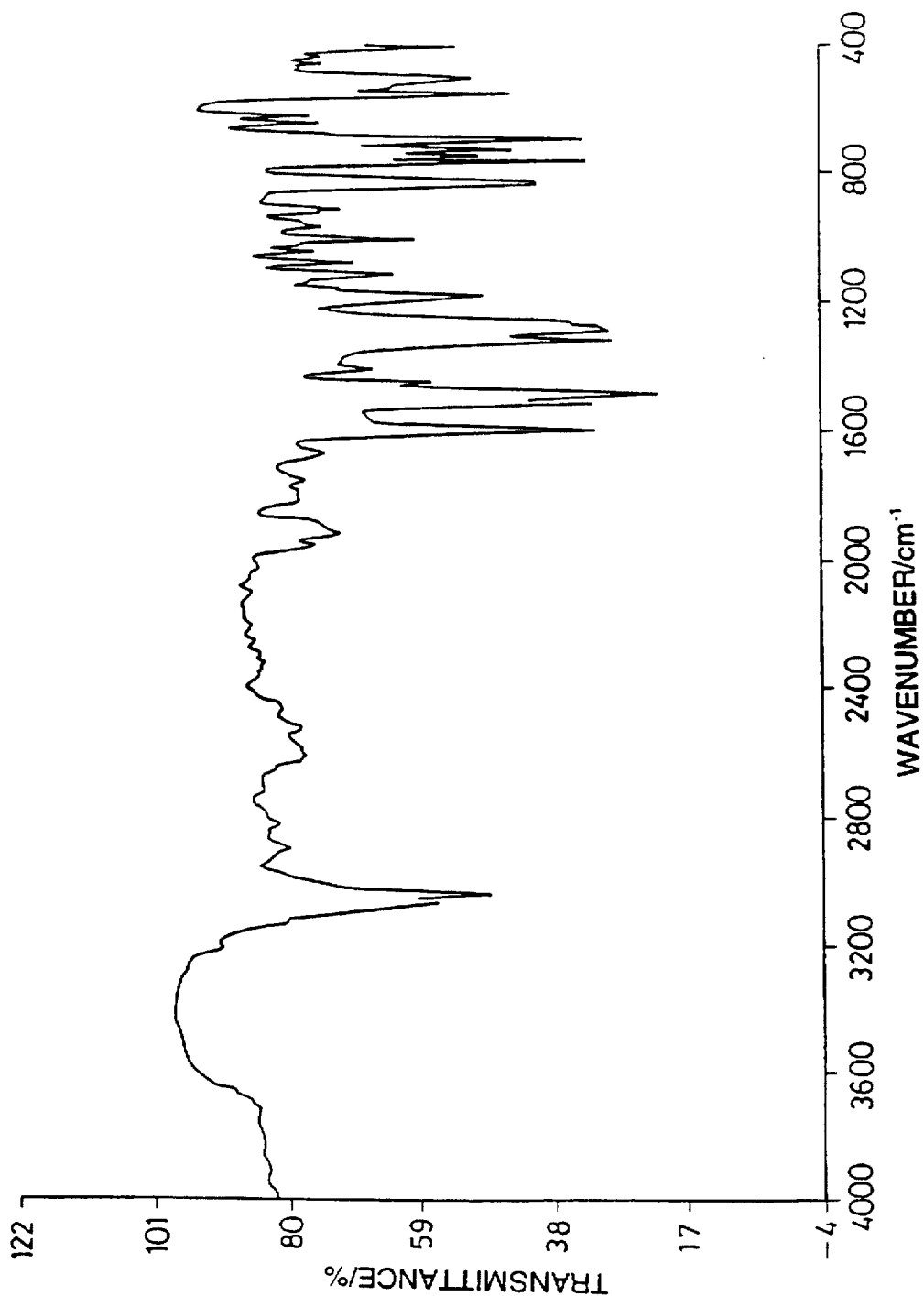
FIG. 6 is a diagram showing a IR absorption spectrum of the inventive compound (II-1) of Example 2.

IR absorption spectrum: FIG. 6.

Figure 7:
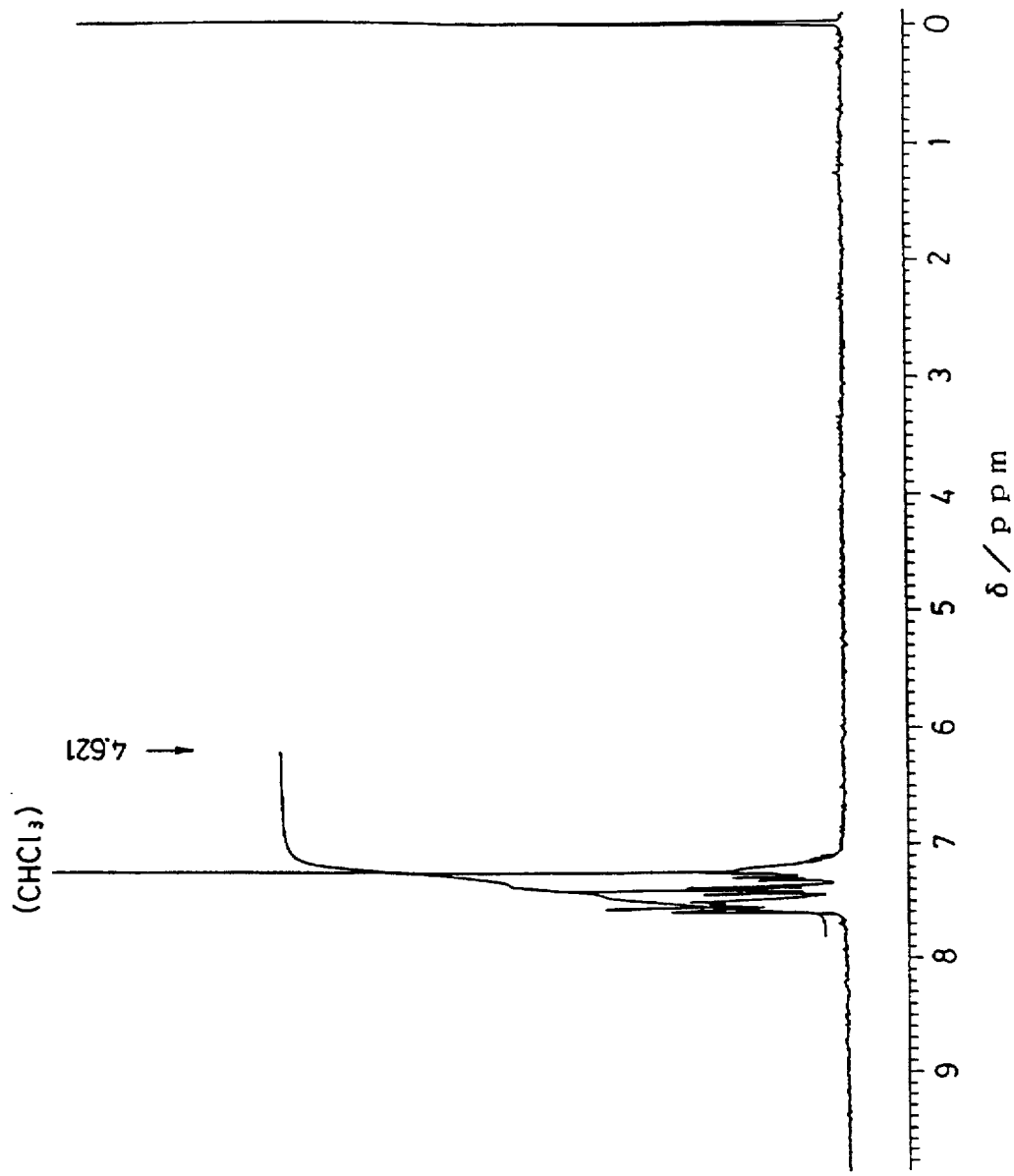
FIG. 7 is a diagram showing a NMR spectrum of compound (II-1).

NMR spectrum: FIG. 7.

DSC: mp 267.7° C. Tg 131.8° C.

Example 3

Synthesis of N,N'-diphezyl-N,N'-di(3-biphenylyl) benzidine, compound No. VII-1

A 10-1 reactor was charged with 155 ml of conc. hydrochloric acid, 155 ml of water, and 155 g of ice, and 25 g (0.148 mol) of m-aminobiphenyl was suspended therein. To the reactor maintained below 0° C., 150 ml of an aqueous solution of 11.3 g (0.164 mol) sodium nitrite was added dropwise over 30 minutes and stirring was continued for a further 50 minutes at the temperature. To the resulting diazonium salt aqueous solution maintained below 0° C., 250 ml of an aqueous solution of 37 g (0.223 mol) potassium iodide was added dropwise over one hour. After addition, stirring was continued for one hour at the temperature and then for 2 hours at room temperature.

The reaction solution was extracted with ethyl acetate. The organic layer was washed with water, dried over magnesium sulfate, and distilled of the solvent, obtaining a crude crystal. The crude crystal was purified through a silica gel column with n-hexane, obtaining 28 g of m-iodobiphenyl.

300-ml reactor was charged with 10 q (0.0298 mol) of N,N'-diphenylbenzidie, 25 g (0.0893 mol) of m-iodobiphenyl, 12.3 g (0.0891 mol) of potassium carbonate, 2.6 g of copper powder, and 150 ml of nitrobenzene. In an argon stream, the contents were heated under reflux for 24 hours. At the end of reaction, the insoluble was removed by filtration and the solvent was distilled off from the filtrate. The still residue was purified through a silica gel column with a 5/1 mixture of n-hexane and ethyl acetate, obtaining 15 g of N,N'-diphenyl-N,N'-di(3-biphenylyl) benzidine of primary purity grade (yield 78.89%. It was further purified by recrystallization from toluene and train sublimation, obtaining 10.6 g of a 99.9% pure product (yield 55.6%). Further purification by sublimation yielded a 99.99% pure product.

mass analysis: m/e 640 (M$^+$).

Figure 8:
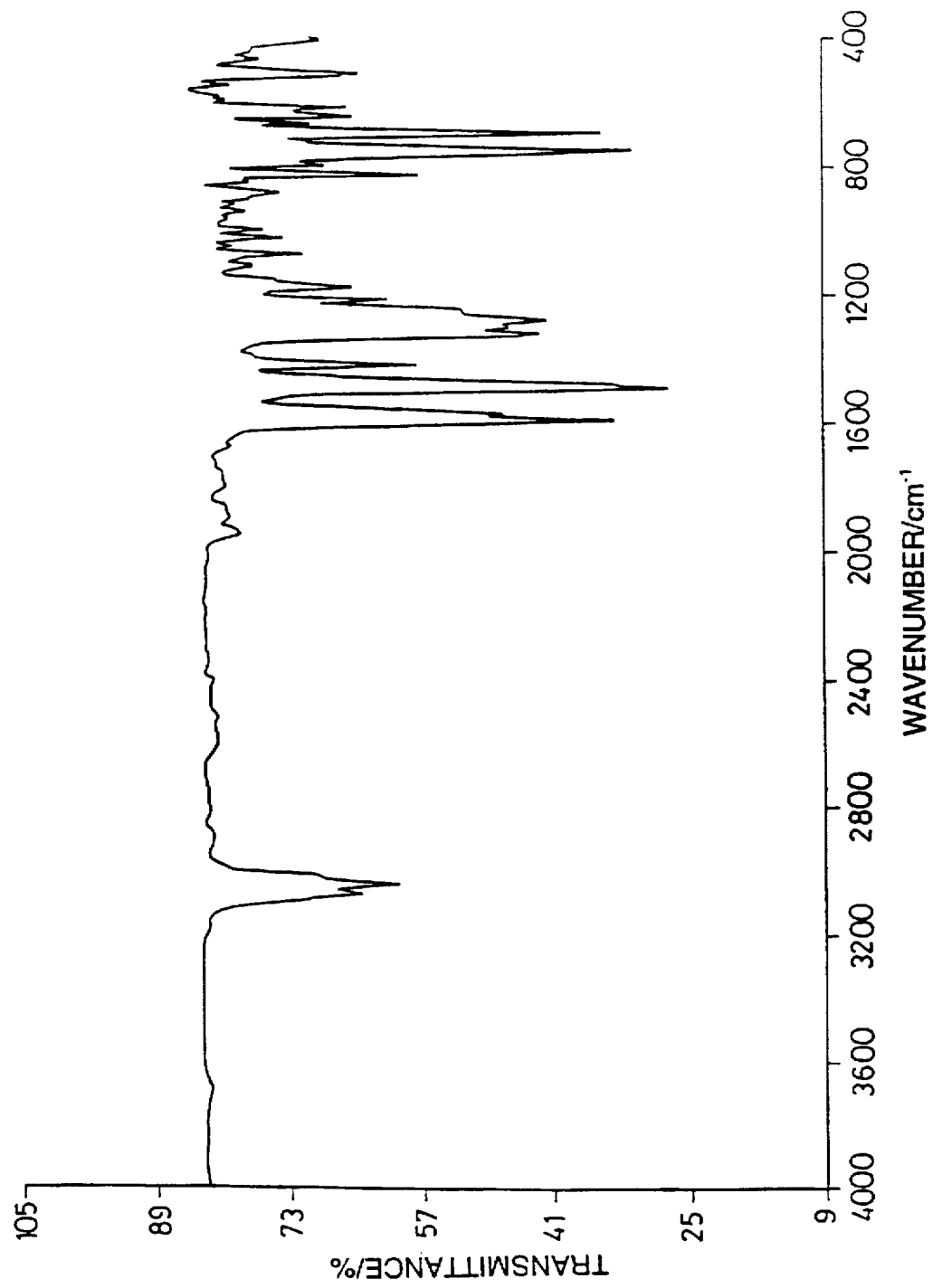
FIG. 8 is a diagram showing a IR absorption spectrum of the inventive compound (VII-1) of Example 3.

IR absorption spectrum: FIG. 8.

Figure 9:
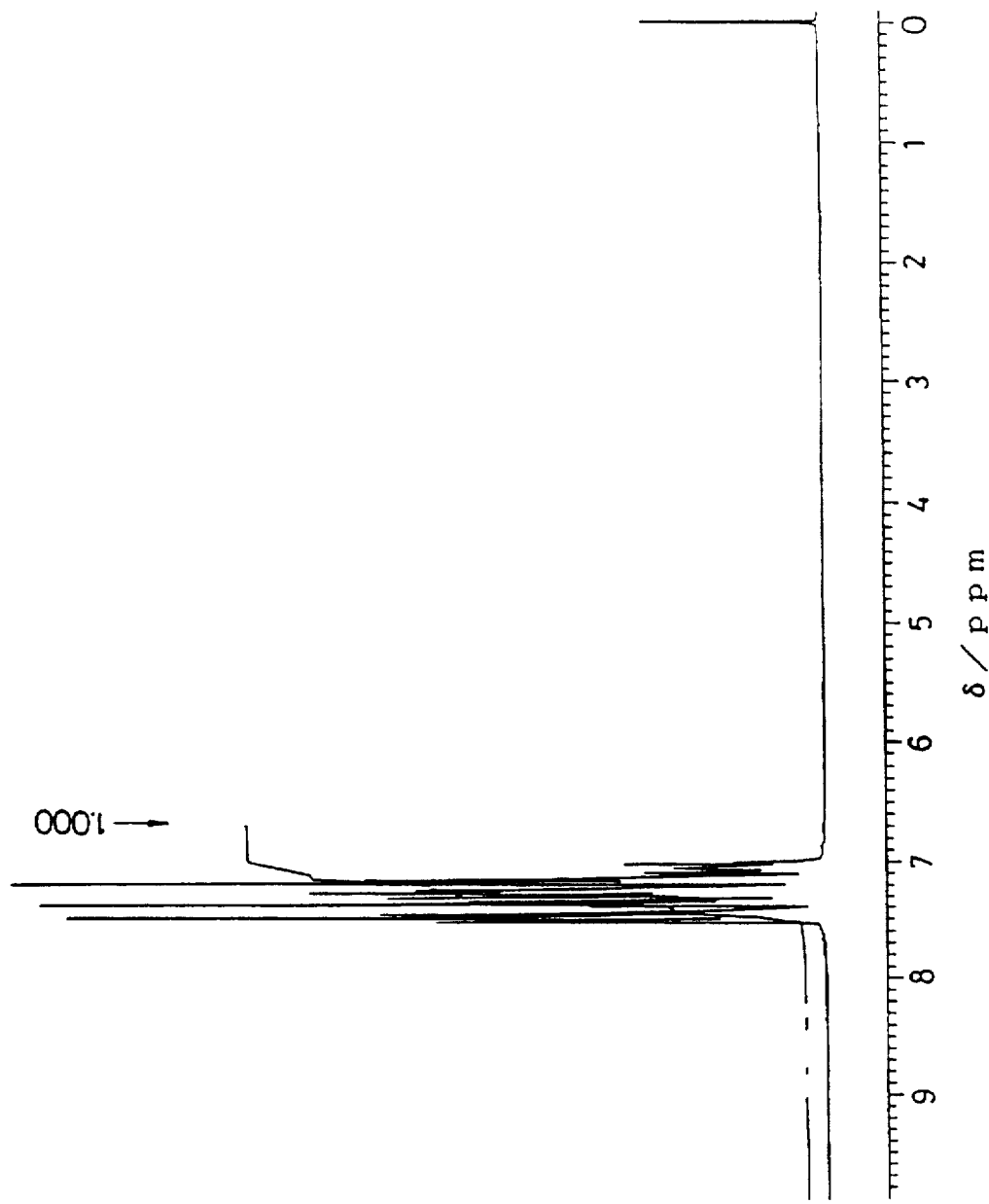
FIG. 9 is a diagram showing a NMR spectrum of compound (VII-1).

NMR spectrum: FIG. 9.

DSC: mp 189.8° C. Tg 83.6° C.

Example 4

Synthesis of N,N'-diphenyl-N,N'-bis |4'-(N-phenyl-N-3-methylphenylamino)biphenyl-4-yl|benzidine, compound No. X-10

A 500-ml reactor was charged with 33.6 g (0.10 mol) of N,N'-diphenylbenzidine, 25.0 g (0.11 mol) of m-iodotoluene, 27.6 g (0.2 mol) of potassium carbonate, 2.6 g of copper powder, and 200 ml of nitrobenzene. In an argon stream, the contents were heated under reflux for 24 hours. At the end of reaction, the insoluble was removed by filtration and the solvent was distilled off from the filtrate. The still residue was purified twice through a silica gel column with a ½mixture of n-hexane and toluene, obtaining 28.10 g of N,N'-diphenyl-N-|4-(N-phenyl-N-3-methylphenylamino)-biphenyl-4-yl|benzidine (yield 42%).

A 500-ml reactor was charged with 8.1 g (0.02 mol) of 4,4'-diiodobiphenyl, 28.1 g (0.02 mol) of N,N'-diphenyl-N-|4(N-phenyl-N-3-methylphenylamino)-biphenyl-4-yl| benzidine, 11.04 g (0.08 mol) of potassium carbonate, 1.0 g of copper powder, and 100 ml of nitrobenzene. In an argon stream, the contents were heated under reflux for 24 hours. At the end of reaction, the insoluble was removed by filtration and the solvent was distilled off from the filtrate. The still residue was purified twice through a silica gel column with a 2/1 mixture of n-he and toluene, obtaining 11.62 g of highly pure N,N'-diphenyl-N,N'-bis [4'-(N-phenyl-N-3-methylphoylamino)-biphenyl-4-yl]benzidine (yield 58%). It was further purified by recrystallization from a solvent mixture of hexane and toluene, obtaining 7.3 g of a 99.9% pure, pale yellow, clear, amorphous mass.

mass analysis: m/e 1002 (M$^+$).

Figure 10:
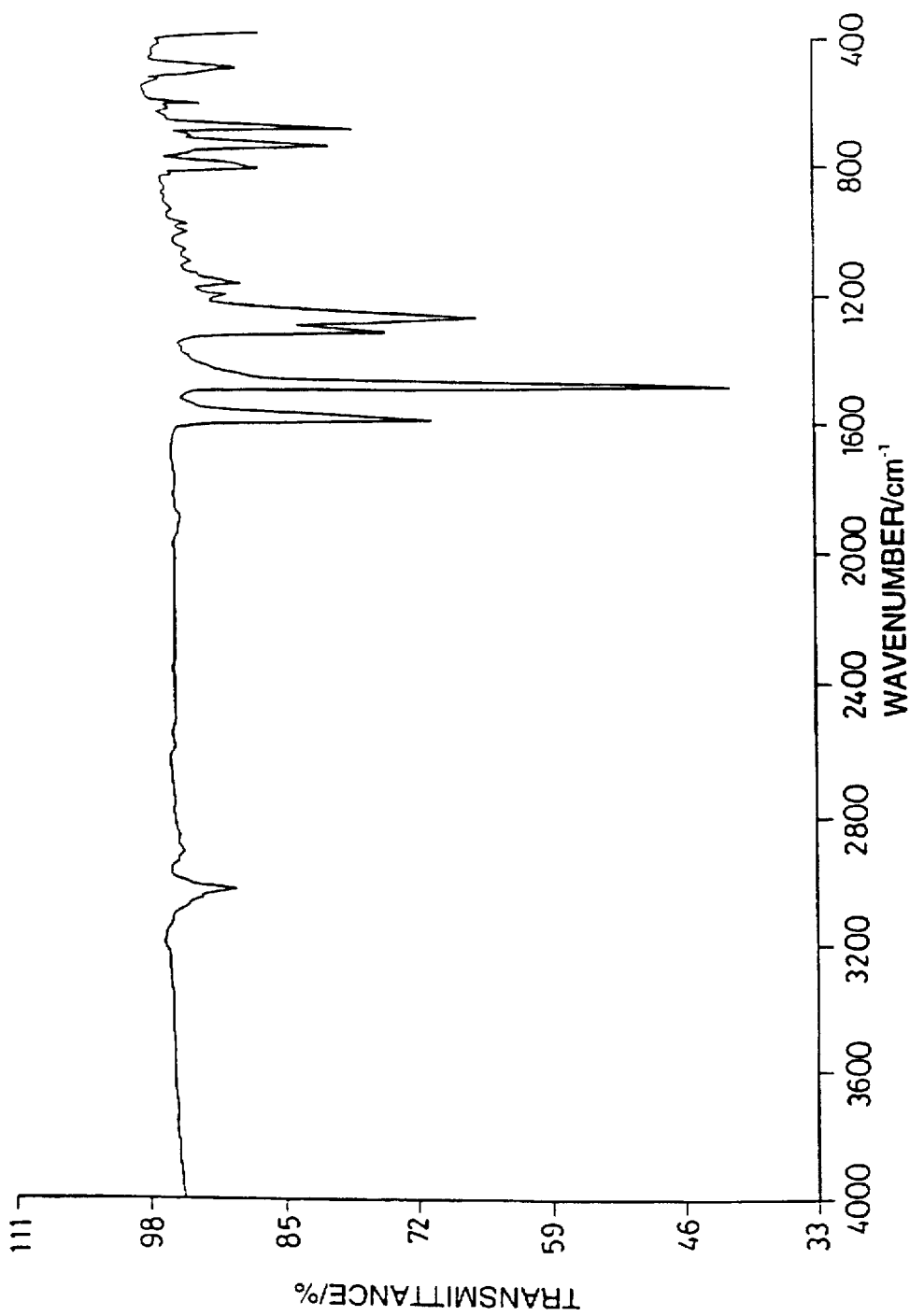
FIG. 10 is a diagram showing a IR absorption spectrum of the inventive compound (X-10) of Example 4.

IR absorption spectrum: FIG. 10.

Figure 11:
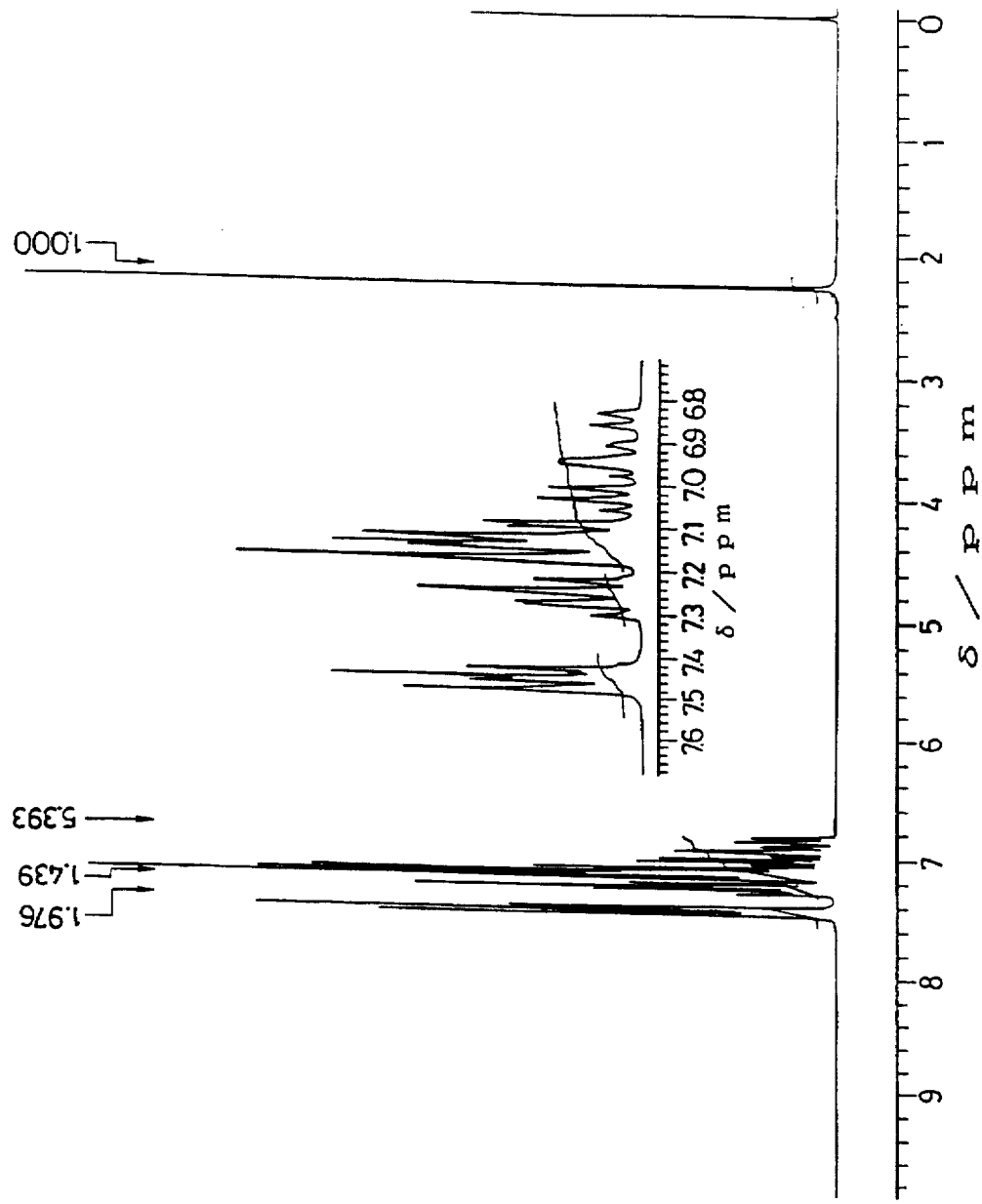
FIG. 11 is a diagram showing a NMR spectrum of compound (X-10).

NMR spectrum: FIG. 11.

DSC: mp not observed (amorphous from the initial)Tg 132° C.

Example 5

Synthesis of N,N'-diphenyl-N,N'-bis|4'-(N,N-di-3-biphenylylamino)biphenyl-4-yl]benzidine, compound No. X-3

A 300-ml reactor was charged with 16.1 g (0.050 ml) of di(3-biphenylyl)amino, 20.3 g (0.050 mol) of 4,4'-diiodobiphenyl, 13.8 g (0.10 mol) of potassium carbonate, 1.0 g of copper powder, and 100 ml of nitrobenzene. In an argon stream, the contents were heated under reflux for 24 hours. At the end of reaction, the insoluble was removed by filtration and the solvent was distilled off from the filtrate. The still residue was purified through a silica gel column with a 5/1 mixture of n-hexane and toluene, obtaining 12.0 g of 4'-|N,N'-di(3-biphenylylamio)|-4-iodo-1,1'-biphenyl (yield 40%).

A 300-ml reactor was charged with 12.0 g (0.020 mol) of 4'-[N,N'-di (3-biphenylylamino)-|4-iodo-1,1'-biphenyl, 3.03 g (0.009 mol) of N,N'-diphenylbenzidine, 5.52 g (0.04 mol) of potassium carbonate, 0.5 g of copper powder, and 100 ml of nitrobenzene. In an argon stream, the contents were heated under reflux for 24 hours. At the end of reaction, the insoluble was removed by filtration and the solvent was distilled off from the filtrate. The still residue was purified twice through a silica gel column with a 2/1 mixture of toluene and n-hexane, obtaining 6.90 g of N,N'-diphenyl-N, N'-bis |4'-(N,N-di-3-biphenylylamino) biphenyl-4-yl| benzidine (yield 60%). It was further purified by recrystallization from toluene, obtaining 5.2 g of a 99.9% pure, pale yellow, clear, amorphous mass.

This compound was also identified by mass analysis, IR, and NMR as in Example 4.

The remainder of the previously exemplified compounds were synthesized by the same procedures as above and identified by mass analysis, IR and NMR.

Example 6

A glass substrate having an ITO transparent electrode (anode) of 200 nm thick was subjected to ultrasonic cleaning with neutral detergent, acetone, and ethanol. The substrate was pulled up from boiling ethanol, dried, and further subjected to UV/ozone cleaning. The substrate was secured by a holder in an evaporation chamber, which was evacuated to a vacuum of 1×10$^{-4}$ Pa or lower.

Then the compound (I-1) of Example 1 was evaporated at a deposition rate of 0.2 nm/sec. to deposit a transparent amorphous thin film of 55 nm thick. It was allowed to stand in a constant temperature chamber at 30° C./RH 100% and 60° C./RH 90%, both severer than the atmospheric air, over 10 months. The thin film underwent no crystallization and maintained a stable amorphous state, indicating good thin film-forming ability and storage stability. A similarly deposited film was found to have ionization potential Ip of 5.35 eV as measured by a low energy electron spectrometer Model AC-1 manufactured by Riken Keiki Co., Ltd.

Example 7

Using compounds (II-1) and (VII-1) of Examples 2 and 3, experiments were done as in Example 6. Similarly no crystallization occurred during storage over 10 monthly The evaporated films had an ionization potential Ip of 5.36 eV and 5.38 eV.

Example 8

Using compounds (X-10) and (X-3) of Examples 4 and 5, experiments were done as in Example 6. Similarly no crystallization occurred during storage over 10 months. The evaporated films had an ionization potential Ip of 5.32 eV and 5.28 eV.

Comparative Example 1

Thin films were deposited as in Example 6 except that the compound of Example 1 was replaced by compound (1): N,N'-diphelyl-N,N'-di (3-methylphenyl)-4,4'-diamino-1,1'-biphenyl (mp: 171.2° C., Tg: 61.3° C.) or compound (2): 1,1'-bis(4-di-p-tolylaminophenyl) cyclohexane (mp: 187.8° C., Tg: 79.9° C.). The thin films were allowed to stand in a constant temperature chamber at 30° C./RH 100%. Although the films were allowed to stand in a milder temperature environment than Examples 6 to 8, crystallization started on the third day in the film of compound (1) and on the 30th day in the film of compound (2).

As in Example 6, the film of compounds (1) and (2) were measured for ionization potential. Both had an Ip of 5.40 eV.

Example 9

A glass substrate having an ITO transparent electrode (anode) of 200 nm thick was subjected to ultrasonic cleaning with neutral detergent, acetone, and ethanol. The substrate was pulled up from boiling ethanol, dried, and further subjected to UV/ozone cleaning. The substrate was secured by a holder in an evaporation chamber, which was evacuated to a vacuum of $1 \times 10^{-4}$ Pa or lower.

First compound (I-1) of Example 1 was evaporated at a deposition rate of 0.2 nm/sec. to a thickness of 75 nm, forming a hole injecting and transporting layer.

With the vacuum kept, tris(8-quinolinolato)aluminum was evaporated at a deposition rate of 0.2 nm/sec. to a thickness of 50 n forming an electron injecting and transporting/light emitting layer.

With the vacuum kept further, MgAg (weight ratio 10:1) was evaporated at a deposition rate of 0.2 nm/sec. to a thickness of 200 nm to form a cathode, obtaining an organic EL element.

With a DC voltage applied, the EL element was continuously driven at a constant current density of 10 mA/cm$^2$ in-a dry atmosphere. At the initial, mission of yellowish green light (maximum wavelength λmax=500 nm) at a luminance of 400 cd/m$^2$ was observed with a drive voltage of 6.5 V. A half life of luminance was 600 hours, during which the drive voltage increased 4.0 V. The deposited film of tris(8-quinolinolato)aluminum serving as the light emitting layer had an Ip of 5.64 eV, with the difference in Ip from the film of compound (I-1) serving as the hole injecting and transporting layer being 0.29 eV.

Example 10 and 11

EL elements were manufactured as in Example 9 except that compound (I-1) was replaced by compounds (II-1) and (VII-1) of Examples 2 and 3. They were similarly tested.

Comparative Example 2 and 3

EL elements were manufactured as in Example 9 except that compound (I-1) was replaced by compounds (1) and (2) of Comparative Example 1. They were similarly tested.

The results of Examples 9–11 and Comparative Example 2–3 are show in table 16.

TABLE 16

| | Com- pound | Initial | | Luminance half-life | | Dif- ferential |
|---|---|---|---|---|---|---|
| | | Luminance (cd/m$^2$) | Voltage (V) | Time (hr.) | Voltage Rise (V) | Ip (eV) |
| E9 | (I-1) | 400 | 6.5 | 600 | 4.0 | 0.29 |
| E10 | (II-1) | 420 | 6.5 | 620 | 4.1 | 0.28 |
| E11 | (VII-1) | 380 | 6.6 | 500 | 3.8 | 0.26 |
| CE2 | (1) | 300 | 5.2 | 120 | 7.6 | 0.24 |
| CE3 | (2) | 360 | 8.5 | <19* | breakdown | 0.24 |

*The drive voltage rose to 11.5 V after 3 hours, and the element broke down on the next day (after 19 hours).

Examples 12 and 13

EL elements were manufactured as in Example 9 except that compound (I-1) was replaced by compounds (X-10) and (X-3) of Examples 4 and 5. They were similarly tested. The results were at least comparable to those of Example 9. The differential Ip from tris(8-quinolinolato)aluminum was 0.32 eV for compound (X-10) of Example 4 and 0.36 eV for compound (X-3) of Example 5.

Example 14

A glass substrate having an ITO transparent electrode (anode) of 200 nm thick was subjected to ultrasonic cleaning with neutral detergent, acetone, and ethanol. The substrate was pulled up from boiling ethanol, dried, and further subjected to UV/ozone cleaning. The substrate was secured by a holder in an evaporation chamber, which was evacuated to a vacuum of $1 \times 10^{-4}$ Pa or lower.

First poly(thiophene-2,5-diyl) was evaporated at a deposition rate of 0.1 nm/sec. to a thickness of 20 nm, forming a first hole injecting and transporting layer.

Then with the vacuum kept, compound (I-1) of Example 1 was evaporated at a deposition rate of 0.2 nm/sec. to a thickness of 55 nm, forming a second hole injecting and transporting layer.

With the vacuum kept, tris(8-quinolinolato)aluminum was evaporated at a deposition rate of 0.2 nm/sec. to a thickness of 50 nm, forming an electron injecting and transporting/light emitting layer. With the vacuum kept further, MgAg (weight ratio 10:1) was evaporated at a deposition rate of 0.2 nm/sec. to a thickness of 200 nm to form a cathode, obtaining an organic EL element.

With a DC voltage applied, the EL element was continuously driven at a constant current density of 10 mA/cm$^2$ in a dry atmosphere. At the initial, emission of yellowish green light (maximum wavelength λmax=500 nm) at a luminance of 350 cd/m$^2$ was observed with a drive voltage of 6.0 V. A half life of luminance was 1600 hours, during which the drive voltage increased 2.3 V. No development or growth of dark spots was observed. Thereafter, no current leakage occurred and stable light mission continued.

These results fully satisfy the requirements for the EL element to be applied as a display. As an accelerated lifetime test, the EL element was continuously driven at a higher current density of 40 mA/cm$^2$, finding a high luminance of 1400 cd/m$^2$ at the initial and a half life of 400 hours, with a concomitant drive voltage rise of 5.0 V.

Examples 15 and 16

EL elements were manufactured as in Example 14 except that compound (I-1) was replaced by compounds (II-1) and (VII-1) of Examples 2 and 3. They were similarly tested at a current density of 10 mA/cm$^2$.

The results of the EL elements of Examples 14–16 at a current density of 10 MA/cm$^2$ are shown in Table 17.

TABLE 17

| | Com- pound | Initial | | Luminance half-life | | Dif- ferential |
|---|---|---|---|---|---|---|
| | | Luminance (cd/m$^2$) | Voltage (V) | Time (hr.) | Voltage Rise (V) | Ip (eV) |
| E14 | (I-1) | 350 | 6.0 | 1600 | 2.3 | 0.29 |
| E15 | (II-1) | 360 | 5.8 | 1800 | 2.5 | 0.28 |
| E16 | (VII-1) | 330 | 5.8 | 1500 | 2.3 | 0.26 |

Example 17 and 18

EL elements were manufactured as in Example 14 except that compound (I-1) was replaced by compounds (X-10) and (X-3) of Examples 4 and 5. They were similarly tested at a current density of 10 mA/cm$^2$. The results were at least comparable to those of Example 14.

Example 19

A glass substrate having an ITO transparent electrode (anode) of 200 nm thick was subjected to ultrasonic clearing with neutral detergent, acetone, and ethanol. The substrate was pulled up from boiling ethanol, died, and further subjected to UV/ozone cleaning. The substrate was secured by a holder in an evaporation chamber, which was evacuated to a vacuum of $1\times10^{-4}$ Pa or lower.

First compound (I-1) of Example 1 and rubrene were evaporated and co-deposited at a rate of 0.2 nm/sec. and 0.02 nm/sec. to a total thickness of 75 nm, forming a hole injecting and transporting layer.

With the vacuum kept, tris(8-quinolinolato)aluminum was evaporated and deposited at a rate of 0.2 nm/sec. to a thickness of 50 nm, forming an electron injecting and transporting/light emitting layer.

With the vacuum kept further, NgAg (weight ratio 10:1) was evaporated and deposited at a rate of 0.2 nm/sec. to a thickness of 200 nm to form a cathode, obtaining an organic EL element.

With a DC voltage applied, the EL element was continuously driven at a constant current density of 10 mA/cm$^2$ in a dry atmosphere. At the initial, emission of yellow light (maximum wavelength λmax=550 nm) at a luminance of 550 cd/m$^2$ was observed with a drive voltage of 6.2 V. A half life of luminance was 1,500 hours, during which the drive voltage increased 2.8 V.

Example 20 and 21

EL elements were manufactured as in File 19 except that compound (I-1) was replaced by compounds (II-1) and (VII-1) of Examples 2 and 3. They were similarly tested.

The results of the EL elements of Examples 12–14 are shown in Table 18.

TABLE 18

| | | Initial | | Luminance half-life | | Differential |
|---|---|---|---|---|---|---|
| | Compound | Luminance (cd/m$^2$) | Voltage (V) | Time (hr.) | Voltage Rise (V) | Ip (eV) |
| E19 | (I-1) | 550 | 6.2 | 1500 | 2.8 | 0.29 |
| E20 | (II-1) | 580 | 6.1 | 1600 | 3.0 | 0.28 |
| E21 | (VII-1) | 530 | 6.2 | 1300 | 2.9 | 0.26 |

Examples 22 and 23

EL elements were manufactured as in Example 19 except that compound (I-1) was replaced by compounds (X-10) and (X-3) of Examples 4 and 5. They were similarly tested. The results were at least comparable to those of Example 19.

Example 24

A glass substrate having an ITO transparent electrode (anode) of 200 nm thick was subjected to ultrasonic cleaning with neutral detergent, acetone, and ethanol. The substrate was pulled up from boiling ethanol, dried, and further subjected to UV/ozone cleaning. The substrate was secured by a holder in an evaporation chamber, which was evacuated to a vacuum of $1\times10^{-4}$ Pa or lower.

First poly(thiophene-2,5-diyl) was evaporated at a deposition rate of about 0.1 nm/sec. to a thickness of about 20 nm, forming a first hole injecting and transporting layer.

Then the vacuum chamber was released to the atmospheric air and evacuated again to a vacuum of $1\times10^{-4}$ Pa or lower. The compound (I-1) of Example 1 and rubrene were evaporated and co-deposited at a rate of 0.1–0.2 nm/sec. and 0.01–0.02 nm/sec. to a total thickness of about 55 nm, forming a second hole injecting and, transporting layer.

With the vacuum kept, tris(8-quinolinolato)aluminum was evaporated and deposited at a rate of 0.1–0.2 nm/sec. to a thickness of about 50 mm, forming an electron injecting and transporting/light emitting layer.

With the vacuum kept further, MgAg (weight ratio 10:1) was evaporated at a deposition rate of 0.2 nm/sec. to a thickness of about 200 nm to form a cathode, obtaining an organic EL element.

With a DC voltage applied, the EL element was continuously driven at a constant current density of 10 mA/cm$^2$ in a dry atmosphere. At the initial, emission of yellow light (maximum wavelength λmax=550 nm) at a luminance of 420 cd/m$^2$ was observed with a drive voltage of 6.2 V. A half life of luminance was 2,000 hours, during which the drive voltage increased 4.9 V.

These results fully satisfy the requirements for the EL element to be applied as a display. As an accelerated lifetime test, he EL element was continuously driven at a higher current density of 40 mA/cm$^2$, finding a high luminance of 1490 cd/m$^2$ at the initial and a half Life of 500 hours, with a concomitant drive voltage rise of 3.5 V.

Example 25

An EL element was manufactured as in Example 24 except that compound (X-10) of Example 4 was use in the second hole injecting and transporting layer instead of compound (I-1). It was similarly tested. The results were at least comparable to those of Example 24.

Example 26

A glass substrate having ITO transparent electrode (anode) of 200 nm thick was subjected to ultrasonic cleaning with neutral detergent, acetone, and ethanol. The substrate was pulled up from boiling ethanol, dried, and further subjected to UV/ozone cleaning. The substrate was secured by a holder in an evaporation chamber, which was evacuated to a vacuum of $1\times10^{-4}$ Pa or lower.

First compound (I-1) of Example 1 was evaporated at a deposition rate of 0.1–0.2 nm/sec. to a thicknees of about 55 nm, forming a hole injecting and transporting layer.

Then with the vacuum kept, the hole injecting and transporting material and tris(8-quinolinolato)aluminum as an electron injecting and transporting material were evaporated and co-deposited at d substantially equal rate of 0.1–0.2 nm/sec. to form a mix layer of about 40 nm thick as a light emitting layer.

With the vacuum kept, the electron injecting and transporting material was evaporated and deposited at a rate of 0.1–0.2 nm/sec. to a thickness of about 30 nm, forming a electron injecting and transporting layer.

With the vacuum kept further, NgAg (weight ratio 10:1) was evaporated at a deposition rate of 0.2 nm/sec. to a thickness of about 200 nm to form a cathode, obtaining an organic EL element.

With a DC voltage applied, the EL element was continuously driven at a constant current density of 10 mA/cm$^2$ in a dry atmosphere. At the initial, emission of yellowish green light (maximum wavelength λmax=500 nm) at a luminance of 470 cd/m$^2$ was observed with a drive voltage of 6.7 V. A half life of luminance was 2,000 hours, during which the drive voltage increased 3.0 V.

Example 27

An El element was manufactured as in Example 26 except that compound (X-10) of Example 4 was used in the hole injecting and transporting layer and mix layer (light emitting layer) instead o compound (-1). It was similarly tested. The results were at least comparable to those of Example 26.

Example 28

A glass substrate having an ITO transparent electrode (anode) of 200 mm thick was subjected to ultrasonic cleaning with neutral detergent, acetone, and ethanol. The substrate was pulled up from boiling ethanol, dried, and further subjected to UV/ozone cleaning. The substrate was secured by a holder in an evaporation chamber, which was evacuated to a vacuum of $1 \times 10^{-4}$ Pa or lower.

First poly(thiophene-2,5-diyl) was evaporated at a deposition rate of about 0.1 nm/sec. to a thickness of about 20 nm, forming a first hole injecting and transporting layer.

Then the vacuum chamber was released to the atmospheric air end evacuated again to a vacuum of $1 \times 10^{-4}$ Pa or lower. The compound (I-1) of Example 1 was evaporated and deposited at a rate of 0.1–0.2 nm/sec. to a thickness of about 35 mm, forming a second hole injecting and transporting layer.

With the vacuum kept, the second hole injecting and transporting material and tris(8-quinolinolato)aluminum as an electron injecting and transporting material were evaporated and co-deposited at a substantially equal rate of 0.1–0.2 nm/sec. to form a mix layer of about 40 nm thick as a light emitting layer.

With the vacuum kept, the electron injecting and transporting material was evaporated and deposited at a rate of 0.1–0.2 nm/sec. to a thickness of about 30 nm, forming an electron injecting and transporting layer.

With the vacuum kept further, XgAg (weight ratio 10:1) was evaporated at a deposition rate of 0.2 nm/sec. to a thickness of about 200 nm to form a cathode, obtaining an organic EL element.

With a DC voltage applied, the EL element was continuously driven at a constant current density of 10 mA/cm$^2$ in a dry atmosphere. At the initial, emission of yellowish green light (maximum wavelength λmax=500 nm) at a luminance of 350 cd/m$^2$ was observed with a drive voltage of 6.1 V. A half life of luminance was 3,000 hours, during which the drive voltage increased 5.0 V.

Example 29

An EL element was manufactured as in Example 28 except that the mix layer was 10 nm thick. It was similarly tested. At the initial, emission of yellowish green light (maximum wavelength λmax=500 nm) at a luminance of 360 cd/m$^2$ was observed with a drive voltage of 6.2 V. A half life of luminance was 2,100 hours, during which the drive voltage increased 3.3 V.

Example 30

An EL element was manufactured as in Example 28 except that compound (X-10) of Example 4 was used in the second hole injecting and transporting layer and mix layer (light emitting layer) instead of compound (I-1). It was similarly tested. The results were at least comparable to those of Example 28.

Examples 9 to 30 were repeated using at least one of the illustrated examples of the inventive compound instead of compounds (I1), (II-1), (VII-1), (X-10), and (X-3). They were similarly tested to find similar results complying with respective element constructions.

There have been described compounds in the form of tetraaryldiamine derivatives which have a high melting point and high glass transition temperature and form, by evaporation, transparent smooth thin films of quality which maintain a stable amorphous state above room temperature over a long term. The inventive compounds can form thin films by themselves without a need for binder resin.

The organic EL elements using organic EL element-forming compounds including the inventive compounds in organic compound layers thereof, typically in a hole injecting and transporting layer thereof provide uniform plane light emission and maintain high luminance in a stable manner over a long term. Thus the elements are fully durable and reliable.

Those EL elements including two hole injecting and transporting layers, one layer containing the inventive compound and the other layer containing polythiophene, can operate at a reduced drive voltage with a suppressed rise thereof and without development of dark spots over a long term, maintaining stable light mission. The embodiment of the EL element designed such that the differential Ip is optimized has a reduced initial drop of luminance and an extended lifetime of light emission. Those EL elements having a rubrene doped layer are improved in initial luminance and have an extended lifetime of light emission. Those EL elements having a mix layer containing the inventive compound and a compound having an electron injecting and transporting function as a light emitting layer also have an extended life of light emission.

Japanese Patent Application Nos. 014379/1994 and 145293/1994 are incorporated herein by reference.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. An organic electroluminescent element comprising two electrodes and a layer between said electrodes containing at least one organic electroluminescent element forming compound of the following formula (2):

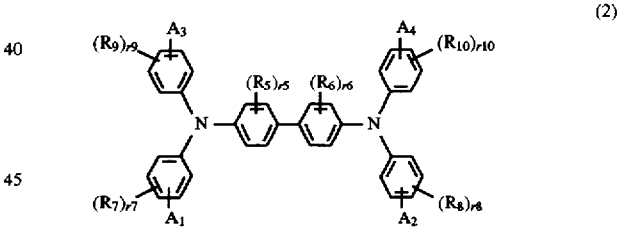

(2)

wherein $A_1$, $A_2$, $A_3$, and $A_4$, which may be identical or different, are aryl groups attached to the corresponding benzene ring at the para- or meta-position with respect to the position of attachment to the nitrogen atom.

$R_7$, $R_8$, $R_9$, and $R_{10}$, are independently selected from the group consisting of an alkyl group, alkoxy group, aryl group, aryloxy group, amino group and halogen atom, r7, r8, r9, and r10 are independently 0 or an integer of 1 to 4, $R_5$ and $R_6$ are independently selected from the group consisting of an alkyl group, alkoxy group, amino group, and halogen atom, and r5 and r6 are independently 0 or an integer of 1 to 4.

2. The organic electroluminescent element of claim 1 wherein at least one of the aryl groups represented by A1 to A4 is a naphthyl, anthryl, pyrenyl, perylenyl or coronenyl group.

3. The organic electroluminescent element of claim 1 wherein said compound has the following formula (4):

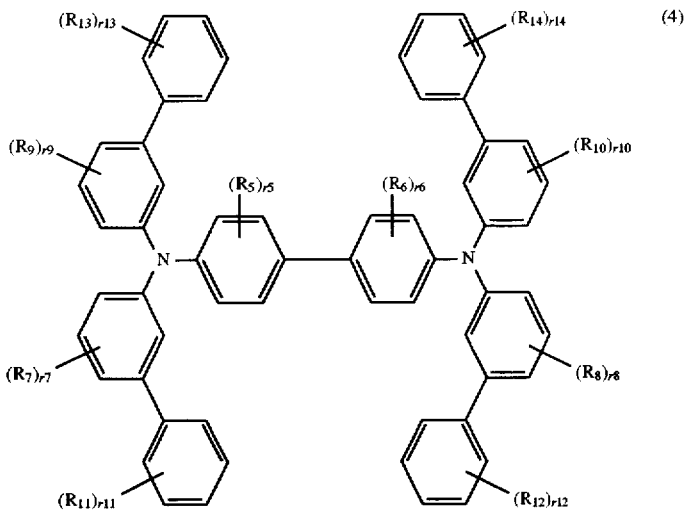

(4)

wherein $R_7$, $R_8$, $R_9$, and $R_{10}$ are independently selected from the group consisting of an alkyl group, alkoxy group, aryl group, aryloxy group, amino group and halogen atom, r7, r8, r9, and r10 are independently 0 or an integer of 1 to 4, $R_{11}$, $R_{12}$, $R_{13}$, and $R_{14}$ are independently selected from the group consisting of an alkyl group, alkoxy group, aryl group, aryloxy group, amino group and halogen atom, r11, r12, r13, and r14 are independently 0 or an integer of 1 to 5, $R_5$ and $R_6$ are independently selected from the group consisting of an alkyl group, alkoxy group, amino group, and halogen atom, and r5 and r6 are independently 0 or an integer of 1 to 4.

4. The organic electroluminescent element of claim 3 wherein r5, r6, r7, r8, r9, r10, r11, r12, r13, and r14 are equal to 0.

5. The organic electroluminescent element of claim 1 wherein said compound has the following formula (5):

wherein $R_7$, $R_8$, $R_9$, and $R_{10}$ are independently selected from the group consisting of an alkyl group, alkoxy group, aryl group, aryloxy group, amino group and halogen atom, r7, r8, r9, and r10 are independently 0 or an integer of 1 to 4, $R_{11}$, $R_{12}$, $R_{13}$, and $R_{14}$ are independently selected from the group consisting of an alkyl group, alkoxy group, aryl group, aryloxy group, amino group and halogen atom, r11, r12, r13, and r14 are independently 0 or an integer of 1 to 5, $R_5$ and $R_6$ are independently selected from the group consisting of an alkyl group, alkoxy group, amino group, and halogen atom, and r5 and r6 are independently 0 or an integer of 1 to 4.

6. The organic electroluminescent element of claim 9 wherein r5, r6, r7, r8, r9, r10, r11, r12, r13, and r14 are equal to 0.

7. The organic electroluminescent element of claim 5, wherein at least one of $R_7$, $R_8$, $R_9$, and $R_{10}$ is diphenylamino.

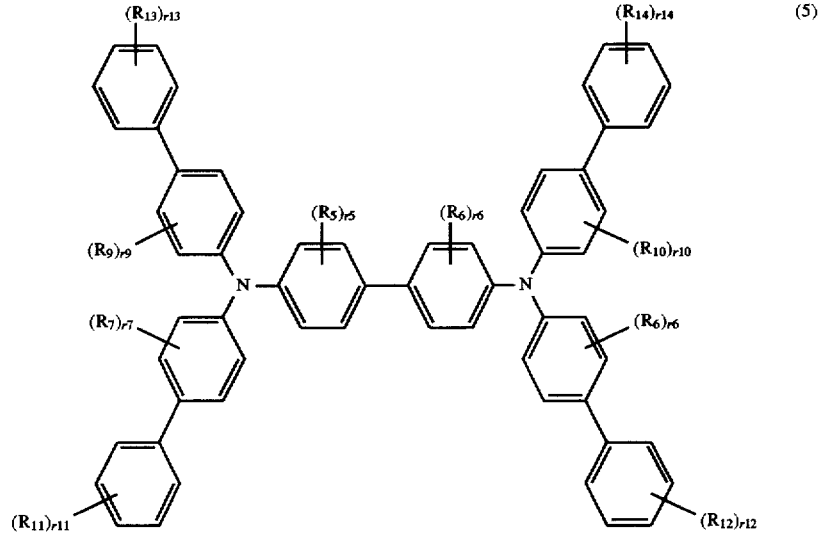

(5)

bis(biphenyl)amino, N-phenyl-N-tolylamino, N-phenyl-N-biphenylamino, bis(naphthylamino), bis(anthryl)amino, or bis(pyrenyl)amino.

8. The organic electroluminescent element of claim 1 wherein said compound has the following formula (6):

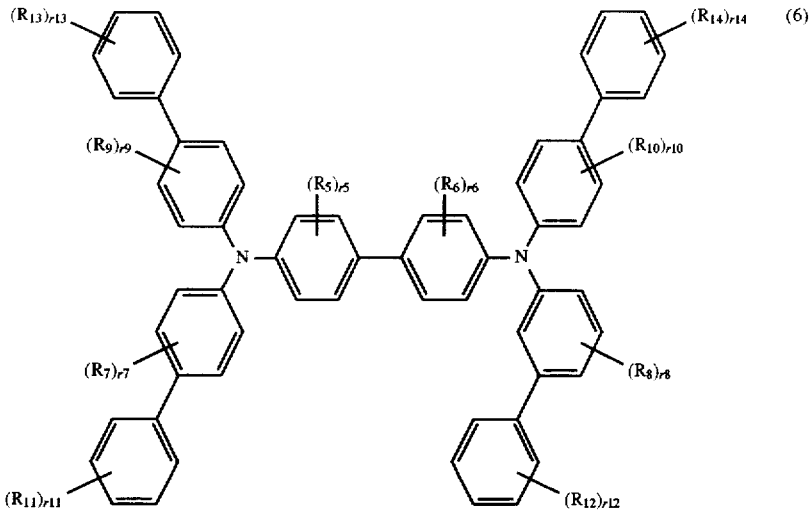

wherein $R_7$, $R_8$, $R_9$, and $R_{10}$ are independently selected from the group consisting of an alkyl group, alkoxy group, aryl group, aryloxy group, amino group and halogen atom.

r7, r8, r9, and r10 are independently 0 or an integer of 1 to 4, $R_{11}$, $R_{12}$, $R_{13}$, and $R_{14}$ are independently selected from the group consisting of an alkyl group, alkoxy group, aryl group, aryloxy group, amino group and halogen atom, r11, r12, r13, and r14 are independently 0 or an integer of 1 to 5, $R_5$ and $R_6$ are independently selected from the group consisting of an alkyl group, alkoxy group, amino group, and halogen atom, and r5 and r6 are independently 0 or an integer of 1 to 4.

9. The organic electroluminescent element of claim 8 wherein r5, r6, r7, r8, r9, r10, r11, r12, r13, and r14 are equal to 0.

10. The organic electroluminescent element of claim 1 wherein said compound has the following formula (7):

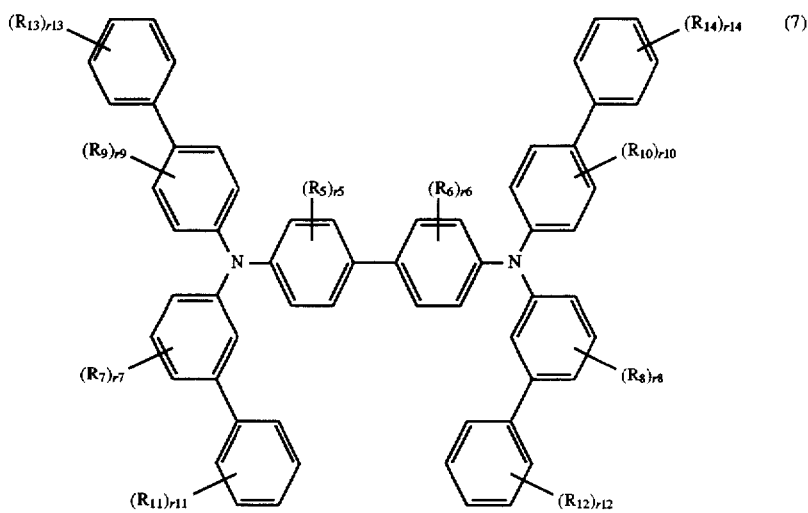

wherein $R_7$, $R_8$, $R_9$, and $R_{10}$ are independently selected from the group consisting of an alkyl group, alkoxy group, aryl group, aryloxy group, amino group and halogen atom, r7, r8, r9, and r10 are independently 0 or an integer of 1 to 4, $R_{11}$, $R_{12}$, $R_{13}$, and $R_{14}$ are independently selected from the group consisting of an alkyl group, alkoxy group, aryl group, aryl group, amino group and halogen atom, r11, r12, r13, and r14 are independently 0 or an integer of 1 to 5, $R_5$ and $R_6$ are independently selected from the group consisting of an alkyl group, alkoxy group, amino group, and halogen atom, and r5 and r6 are independently 0 or an integer of 1 to 4.

11. The organic electroluminescent element of claim 10 wherein r5, r6, r7, r8, r9, r10, r11, r12, r13, and r14 are equal to 0.

12. The organic electroluminescent element of claim 1 wherein said compound has the following formula (8):

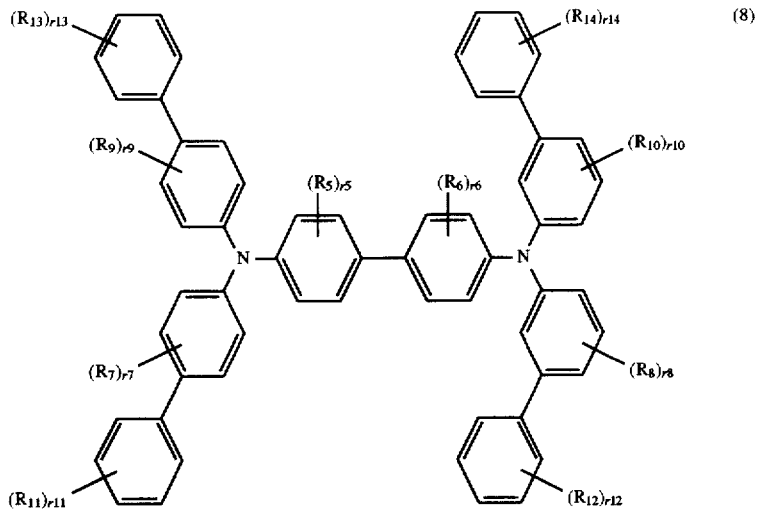

wherein $R_7$, $R_8$, $R_9$, and $R_{10}$ are independently selected from the group consisting of an alkyl group, alkoxy group, aryl group, aryloxy group, amino group and halogen atom, r7, r8, r9, and r10 are independently 0 or an integer of 1 to 4, $R_{11}$, $R_{12}$, $R_{13}$, and $R_{14}$ are independently selected from the group consisting of an alkyl group, alkoxy group, aryl group, aryloxy group, amino group and halogen atom, r11, r12, r13, and r14 are independently 0 or an integer of 1 to 5, $R_5$ and $R_6$ are independently selected from the group consisting of an alkyl group, alkoxy group, amino group, and halogen atom, and r5 and r6 are independently 0 or an integer of 1 to 4.

13. The organic electroluminescent element of claim 12 wherein r5, r6, r7, r8, r9, r10, r11, r12, r13, and r14 are equal to 0.

14. The organic electroluminescent element of claim 1 wherein said compound has the following formula (9):

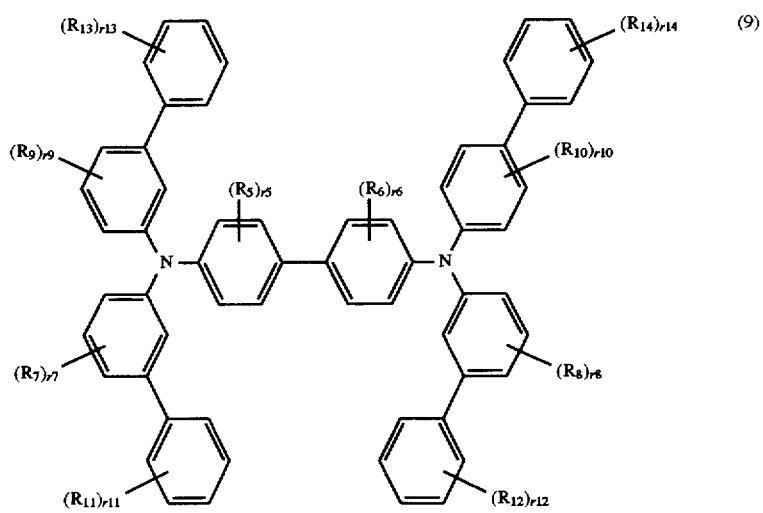

wherein $R_7$, $R_8$, $R_9$, and $R_{10}$ are independently selected from the group consisting of an alkyl group, alkoxy group, aryl group, aryloxy group, amino group and halogen atom, r7, r8, r9, and r10 are independently 0 or an integer of 1 to 4, $R_{11}$, $R_{12}$, $R_{13}$, and $R_{14}$ are independently selected from the group consisting of an alkyl group, alkoxy group, aryl group, aryloxy group, amino group and halogen atom, r11, r12, r13, and r14 are independently 0 or an integer of 1 to 5, $R_5$ and $R_6$ are independently selected from the group consisting of an allyl group, alkoxy group, amino group, and halogen atom, and r5 and r6 are independently 0 or an integer of 1 to 4.

15. The organic electroluminescent element of claim 14 wherein r5, r6, r7, r8, r9, r10, r11, r12, r13, and r14 are equal to 0.

16. An organic electroluminescent element comprising two electrodes and a layer between said electrodes containing at least one organic electroluminescent element-forming compound of the following formula (3):

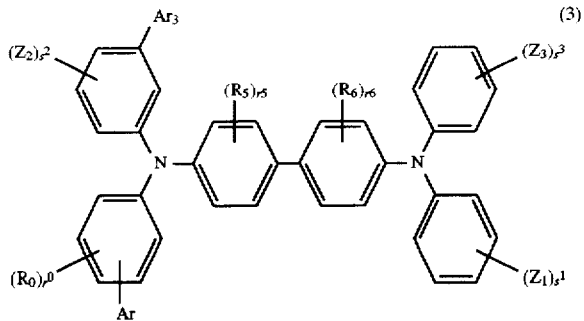

wherein Ar is an aryl group attached to the corresponding benzene ring at the para- or meta-position with respect to the position of attachment to the nitrogen atom.

$Z_1$, $Z_2$, and $Z_3$ are independently selected from the group consisting of an alkyl group, alkoxy group, aryl group, aryloxy group, amino group and halogen atom, one or two of $Z_1$, $Z_2$, and $Z_3$ is an aryl group attached to the corresponding benzene ring at the para- or meta-position with respect to the position of attachment to the nitrogen atom, with the proviso that when two of Ar, $Z_1$, $Z_2$, and $Z_3$ are aryl groups, at least one of Ar, $Z_1$, $Z_2$, and $Z_3$ is attached to the corresponding benzene ring at the meta-position with respect to the position of attachment to the nitrogen atom or two of Ar, $Z_1$, $Z_2$, and $Z_3$ are diarylamino aryl groups attached to the corresponding ring at the para-position with respect to the position of attachment to the nitrogen atom.

s1, s2, and s3 are independently 0 or an integer of 1 to 5, the sum of s1, s2, and s3 is an integer of at least 1, $R_0$ is selected from the group consisting of an alkyl group, alkoxy group, aryl group, aryloxy group, amino group and halogen atom, r0 is 0 or an integer of 1 to 4, $R_5$ and $R_6$ are independently selected from the group consisting of an alkyl group, alkoxy group, amino group, and halogen atom, and r5 and r6 are independently 0 or an integer of 1 to 4.

17. The organic electroluminescent element of claim 16 wherein said compound has the following formula (10):

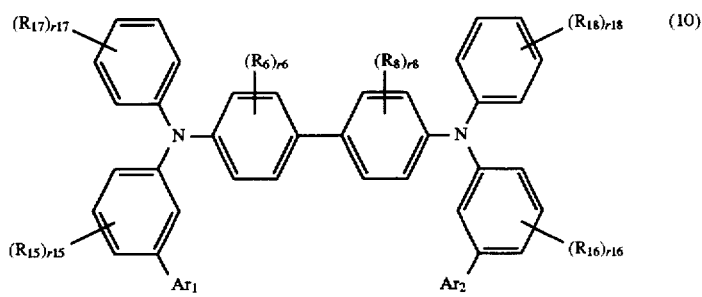

wherein $Ar_1$ and $Ar_2$ which may be identical or different are aryl groups, $R_{15}$ and $R_{16}$ are independently selected from the group consisting of an alkyl group, alkoxy group, aryl group, aryloxy group, amino group and halogen atom, r15 and r16 are independently 0 or an integer of 1 to 4, $R_{17}$ and $R_{18}$ are independently selected from the group consisting of an alkyl group, alkoxy group, aryloxy group, amino group and halogen atom, r17 and r18 are independently 0 or an integer of 1 to 5, $R_5$ and $R_6$ are independently selected from the group consisting of an alkyl group, alkoxy group, amino group, and halogen atom, and r5 and r6 are independently 0 or an integer of 1 to 4.

18. The organic electroluminescent element of claim 17 wherein r5, r6, r15, r16, r17, and r18 are equal to 0.

19. The organic electroluminescent element of claim 16 wherein said compound has the following formula (11):

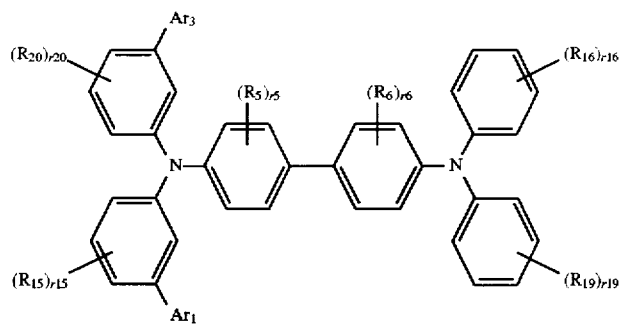

(11)

wherein $Ar_1$ and $Ar_3$ which may be identical or different are aryl groups.

$R_{15}$ and $R_{20}$ are independently selected from the group consisting of a alkyl group, alkoxy group, aryl group, aryloxy group, amino group and halogen atom, r15 and r20 are independently 0 or an integer of 1 to 4, $R_{18}$ and $R_{19}$ are independently selected from the group consisting of an alkyl group, alkoxy group, aryloxy group, amino group and halogen atom, r18 and r19 are independently 0 or an integer of 1 to 5, $R_5$ and $R_6$ are independently selected from the group consisting of an alkyl group, alkoxy group, amino group, and halogen atom, and r5 and r6 are independently 0 or an integer of 1 to 4.

20. The organic electroluminescent element of claim 19 wherein r5, r6, r15, r18, r19, and r20 are equal to 0.

21. The organic electroluminescent element of claim 16 wherein said compound has the following formula (12):

$R_{15}$, $R_{16}$, and $R_{20}$ are independently selected from the group consisting of an alkyl group, alkoxy group, aryl group, aryloxy group, amino group and halogen atom, r15, r16, and r20 are independently 0 or an integer of 1 to 4, $R_{18}$ is selected from the group consisting of an alkyl group, alkoxy group, aryloxy group, amino group and halogen atom.

r18 is 0 or an integer of 1 to 5, $R_5$ and $R_6$ are independently selected from the group consisting of an alkyl group, alkoxy group, amino group, and halogen atom, and r5 and r6 are independently 0 or an integer of 1 to 4.

22. The organic electroluminescent element of claim 21 wherein r5, r6, r15, r16, r18, and r20 are equal to 0.

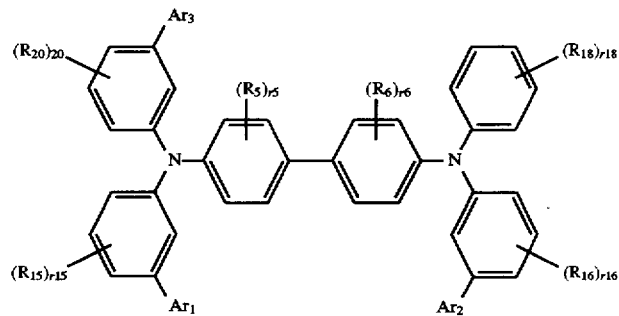

(12)

wherein $Ar_1$, $Ar_2$, and $Ar_3$ which may be identical or different are aryl groups.

23. The organic electroluminescent element of claim 16 wherein said compound has the following formula (13):

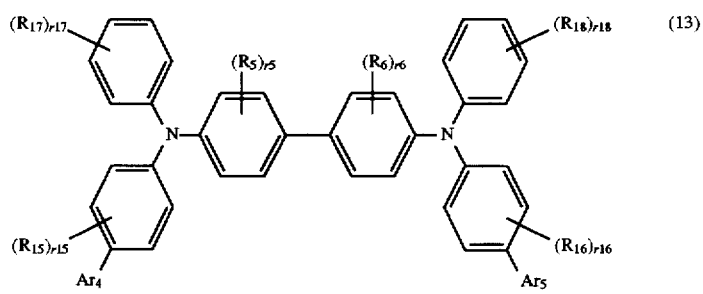

(13)

wherein Ar4 and Ar5 which may be identical or different are aryl groups, $R_{15}$ and $R_{16}$ are independently selected from the group consisting of an alkyl group, alkoxy group, aryl group, aryloxy group, amino group and halogen atom, r15 and r16 are independently 0 or an integer of 1 to 4, $R_{17}$ and $R_{18}$ are independently selected from the group consisting of an alkyl group, alkoxy group, aryloxy group, amino group and halogen atom, r17 and r18 are independently 0 or an integer of 1 to 5, $R_5$ and $R_6$ are independently selected from the group consisting of an alkyl group, alkoxy group, amino group, and halogen atom, and r5 and r6 are independently 0 or an integer of 1 to 4.

24. The organic electroluminescent element of claim 23 wherein r5, r6, r15, r16, r17, and r18 are equal to 0.

25. The organic electroluminescent element of claim 16 wherein said compound has the following formula (14):

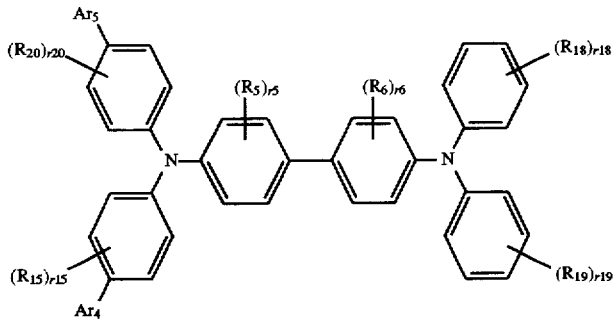

(14)

wherein $Ar_4$ and $Ar_6$ which may be identical or different are aryl groups, $R_{15}$ and $R_{20}$ are independently selected from the group consisting of an alkyl group, alkoxy group, aryl group, aryloxy group, amino group and halogen atom, r15 and r20 are independently 0 or an integer of 1 to 4, $R_{18}$ and $R_{19}$ are independently selected from the group consisting of an alkyl group, alkoxy group, aryloxy group, amino group and halogen atom, r18 and r19 are independently 0 or an integer of 1 to 5, $R_5$ and $R_6$ are independently selected from the group consisting of an alkyl group, alkoxy group, amino group, and halogen atom, and r5 and r6 are independently 0 or an integer of 1 to 4.

26. The organic electroluminescent element of claim 25 wherein r5, r6, r15, r18, r19, and r20 are equal to 0.

27. The organic electroluminescent element of claim 16 wherein said compound has the following formula (15):

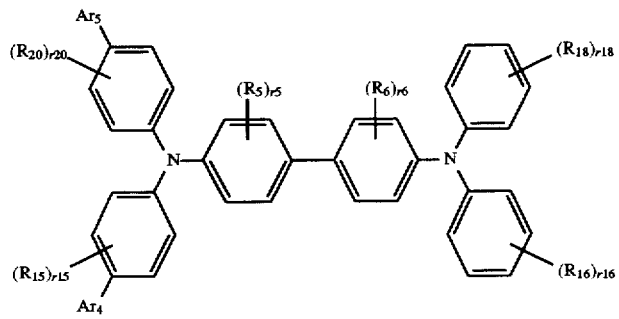

(15)

wherein $Ar_4$, $Ar_5$, and $Ar_6$ which may be identical or different are aryl groups, $R_{15}$, $R_{16}$, and $R_{20}$ are independently selected from the group consisting of an alkyl group, alkoxy group, aryl group, aryloxy group, amino group and halogen atom, r15, r16, and r20 are independently 0 or an integer of 1 to 4, $R_{18}$ is selected from the group consisting of an alkyl group, alkoxy group, aryloxy group, amino group and halogen atom, r18 is 0 or an integer of 1 to 5, $R_5$ and $R_6$ are independently selected from the group consisting of an alkyl group, alkoxy group, amino group, and halogen atom, and r5 and r6 are independently 0 or an integer of 1 to 4.

28. The organic electroluminescent element of claim 27 wherein r5, r6, r15, r16, r18, and r20 are equal to 0.

29. The organic electroluminescent element of claim 1 or 16, additionally comprising at least one mix layer containing a mixture of the organic electroluminescent element-forming compound and at least one compound having an electron injecting and transporting function.

30. The organic electroluminescent element of claim 29 wherein the compound having an electron injecting and transporting function is tris(8-quinolinolato)aluminum.

31. The organic electroluminescent element of claim 29 wherein said mix layer is a light emitting layer.

32. The organic electroluminescent element of claim 1 or 16 wherein said layer containing an organic electroluminescent element-forming compound is doped with a fluorescent material.

33. The organic electroluminescent element of claim 32 wherein said fluorescent material is rubrene.

34. The organic electroluminescent element of claim 1 or 16 wherein said layer containing an organic electroluminescent element-forming compound is a hole injecting and transporting layer and the element further includes a light emitting layer.

35. The organic electroluminescent element of claim 34 wherein said hole injecting and transporting layer includes at least two layers having different compositions.

36. The organic electroluminescent element of claim 35 wherein at least one of said hole injecting and transporting layers contains a polythiophene.

37. The organic electroluminescent element of claim 1 or 16 which further includes an electron injecting and transporting layer.

38. The electroluminescent element of claim 1 or 16 wherein said layer containing an organic electroluminescent element-forming compound is a layer having a hole injecting and transporting function, a layer having a light emitting function or electron injecting and transporting function is disposed adjacent said layer, and the difference in ionization potential Ip between said layer having a hole injecting and transporting function and said layer having a light emitting function or electron injecting and transporting function is at least 0.25 eV.

* * * * *

UNITED STATES PATENT AND TRADEMARK OFFICE
CERTIFICATE OF CORRECTION

PATENT NO. : 5,792,557
DATED : August 11, 1998
INVENTOR(S) : Kenji Nakaya, et. al.

It is certified that error appears in the above-identified patent and that said Letters Patent is hereby corrected as shown below:

Column 134, lines 63 and 64, "A1 to A4" should read --$A_1$ to $A_4$--.

Column 136, line 38, "claim 9" should read --claim 5--.

Column 138, line 61, "aryl" (second occurrence) should read --aryloxy--.

Column 140, line 58, "$R_{11}$, $R_{12}$, $R_{13}$ --" should read --$R_{11}$, $R_{12}$, $R_{13}$,--.
line 64, "allyl" shoul read --alkyl--.

Column 145, line 1, "Ar4" should read --$Ar_4$--.

UNITED STATES PATENT AND TRADEMARK OFFICE
CERTIFICATE OF CORRECTION

PATENT NO. : 5,792,557
DATED : August 11, 1998
INVENTOR(S) : Kenji Nakaya, et. al.

It is certified that error appears in the above-identified patent and that said Letters Patent is hereby corrected as shown below:

Column 135, formula 5

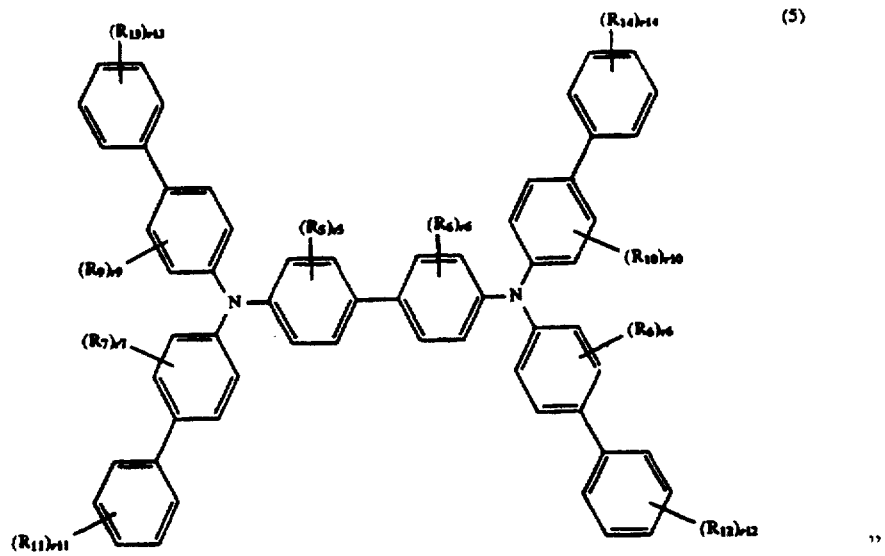

UNITED STATES PATENT AND TRADEMARK OFFICE
CERTIFICATE OF CORRECTION

PATENT NO. : 5,792,557
DATED : August 11, 1998
INVENTOR(S) : Kenji Nakaya, et. al.

It is certified that error appears in the above-identified patent and that said Letters Patent is hereby corrected as shown below:

should read --

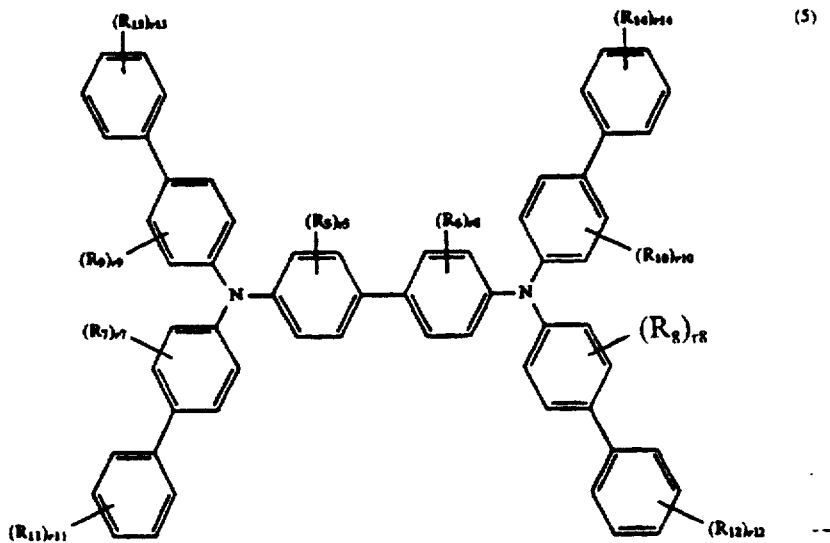

--

UNITED STATES PATENT AND TRADEMARK OFFICE
CERTIFICATE OF CORRECTION

PATENT NO. : 5,792,557
DATED : August 11, 1998
INVENTOR(S) : Kenji Nakaya, et. al.

Page 4 of 9

It is certified that error appears in the above-identified patent and that said Letters Patent is hereby corrected as shown below:

Column 141, formula 3

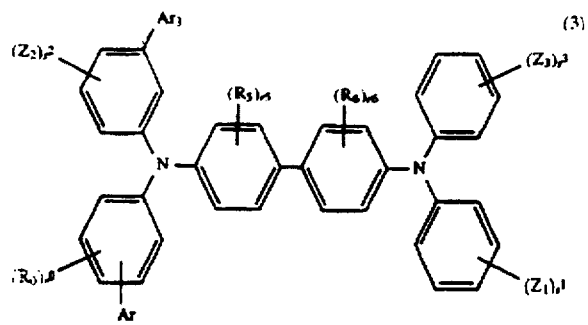

should read

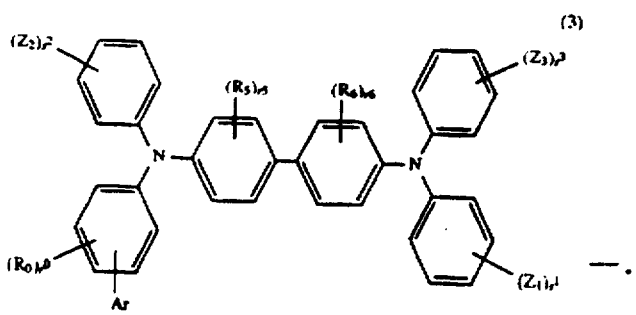

UNITED STATES PATENT AND TRADEMARK OFFICE
CERTIFICATE OF CORRECTION

Page 5 of 9

PATENT NO. : 5,792,557
DATED : August 11, 1998
INVENTOR(S) : Kenji Nakaya, et. al.

It is certified that error appears in the above-identified patent and that said Letters Patent is hereby corrected as shown below:

Column 142, formula 10

"

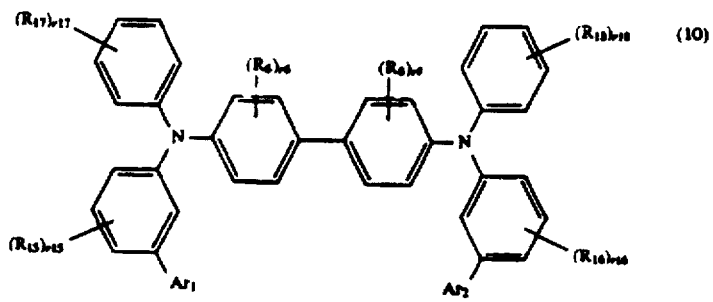

should read

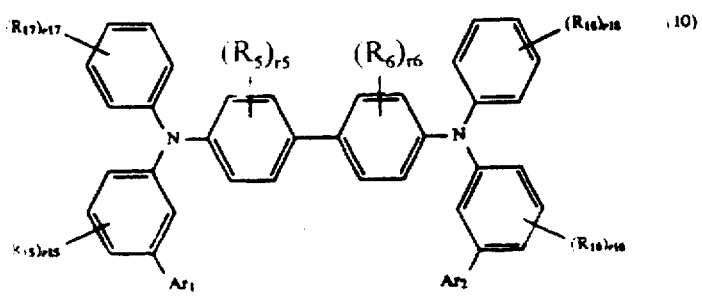

UNITED STATES PATENT AND TRADEMARK OFFICE
CERTIFICATE OF CORRECTION

PATENT NO. : 5,792,557
DATED : August 11, 1998
INVENTOR(S) : Kenji Nakaya, et. al.

It is certified that error appears in the above-identified patent and that said Letters Patent is hereby corrected as shown below:

Column 143, formula 11

"

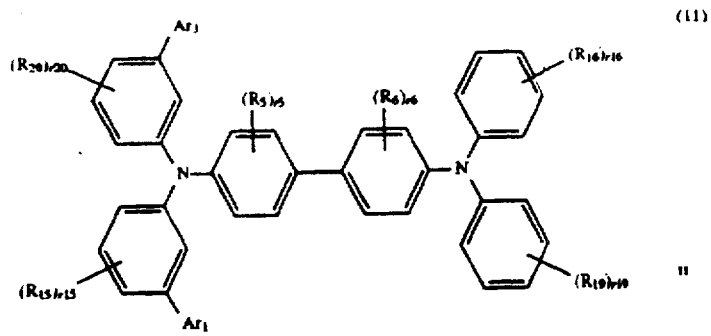

"

should read

-- 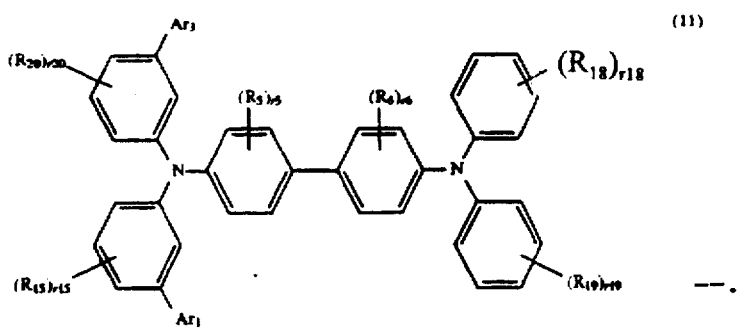 --.

UNITED STATES PATENT AND TRADEMARK OFFICE
CERTIFICATE OF CORRECTION

Page 7 of 9

PATENT NO. : 5,792,557
DATED : August 11, 1998
INVENTOR(S) : Kenji Nakaya, et. al.

It is certified that error appears in the above-identified patent and that said Letters Patent is hereby corrected as shown below:

Column 145, formula 14

"

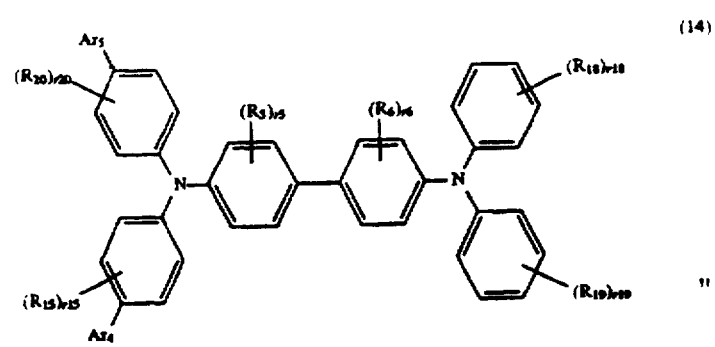

should read

--

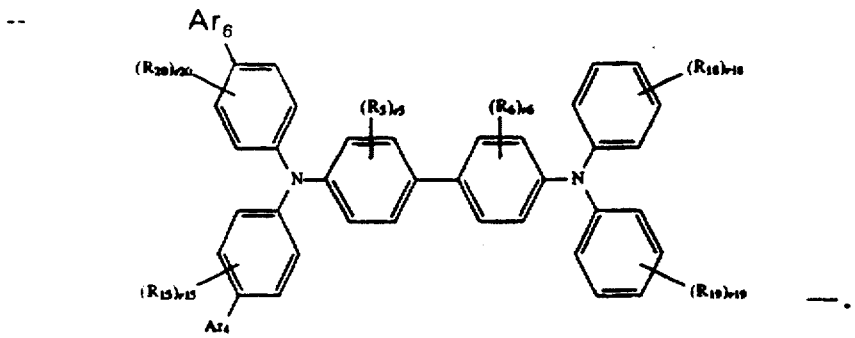

--.

UNITED STATES PATENT AND TRADEMARK OFFICE
CERTIFICATE OF CORRECTION

PATENT NO. : 5,792,557
DATED : August 11, 1998
INVENTOR(S) : Kenji Nakaya, et. al.

It is certified that error appears in the above-identified patent and that said Letters Patent is hereby corrected as shown below:

Col. 145, formula 15

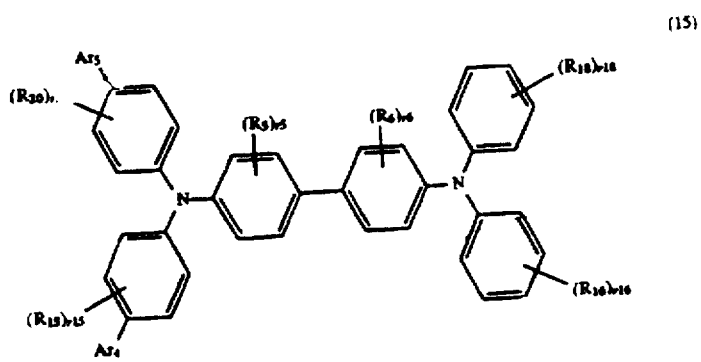

UNITED STATES PATENT AND TRADEMARK OFFICE
CERTIFICATE OF CORRECTION

PATENT NO. : 5,792,557  
DATED : August 11, 1998  
INVENTOR(S) : Kenji Nakaya, et. al.

Page 9 of 9

It is certified that error appears in the above-identified patent and that said Letters Patent is hereby corrected as shown below:

should read

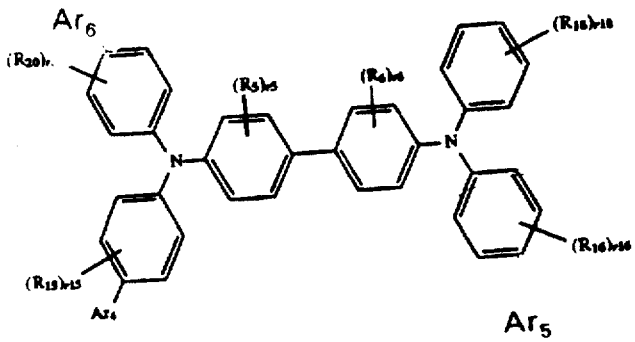

(15)

Signed and Sealed this

Twenty-fourth Day of August, 1999

Attest:

Q. TODD DICKINSON

*Attesting Officer*   *Acting Commissioner of Patents and Trademarks*